US009814658B2

(12) United States Patent
Ishak et al.

(10) Patent No.: US 9,814,658 B2
(45) Date of Patent: Nov. 14, 2017

(54) HIGH ENERGY VISIBLE LIGHT FILTER SYSTEMS WITH YELLOWNESS INDEX VALUES

(71) Applicant: High Performance Optics, Inc., Roanoke, VA (US)

(72) Inventors: Andrew W. Ishak, Havre de Grace, MD (US); Sean P. McGinnis, Roanoke, VA (US); Ronald D. Blum, Roanoke, VA (US); Michael B. Packard, Cincinnati, OH (US)

(73) Assignee: High Performance Optics, Inc., Roanoke, VA (US)

( * ) Notice: Subject to any disclaimer, the term of this patent is extended or adjusted under 35 U.S.C. 154(b) by 103 days.

(21) Appl. No.: 14/497,013

(22) Filed: Sep. 25, 2014

(65) Prior Publication Data

US 2015/0064123 A1 Mar. 5, 2015

Related U.S. Application Data

(60) Division of application No. 13/174,998, filed on Jul. 1, 2011, now Pat. No. 8,882,267, which is a continuation-in-part of application No. 11/933,069, filed on Oct. 31, 2007, now Pat. No. 8,360,574, which is a continuation-in-part of application No. 11/761,892, filed on Jun. 12, 2007, now Pat. No. 7,520,608, which is a continuation-in-part of application No. 11/378,317, filed on Mar. 20, 2006, now abandoned, said application No. 11/933,069 is a continuation-in-part of application No. 11/892,460, filed on Aug. 23, 2007, now Pat. No. 7,556,376.

(60) Provisional application No. 61/361,677, filed on Jul. 6, 2010, provisional application No. 60/812,628, filed on Jun. 12, 2006, provisional application No. 60/839,432, filed on Aug. 23, 2006, provisional application No. 60/841,502, filed on Sep. 1, 2006, provisional application No. 60/861,247, filed on Nov. 28, 2006, provisional application No. 60/978,175, filed on Oct. 8, 2007, provisional application No. 61/440,941, filed on Feb. 9, 2011, provisional application No. 61/415,890, filed on Nov. 22, 2010, provisional application No. 61/377,603, filed on Aug. 27, 2010.

(51) Int. Cl.
| | | |
|---|---|---|
| *G02C 7/00* | (2006.01) | |
| *G02C 7/02* | (2006.01) | |
| *G02C 7/06* | (2006.01) | |
| *A61K 8/31* | (2006.01) | |
| *A61F 2/16* | (2006.01) | |
| *G02B 5/22* | (2006.01) | |
| *G02C 7/04* | (2006.01) | |
| *G02C 7/10* | (2006.01) | |
| *A61K 8/34* | (2006.01) | |
| *A61K 8/49* | (2006.01) | |
| *A61K 8/58* | (2006.01) | |
| *A61K 8/81* | (2006.01) | |
| *A61Q 17/04* | (2006.01) | |

(52) U.S. Cl.
CPC .............. *A61K 8/31* (2013.01); *A61F 2/1613* (2013.01); *A61K 8/345* (2013.01); *A61K 8/492* (2013.01); *A61K 8/58* (2013.01); *A61K 8/8129* (2013.01); *A61Q 17/04* (2013.01); *G02B 5/223* (2013.01); *G02C 7/04* (2013.01); *G02C 7/10* (2013.01); *G02C 7/104* (2013.01); *A61F 2/1659* (2013.01); *A61K 2800/10* (2013.01); *G02C 2202/16* (2013.01)

(58) Field of Classification Search
CPC ........ A61K 8/31; A61K 8/345; A61K 8/8129; A61K 8/492; A61K 8/58; A61Q 17/04
USPC ..................... 548/402, 419; 585/26; 424/59; 351/159.49
See application file for complete search history.

(56) References Cited

U.S. PATENT DOCUMENTS

| | | | |
|---|---|---|---|
| 3,687,863 | A | 8/1972 | Wacher |
| 4,017,292 | A | 4/1977 | Mann |
| 4,247,177 | A | 1/1981 | Marks et al. |
| 4,390,676 | A | 6/1983 | Loshaek |
| 4,581,288 | A | 4/1986 | Barnhart et al. |
| 4,656,186 | A | 4/1987 | Bommer et al. |
| 4,679,918 | A | 7/1987 | Ace |
| 4,698,374 | A | 10/1987 | Gallas |
| 4,793,669 | A | 12/1988 | Perilloux |
| 4,795,461 | A | 1/1989 | Lindqvist et al. |
| 4,826,286 | A | 5/1989 | Thornton |
| 4,878,748 | A | 11/1989 | Johansen et al. |
| 4,952,046 | A | 8/1990 | Stephens et al. |
| 5,054,902 | A | 10/1991 | King |

(Continued)

FOREIGN PATENT DOCUMENTS

| | | |
|---|---|---|
| CN | 1879041 A | 12/2006 |
| CN | 1961041 A | 5/2007 |

(Continued)

OTHER PUBLICATIONS

Baumeister, P. & Pincus, G. 1970. Optical Interference Coatings. ScientificAmerican.
The International Search Report corresponding to EP 11804243.1.
The International Search Report corresponding to the PCT/US2011/42922 application.
The Office Communication dated Feb. 17, 2012 in the related Chinese application No. 200780050536.2.
CRC Handbook of Chemistry and Physics 85th Ed. 2004-2005 pp. 10-217.
Ernest, "Light-transmission-spectrum comparison of foldable intraocular lenses" J. Cataract Refract Surg., vol. 30, 2004, p. 1755-1758.

(Continued)

*Primary Examiner* — James Greece
(74) *Attorney, Agent, or Firm* — Sterne, Kessler, Goldstein & Fox P.L.L.C.

(57) ABSTRACT

The present invention relates to ophthalmic and non-ophthalmic systems with blue light filtering and Yellowness Index ranges. UV and IR filtering are also included. Industrial applications are also outlined in the invention.

14 Claims, 50 Drawing Sheets

(56) References Cited

U.S. PATENT DOCUMENTS

| | | |
|---|---|---|
| 5,149,183 A | 9/1992 | Perrott et al. |
| 5,172,256 A | 12/1992 | Sethofer et al. |
| 5,177,509 A | 1/1993 | Johansen et al. |
| 5,374,663 A | 12/1994 | Daicho et al. |
| 5,400,175 A | 3/1995 | Johansen et al. |
| 5,470,932 A | 11/1995 | Jinkerson |
| 5,521,765 A | 5/1996 | Wolfe |
| 5,528,322 A | 6/1996 | Jinkerson |
| 5,534,041 A | 7/1996 | Havens et al. |
| 5,543,504 A | 8/1996 | Jinkerson |
| 5,617,154 A | 4/1997 | Hoffman |
| 5,662,707 A | 9/1997 | Jinkerson |
| 5,694,240 A | 12/1997 | Sternbergh |
| 5,702,819 A | 12/1997 | Gupta et al. |
| 5,729,379 A | 3/1998 | Allemand et al. |
| 6,021,001 A | 2/2000 | Turner |
| 6,102,539 A | 8/2000 | Tucker |
| 6,145,984 A | 11/2000 | Farwig |
| 6,158,862 A | 12/2000 | Patel et al. |
| 6,220,703 B1 | 4/2001 | Evans et al. |
| 6,231,183 B1 | 5/2001 | Dillon |
| 6,277,940 B1 | 8/2001 | Niwa et al. |
| 6,305,801 B1 | 10/2001 | Kerns et al. |
| 6,306,316 B1 | 10/2001 | Mann et al. |
| 6,310,215 B1 | 10/2001 | Iwamoto |
| 6,326,448 B1 | 12/2001 | Ojio et al. |
| 6,334,680 B1 | 1/2002 | Larson |
| 6,373,615 B1 | 4/2002 | Mann et al. |
| 6,411,450 B1 | 6/2002 | Gatewood et al. |
| 6,444,146 B2 | 9/2002 | Yoshimura et al. |
| 6,541,032 B1 | 4/2003 | Medelnick et al. |
| 6,554,424 B1 | 4/2003 | Miller et al. |
| 6,604,824 B2 | 8/2003 | Larson |
| 6,641,261 B2 | 11/2003 | Wang et al. |
| 6,793,339 B1 | 9/2004 | Yip et al. |
| 6,851,074 B2 | 2/2005 | Milojicic et al. |
| 6,863,848 B2 | 3/2005 | Engardio et al. |
| 6,918,931 B2 | 7/2005 | Lai et al. |
| 6,926,405 B2 | 8/2005 | Ambler et al. |
| 6,955,430 B2 | 10/2005 | Pratt |
| 6,960,231 B2 | 11/2005 | Tran |
| 6,972,034 B2 | 12/2005 | Tran et al. |
| 6,984,038 B2 | 1/2006 | Ishak |
| 6,984,734 B2 | 1/2006 | Sessler et al. |
| 6,986,579 B2 | 1/2006 | Blum et al. |
| 7,029,118 B2 | 4/2006 | Ishak |
| 7,029,758 B2 | 4/2006 | Gallas et al. |
| 7,033,391 B2 | 4/2006 | Lai et al. |
| 7,066,596 B2 | 6/2006 | Ishak |
| 7,067,278 B1 * | 6/2006 | Hoech-Guldberg et al. ............ 435/69.1 |
| 7,098,283 B2 | 8/2006 | Lai |
| 7,241,312 B2 | 7/2007 | Lai et al. |
| 7,255,435 B2 | 8/2007 | Pratt |
| 7,271,298 B2 | 9/2007 | Xu et al. |
| 7,275,822 B2 | 10/2007 | Gupta et al. |
| 7,276,544 B2 | 10/2007 | Lai et al. |
| 7,278,737 B2 | 10/2007 | Mainster et al. |
| 7,279,538 B2 | 10/2007 | Lai et al. |
| 7,304,117 B2 | 12/2007 | Lai |
| 7,364,291 B2 | 4/2008 | Haywood et al. |
| 7,520,608 B2 | 4/2009 | Ishak et al. |
| 7,524,060 B2 | 4/2009 | Sanchez Ramos |
| 7,556,376 B2 | 7/2009 | Ishak et al. |
| 7,713,452 B2 | 5/2010 | Kauffman et al. |
| 7,832,903 B2 | 11/2010 | Sanchez Ramos |
| 7,914,177 B2 | 3/2011 | Sanchez Ramos |
| 8,360,574 B2 | 1/2013 | Ishak et al. |
| 2002/0042653 A1 | 4/2002 | Copeland et al. |
| 2002/159026 A1 | 10/2002 | Bernheim |
| 2003/0105130 A1 | 6/2003 | Hurley et al. |
| 2004/0014737 A1 | 1/2004 | Vincente et al. |
| 2004/0070726 A1 | 4/2004 | Ishak |
| 2004/0073277 A1 * | 4/2004 | Geronemus et al. ............ 607/88 |
| 2004/0143001 A1 * | 7/2004 | Love et al. ............ 514/410 |
| 2004/0185268 A1 | 9/2004 | Kumar et al. |
| 2004/0246437 A1 | 12/2004 | Ambler et al. |
| 2005/0043793 A1 | 2/2005 | Pratt |
| 2005/0055091 A1 | 3/2005 | Lai |
| 2005/0090428 A1 | 4/2005 | Compans et al. |
| 2005/0143812 A1 | 6/2005 | Paul et al. |
| 2005/0248752 A1 | 11/2005 | Hall |
| 2005/0254003 A1 | 11/2005 | Jani et al. |
| 2005/0273163 A1 | 12/2005 | Tran et al. |
| 2005/0283234 A1 | 12/2005 | Zhou et al. |
| 2006/0020338 A1 | 1/2006 | Lai |
| 2006/0092374 A1 | 5/2006 | Ishak |
| 2006/0099148 A1 | 5/2006 | Fisher et al. |
| 2006/0119954 A1 | 6/2006 | Casper et al. |
| 2006/0126019 A1 | 6/2006 | Liang et al. |
| 2006/0197067 A1 | 9/2006 | Xia et al. |
| 2006/0228725 A1 | 10/2006 | Salafsky |
| 2006/0235428 A1 | 10/2006 | Silvestrini |
| 2006/0241263 A1 | 10/2006 | Lai |
| 2006/0252844 A1 | 11/2006 | Mentak |
| 2007/0034833 A1 | 2/2007 | Parce et al. |
| 2007/0035240 A1 | 2/2007 | Yang et al. |
| 2007/0092831 A1 | 4/2007 | Lai et al. |
| 2007/0159594 A9 | 7/2007 | Jani et al. |
| 2007/0188701 A1 | 8/2007 | Sanchez Ramos |
| 2007/0195262 A1 | 8/2007 | Masse et al. |
| 2007/0216861 A1 | 9/2007 | Ishak et al. |
| 2007/0228587 A1 | 10/2007 | Ikari |
| 2007/0293666 A1 | 12/2007 | Minami et al. |
| 2008/0013035 A1 | 1/2008 | Yang et al. |
| 2008/0013045 A1 | 1/2008 | Mainster et al. |
| 2008/0186448 A1 | 8/2008 | Ishak et al. |
| 2008/0221674 A1 | 9/2008 | Blum et al. |
| 2008/0241951 A1 | 10/2008 | Battulga et al. |
| 2008/0291394 A1 | 11/2008 | Ishak |
| 2008/0297931 A1 | 12/2008 | Sanchez Ramos |
| 2009/0247483 A1 | 10/2009 | Mitchell et al. |
| 2009/0268157 A1 | 10/2009 | Krieg-Kowald et al. |
| 2010/0053550 A1 | 3/2010 | Giraudet |
| 2010/0060850 A1 | 3/2010 | Giraudet |
| 2010/0066974 A1 | 3/2010 | Croft et al. |
| 2010/0085534 A1 | 4/2010 | Mainster |
| 2010/0091240 A1 | 4/2010 | Drobe et al. |
| 2010/0125136 A1 | 5/2010 | Yeh et al. |
| 2011/0004330 A1 | 1/2011 | Rothkopf et al. |
| 2011/0007847 A1 | 1/2011 | O'Keeffe et al. |
| 2011/0060850 A1 | 3/2011 | Ko et al. |

FOREIGN PATENT DOCUMENTS

| | | |
|---|---|---|
| DE | 3544627 | 12/1985 |
| EP | 0763754 A2 | 3/1997 |
| JP | H08-254603 | 1/1996 |
| JP | H09-136902 | 5/1997 |
| JP | 2004-247156 | 9/2004 |
| JP | 2013-097159 | 5/2013 |
| JP | 2013-097160 | 5/2013 |
| WO | WO 88/02871 | 4/1988 |
| WO | WO 97/20246 A1 | 6/1997 |
| WO | WO 2006/077433 A1 | 7/2006 |
| WO | WO 2008/059177 | 5/2008 |
| WO | WO 2009/053502 | 4/2009 |

OTHER PUBLICATIONS

Espindle et al., "Quality-of-life improvements in cataract patients with bilateral blue light-filtering intraocular lenses: Clinical trial" J. Cataract Refract Surg., vol. 31, Oct. 2005, p. 1952-1959.

Johnson, W. & Crane, R. 1993. Introduction to Rugate Filter Technology. SPIE 2046:88-108.

Kalloniatis, M. & Luu, C. "Psychophysics of Vision" available at http://webvision.med.utah.edu/Phych1.html, last visited Jan. 29, 2008.

Leibovitch et al., "Visual outcomes with the yellow intraocular lens" ACTA Opthalmologica Scandinavica 2006, 84: p. 95-99.

Li Qing et al., "The effect of blue light on visual function" International Review of Ophthalmology, vol. 30, No. 5, Oct. 2006, p. 336-340.

(56) References Cited

OTHER PUBLICATIONS

Infeld, K. 1998 Sunlight Poses Universal Cataract Risk. Johns Hopkins Study available at http://www.eurekalert.org/releases/jhusunposcat.html, last visited Feb. 1, 2008.
Mainster, M.A. & Sparrow, J.R. 2003. How Much Blue Light Should an IOL Transmit? British Journal of Ophthalmology 87:1523-29.
Mainster, M.A. 2005. Intraocular Lenses Should Block UV Radiation and Violet but not Blue Light. ArchOphthal 123:550.
Mainster, M.A. 2006. Violet and Blue Light Blocking Intraocular Lenses: Photoprotection vs. Photoreception. Br J Ophthalmol 90:784-92.
NACL website, as archived from Oct. 8, 2000: http://web.archive.org/web/20001008003354//www.nacl.com/custom.htm obtained for WayBack Machine at www.archive.org.
Nolan, J.M. et al. 2009. Augmentation of Macular Pigment following Implantation of Blue Light Filtering Intraocular Lenses at the Time of Cataract Surgery. Invest Opthalmol Vis Sci 50(10):4777-85.
Rodriguez-Galietero et al., "Comparison of contrast sensitivity and color discrimination after clear and yellow intraocular lens implantation" J. Cataract Refract Surg., vol. 31, Sep. 2005, p. 1736-1740.
Sparrow, J.R., et al. 2004. Blue light-absorbing intraocular lens and retinal pigment epithelium protection in vitro. J Cataract Refract Surg 30:873-78.
Ueda, T. et al. 2009. Eye damage control by reduced blue illumination, Exp. Eye. Res. 89(6):863-8.
Willard, et al. 1981. Instrumental Methods of Analysis, 6th Ed. pp. 67-68.
Wyszecki & Stiles. 1982. Color Science: Concepts and Methods, Quantitative Data and Formulae. Wiley (NY). pp. 100-107.
Mar. 12, 2015 Office Action in related Taiwanese patent application No. 100123739, 19 pages.
Samaroo et al. Efficient microwave-assisted synthesis of amine substituted pentafluorophenylporphyrin in Org Lett. Oct. 26, 2006; vol. 8(22): pp. 4985-4988. Abstract.
Office Action dated Jul. 24, 2015, in Canadian Patent Application No. 2,670,789, High Performance Optics, Inc., filed Oct. 31, 2007.
Office Action dated Jul. 24, 2015, in Indian Patent Application No. 5247/CHENP/2008, High Performance Optics, Inc., filed Sep. 30, 2008.
Office Action dated Aug. 11, 2015, in European Application No. 11804243.1, High Performance Optics, Inc., filed May 7, 2011.
Office Action dated Aug. 27, 2015, in Chinese Patent Application No. 201410641454.7, High Performance Optics, Inc., filed Mar. 25, 2010.
Search Report dated Aug. 27, 2015, for Chinese Patent Application No. 201410641454.7, High Performance Optics, Inc., filed Mar. 25, 2010.
Office Action dated Sep. 14, 2015, in Japanese Patent Application No. 2013-140659, High Performance Optics, Inc., filed Apr. 7, 2013.
International Search Report and Written Opinion dated Jul. 22, 2015, for International Application No. PCT/US 15/29073, ISA/US, Alexandria, Virginia, United States.
Office Action dated Oct. 5, 2015, in Japanese Patent Application No. 2009-501478, High Performance Optics, Inc., filed Mar. 19, 2007.
European Search Report dated Jun. 29, 2016, for European Application No. 15201564.0, EPO, Munich, Germany.
Liebmann et al., "Blue-Light Irradiation Regulates Proliferation and Differentiation in Human Skin Cells," *Journal of Investigative Dermatology*, vol. 130, Issue I, pp. 259-269, Published Online Aug. 13, 2009.
Opländer et al., "Effects of blue light irradiation on human dermal fibroblasts," *Journal of Photochemistry and Photobiology B: Biology*, vol. 103, Issue 2, pp. 118-125, Published Online Feb. 26, 2011.
Liebel et al., "Irradiation of Skin with Visible Light Induces Reactive Oxygen Species and Matrix-Degrading Enzymes," *Journal of Investigative Dermatology*, vol. 132, Issue 7, pp. 1901-1907, Published Online Feb. 9, 2012.
Magnesium tetraphenylporphyrin, [MgTPP] [online] [retrieved Jun. 30, 2017]. Retrieved from Internet, <http://om1c.org/spectra/PhotochemCAD/html/101.html>. © Jun. 2017 Scott Prahl.
European Office Action dated Apr. 20, 2017, for European Application No. 15201564.0, EPO, Munich, Germany.

\* cited by examiner

FIG. 6
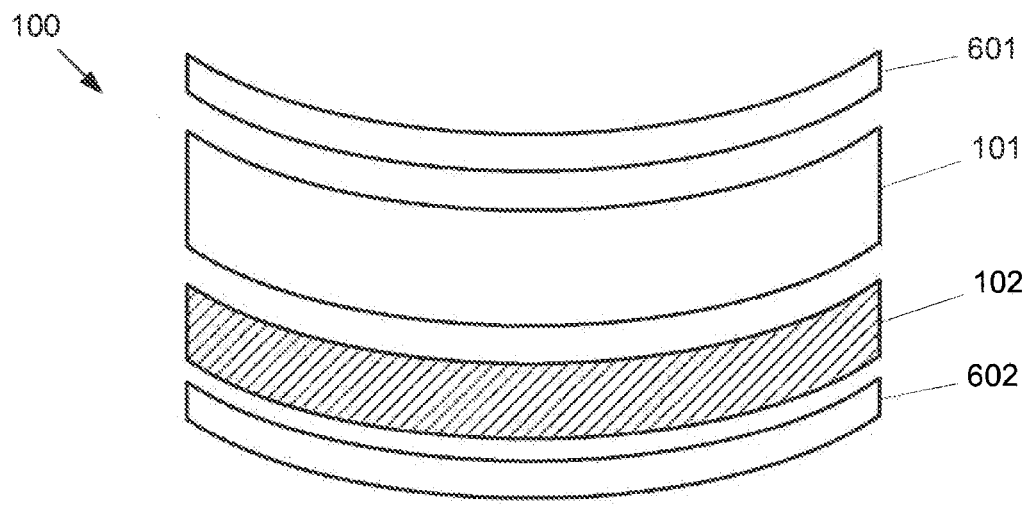
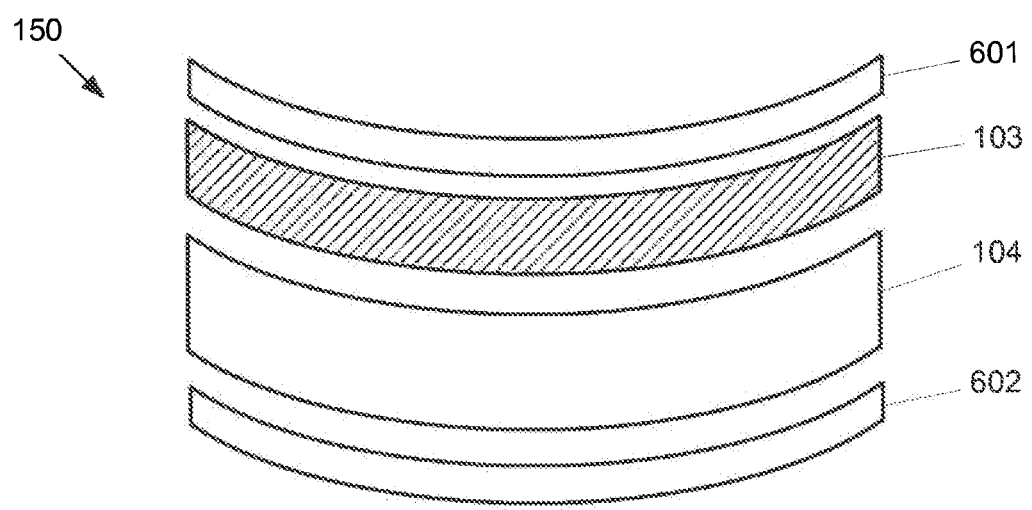

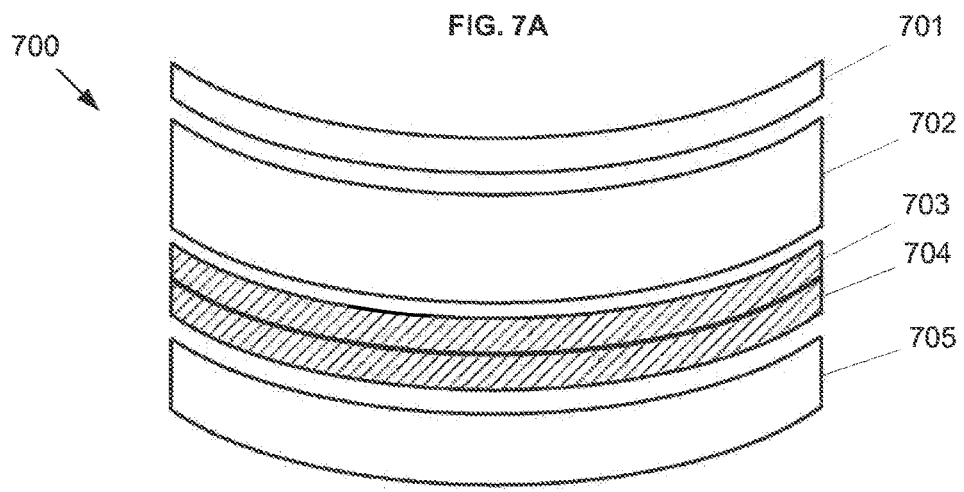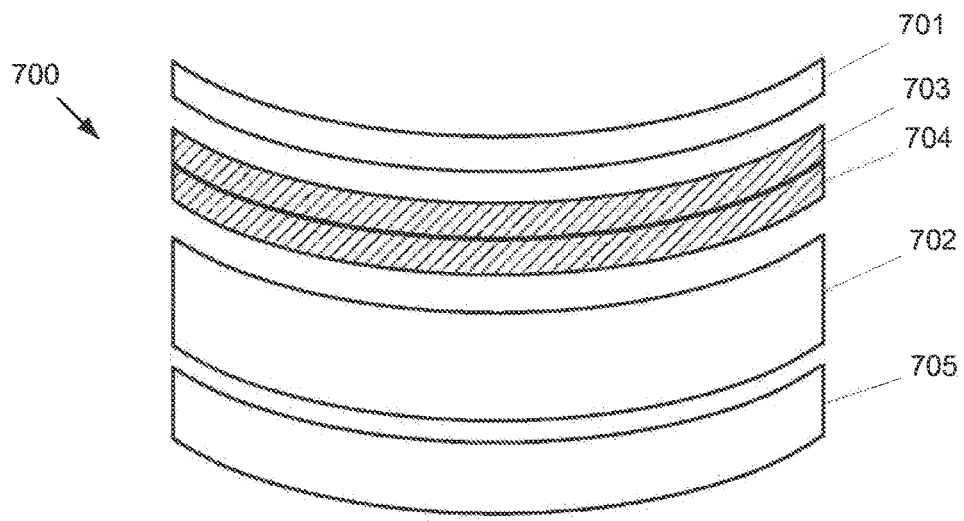

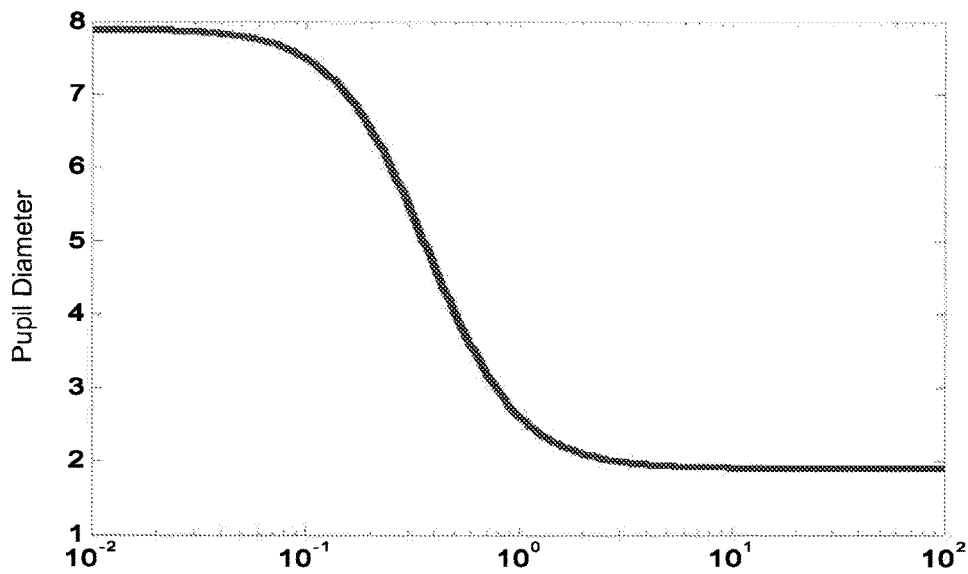
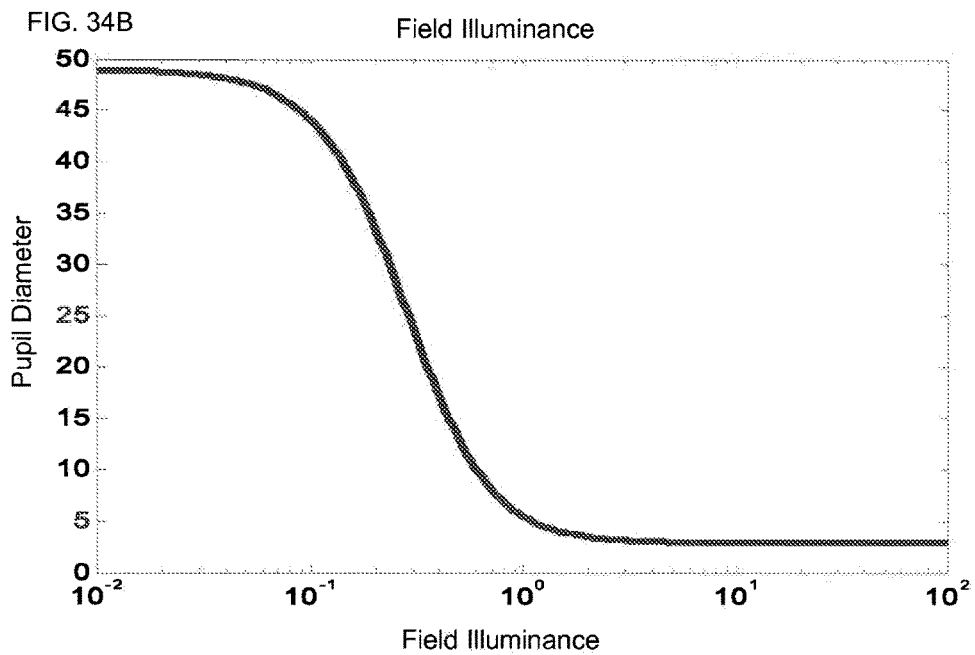

JND Shift

JND Shift

FIG. 46
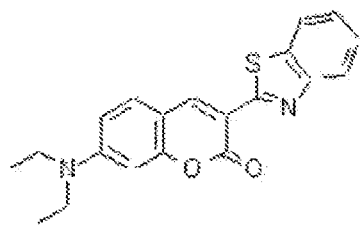
Coumarin 6
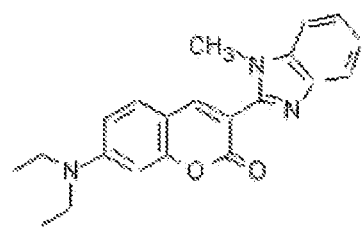
Coumarin 30
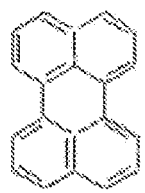
Perylene
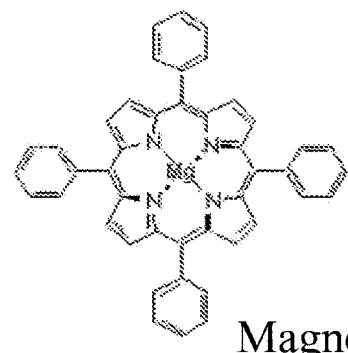
Magnesium Tetraphenyl Porphyrin
Yellow Orange
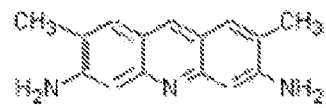
Acridyne Acridyne

HIGH ENERGY VISIBLE LIGHT FILTER SYSTEMS WITH YELLOWNESS INDEX VALUES

CROSS-REFERENCES TO RELATED APPLICATIONS

This application claims priority to U.S. patent application Ser. No. 13/174,998 filed on Jul. 1, 2011. U.S. patent application Ser. No. 13/174,998 claims priority to U.S. Provisional Application No. 61/361,677, filed Jul. 6, 2010. U.S. patent application Ser. No. 13/174,998 is also a continuation-in-part of U.S. application Ser. No. 11/933,069 filed on Oct. 31, 2007, which claims priority to U.S. patent application Ser. No. 11/761,892 filed Jun. 12, 2007, which is a continuation-in-part of U.S. patent application Ser. No. 11/378,317 filed Mar. 20, 2006 and which claims priority to U.S. Provisional Application No. 60/812,628 filed Jun. 12, 2006. application Ser. No. 11/933,069 is also a continuation-in-part of U.S. patent application Ser. No. 11/892,460 filed Aug. 23, 2007, which claims priority to U.S. Provisional Application No. 60/839,432 filed Aug. 23, 2006, U.S. Provisional Application No. 60/841,502 filed Sep. 1, 2006, and U.S. Provisional Application No. 60/861,247 filed Nov. 28, 2006. application Ser. No. 11/933,069 also claims priority to U.S. Provisional Application No. 60/978,175 filed Oct. 8, 2007. U.S. application Ser. No. 13/174,998 also claims priority to U.S. Provisional Application No. 61/440,941 filed on Feb. 9, 2011; U.S. Provisional Application No. 61/415,890 filed on Nov. 22, 2010; and U.S. Provisional Application No. 61/377,603 filed on Aug. 27, 2010. All of these applications are incorporated by reference in their entireties.

BACKGROUND OF THE INVENTION

Electromagnetic radiation from the sun continuously bombards the Earth's atmosphere. Light is made up of electromagnetic radiation that travels in waves. The electromagnetic spectrum includes radio waves, millimeter waves, microwaves, infrared, visible light, ultra-violet (UVA and UVB), x-rays, and gamma rays. The visible light spectrum includes the longest visible light wavelength of approximately 700 nm and the shortest of approximately 400 nm (nanometers or $10^{-9}$ meters). Blue light wavelengths fall in the approximate range of 400 nm to 500 nm. For the ultra-violet bands, UVB wavelengths are from 290 nm to 320 nm, and UVA wavelengths are from 320 nm to 400 nm. Gamma and x-rays make up the higher frequencies of this spectrum and are absorbed by the atmosphere. The wavelength spectrum of ultraviolet radiation (UVR) is 100-400 nm. Most UVR wavelengths are absorbed by the atmosphere, except where there are areas of stratospheric ozone depletion. Over the last 20 years, there has been documented depletion of the ozone layer primarily due to industrial pollution. Increased exposure to UVR has broad public health implications as an increased burden of UVR ocular and skin disease is to be expected.

The ozone layer absorbs wavelengths up to 286 nm, thus shielding living beings from exposure to radiation with the highest energy. However, we are exposed to wavelengths above 286 nm, most of which falls within the human visual spectrum (400-700 nm). The human retina responds only to the visible light portion of the electromagnetic spectrum. The shorter wavelengths pose the greatest hazard because they inversely contain more energy. Blue light has been shown to be the portion of the visible spectrum that produces the most photochemical damage to animal retinal pigment epithelium (RPE) cells. Exposure to these wavelengths has been called the blue light hazard because these wavelengths are perceived as blue by the human eye.

Cataracts and macular degeneration are widely thought to result from photochemical damage to the intraocular lens and retina, respectively. Blue light exposure has also been shown to accelerate proliferation of uveal melanoma cells. The most energetic photons in the visible spectrum have wavelengths between 380 and 500 nm and are perceived as violet or blue. The wavelength dependence of phototoxicity summed over all mechanisms is often represented as an action spectrum, such as is described in Mainster and Sparrow, "How Much Blue Light Should an IOL Transmit?" Br. J. Ophthalmol., 2003, v. 87, pp. 1523-29 and FIG. 6. In eyes without an intraocular lens (aphakic eyes), light with wavelengths shorter than 400 nm can cause damage. In phakic eyes, this light is absorbed by the intraocular lens and therefore does not contribute to retinal phototoxicity; however it can cause optical degradation of the lens or cataracts.

The pupil of the eye responds to the photopic retinal illuminance, in trolands (a unit of conventional retinal illuminance; a method for correcting photometric measurements of luminance values impinging on the human eye by scaling them by the effective pupil size), which is the product of the incident flux with the wavelength-dependent sensitivity of the retina and the projected area of the pupil. This sensitivity is described in Wyszecki and Stiles, *Color Science: Concepts and Methods, Quantitative Data and Formulae* (Wiley: New York) 1982, esp. pages 102-107.

Current research strongly supports the premise that short wavelength visible light (blue light) having a wavelength of approximately 400-500 nm could be a contributing cause of AMD (age related macular degeneration). It is believed that the highest level of blue light absorption occurs in a region around 430 nm, such as 400-460 nm. Research further suggests that blue light worsens other causative factors in AMD, such as heredity, tobacco smoke, and excessive alcohol consumption.

The human retina includes multiple layers. These layers listed in order from the first exposed to any light entering the eye to the deepest include:
1) Nerve Fiber Layer
2) Ganglion Cells
3) Inner Plexiform Layer
4) Bipolar and Horizontal Cells
5) Outer Plexiform Layer
6) Photoreceptors (Rods and Cones)
7) Retinal Pigment Epithelium (RPE)
8) Bruch's Membrane
9) Choroid When light is absorbed by the eye's photoreceptor cells, (rods and cones) the cells bleach and become unreceptive until they recover. This recovery process is a metabolic process and is called the "visual cycle." Absorption of blue light has been shown to reverse this process prematurely. This premature reversal increases the risk of oxidative damage and is believed to lead to the buildup of the pigment lipofuscin in the retina. This build up occurs in the retinal pigment epithelium (RPE) layer. It is believed that aggregates of extra-cellular materials called drusen are formed due to the excessive amounts of lipofuscin.

Current research indicates that over the course of one's life, beginning with that of an infant, metabolic waste byproducts accumulate within the pigment epithelium layer of the retina, due to light interactions with the retina. This metabolic waste product is characterized by certain fluorophores, one of the most prominent being lipofuscin constituent A2E. In vitro studies by Sparrow indicate that lipofuscin chromophore A2E found within the RPE is maximally excited by 430 nm light. It is theorized that a tipping point is reached when a combination of a build-up of this metabolic waste (specifically the lipofuscin fluorophore) has achieved a certain level of accumulation, the human body's physiological ability to metabolize within the retina certain of this waste has diminished as one reaches a certain age threshold, and a blue light stimulus of the proper wavelength causes drusen to be formed in the RPE layer. It is believed that the drusen then further interfere with the normal physiology/metabolic activity which allows for the proper nutrients to get to the photoreceptors thus contributing to age-related macular degeneration (AMD). AMD is the leading cause of irreversible severe visual acuity loss in the United States and Western World. The burden of AMD is expected to increase dramatically in the next 20 years because of the projected shift in population and the overall increase in the number of ageing individuals.

Drusen hinder or block the RPE layer from providing the proper nutrients to the photoreceptors, which leads to damage or even death of these cells. To further complicate this process, it appears that when lipofuscin absorbs blue light in high quantities it becomes toxic, causing further damage and/or death of the RPE cells. It is believed that the lipofuscin constituent A2E is at least partly responsible for the short wavelength sensitivity of RPE cells. A2E has been shown to be maximally excited by blue light; the photochemical events resulting from such excitation can lead to cell death. See, for example, Janet R. Sparrow et al., "Blue light-absorbing intraocular lens and retinal pigment epithelium protection in vitro," J. Cataract Refract. Surg. 2004, vol. 30, pp. 873-78.

From a theoretical perspective, the following appears to take place:
1) Waste buildup occurs within the pigment epithelial level starting from infancy throughout life.
2) Retinal metabolic activity and ability to deal with this waste typically diminish with age.
3) The macula pigment typically decreases as one ages, thus filtering out less blue light.
4) Blue light causes the lipofuscin to become toxic. The resulting toxicity damages pigment epithelial cells.

The lighting and vision care industries have standards as to human vision exposure to UVA and UVB radiation. Surprisingly, no such standard is in place with regard to blue light. For example, in the common fluorescent tubes available today, the glass envelope mostly blocks ultra-violet light but blue light is transmitted with little attenuation. In some cases, the envelope is designed to have enhanced transmission in the blue region of the spectrum. Such artificial sources of light hazard may also cause eye damage.

Laboratory evidence by Sparrow at Columbia University has shown that if about 50% of the blue light within the wavelength range of 430±30 nm is blocked, RPE cell death caused by the blue light may be reduced by up to 80%. External eyewear such as sunglasses, spectacles, goggles, and contact lenses that block blue light in an attempt to improve eye health are disclosed, for example, in U.S. Pat. No. 6,955,430 to Pratt. Other ophthalmic devices whose object is to protect the retina from this phototoxic light include intraocular and contact lenses. These ophthalmic devices are positioned in the optical path between environmental light and the retina and generally contain or are coated with dyes that selectively absorb blue and violet light.

Other lenses are known that attempt to decrease chromatic aberration by blocking blue light. Chromatic aberration is caused by optical dispersion of ocular media including the cornea, intraocular lens, aqueous humour, and vitreous humour. This dispersion focuses blue light at a different image plane than light at longer wavelengths, leading to defocus of the full color image. Conventional blue blocking lenses are described in U.S. Pat. No. 6,158,862 to Patel et al., U.S. Pat. No. 5,662,707 to Jinkerson, U.S. Pat. No. 5,400,175 to Johansen, and U.S. Pat. No. 4,878,748 to Johansen.

Conventional methods for reducing blue light exposure of ocular media typically completely occlude light below a threshold wavelength, while also reducing light exposure at longer wavelengths. For example, the lenses described in U.S. Pat. No. 6,955,430 to Pratt transmit less than 40% of the incident light at wavelengths as long as 650 nm, as shown in FIG. 6 of Pratt '430. The blue-light blocking lens disclosed by Johansen and Diffendaffer in U.S. Pat. No. 5,400,175 similarly attenuates light by more than 60% throughout the visible spectrum, as illustrated in FIG. 3 of the '175 patent.

Balancing the range and amount of blocked blue light may be difficult, as blocking and/or inhibiting blue light affects color balance, color vision if one looks through the optical device, and the color in which the optical device is perceived. For example, shooting glasses appear bright yellow and block blue light. The shooting glasses often cause certain colors to become more apparent when one is looking into a blue sky, allowing for the shooter to see the object being targeted sooner and more accurately. While this works well for shooting glasses, it would be unacceptable for many ophthalmic applications. In particular, such ophthalmic systems may be cosmetically unappealing because of a yellow or amber tint that is produced in lenses by blue blocking More specifically, one common technique for blue blocking involves tinting or dyeing lenses with a blue blocking tint, such as BPI Filter Vision 450 or BPI Diamond Dye 500. The tinting may be accomplished, for example, by immersing the lens in a heated tint pot containing a blue blocking dye solution for some predetermined period of time. Typically, the solution has a yellow or amber color and thus imparts a yellow or amber tint to the lens. To many people, the appearance of this yellow or amber tint may be undesirable cosmetically. Moreover, the tint may interfere with the normal color perception of a lens user, making it difficult, for example, to correctly perceive the color of a traffic light or sign.

Efforts have been made to compensate for the yellowing effect of conventional blue blocking filters. For example, blue blocking lenses have been treated with additional dyes, such as blue, red or green dyes, to offset the yellowing effect. The treatment causes the additional dyes to become intermixed with the original blue blocking dyes. However, while this technique may reduce yellow in a blue blocked lens, intermixing of the dyes may reduce the effectiveness of the blue blocking by allowing more of the blue light spectrum through. Moreover, these conventional techniques undesirably reduce the overall transmission of light wavelengths other than blue light wavelengths. This unwanted reduction may in turn result in reduced visual acuity for a lens user.

It has been found that conventional blue-blocking reduces visible transmission, which in turn stimulates dilation of the pupil. Dilation of the pupil increases the flux of light to the internal eye structures including the intraocular lens and retina. Since the radiant flux to these structures increases as the square of the pupil diameter, a lens that blocks half of the blue light but, with reduced visible transmission, relaxes the pupil from 2 mm to 3 mm diameter will actually increase the dose of blue photons to the retina by 12.5%. Protection of the retina from phototoxic light depends on the amount of this light that impinges on the retina, which depends on the transmission properties of the ocular media and also on the dynamic aperture of the pupil. Previous work to date has been silent on the contribution of the pupil to prophylaxis of phototoxic blue light.

Another problem with conventional blue-blocking is that it can degrade night vision. Blue light is more important for low-light level or scotopic vision than for bright light or photopic vision, a result which is expressed quantitatively in the luminous sensitivity spectra for scotopic and photopic vision. Photochemical and oxidative reactions cause the absorption of 400 to 450 nm light by intraocular lens tissue to increase naturally with age. Although the number of rod photoreceptors on the retina that are responsible for low-light vision also decreases with age, the increased absorption by the intraocular lens is important to degrading night vision. For example, scotopic visual sensitivity is reduced by 33% in a 53 year-old intraocular lens and 75% in a 75 year-old lens. The tension between retinal protection and scotopic sensitivity is further described in Mainster and Sparrow, "How Much Light Should and IOL Transmit?" Br. J. Ophthalmol., 2003, v. 87, pp. 1523-29.

Conventional approaches to blue blocking also may include cutoff or high-pass filters to reduce the transmission below a specified blue or violet wavelength to zero. For example, all light below a threshold wavelength may be blocked completely or almost completely. For example, U.S. Pub. Patent Application No. 2005/0243272 to Mainster and Mainster, "Intraocular Lenses Should Block UV Radiation and Violet but not Blue Light," Arch. Ophthal., v. 123, p. 550 (2005) describe the blocking of all light below a threshold wavelength between 400 and 450 nm. Such blocking may be undesirable, since as the edge of the long-pass filter is shifted to longer wavelengths, dilation of the pupil acts to increase the total flux. As previously described, this can degrade scotopic sensitivity and increase color distortion.

Recently there has been debate in the field of intraocular lenses (IOLs) regarding appropriate UV and blue light blocking while maintaining acceptable photopic vision, scotopic vision, color vision, and circadian rhythms.

In view of the foregoing, there is a need for an ophthalmic system that can provide one or more of the following:

1) Blue blocking with an acceptable level of blue light protection
2) Acceptable color cosmetics, i.e., it is perceived as mostly color neutral by someone observing the ophthalmic system when worn by a wearer.
3) Acceptable color perception for a user. In particular, there is a need for an ophthalmic system that will not impair the wearer's color vision and further that reflections from the back surface of the system into the eye of the wearer be at a level of not being objectionable to the wearer.
4) Acceptable level of light transmission for wavelengths other than blue light wavelengths. In particular, there is a need for an ophthalmic system that allows for selective blockage of wavelengths of blue light while at the same time transmitting in excess of 80% of visible light.
5) Acceptable photopic vision, scotopic vision, color vision, and/or circadian rhythms.

In order to provide this optimal ophthalmic system it is desirable to include standardized Yellowness Index ranges, whereby the upper end of said range closely borders a cosmetically unacceptable yellow color.

This need exists as more and more data is pointing to blue light as one of the possible contributory factors in macular degeneration (the leading cause of blindness in the industrialized world) and other retinal diseases such as uveal melanoma referenced in entirety in "The Effect of Blue Light Exposure in an Ocular Melanoma Animal Model" J Exp Clin Cancer Res. 2009; 28(1): 48.

BRIEF SUMMARY OF THE INVENTION

An ophthalmic lens is provided specifically adapted through use of a dye to selectively inhibit transmission of visible light between 450±50 nm, wherein the lens has a yellowness index not more than 35.0.

It is further provided a lens as described above that inhibits at least 5%, preferably at least 10%, more preferably at least 20%, more preferably at least 30%, or more preferably at least 40% of light having a wavelength of X±15 nm of light having a wavelength of X±15 nm, where X is a wavelength in the range of 415-485 nm.

Also provided is a lens as described above that selectively inhibits transmission of at least two different ranges of wavelengths selected from the range of 450±50 nm.

A lens as described above is provided that blocks at least 5%, preferably at least 10%, more preferably at least 20%, more preferably at least 30%, or more preferably at least 40% of light having a wavelength of X1±15 nm, and at least 40% of the light having a wavelength of X2±15 nm, where X1 is a wavelength in the range of 415-485 nm and X2 is a wavelength different from X1 and in the range of 415-485 nm.

A lens as described above is provided that transmits at least 80% of all light wavelengths in the range of 400-500 nm, except light wavelengths at X1±15 nm and X2±15 nm, where X1 is a wavelength in the range of 415-485 nm and X2 is a wavelength different from X1 and in the range of 415-485 nm.

It is further provided a lens as described above where the lens is a contact lens. The contact lens may have a yellowness index of not more than 27.5 or more preferably not more than 20.0

A lens as described above is provided where the lens is a contact lens and blocks at least 5%, preferably at least 10%, more preferably at least 20%, more preferably at least 30% or more preferably at least 40% of light having a wavelength of X±15 nm of light having a wavelength of 450±50 nm, while having a luminous transmission of at least 80%.

A lens as described above is provided where the lens is a contact lens and selectively inhibits visible light between 430±30 nm. This contact lens may also block at least 5%, preferably at least 10%, more preferably at least 20%, more preferably at least 30%, more preferably at least 40%, or more preferably at least 50% of light having a wavelength of X±15 nm % of light having a wavelength of 430±30 nm, while having a luminous transmission of at least 80%.

A lens as described above is provided where the lens is a contact lens and selectively inhibits visible light between 435±20 nm.

A lens as described above is provided where the lens is a spectacle lens and has a yellowness index not more than 15.0 or preferably not more than 12.5 or more preferably not more than 10.0.

A lens as described above is provided where the lens is a spectacle lens and blocks at least 5%, preferably at least 10%, more preferably at least 20%, more preferably at least 30%, or more preferably at least 40% % of light having a wavelength of 450±50 nm, while having a luminous transmission of at least 80%.

A lens as described above is provided where the lens is a spectacle lens and selectively inhibits visible light between 430±30 nm. This spectacle lens may also block at least 5%, preferably at least 10%, more preferably at least 20%, more preferably at least 30%, more preferably at least 40%, or more preferably at least 50% of light having a wavelength of 430±30 nm, while having a luminous transmission of at least 80%.

A lens as described above is provided where the lens is a spectacle lens and selectively inhibits visible light between 435±20 nm.

A lens as described above is provided where the lens is an intraocular lens. The contact lens may have a yellowness index of not more than 35.0 or preferably not more than 23.0 or more preferably not more than 15.0.

A lens as described above is provided where the lens is an intraocular lens and blocks at least 5%, preferably at least 10%, more preferably at least 20%, more preferably at least 30%, or more preferably at least 40% of light having a wavelength of 450±50 nm, while having a luminous transmission of at least 80%.

A lens as described above is provided where the lens is an intraocular lens and selectively inhibits visible light between 430±30 nm. This an intraocular may also block at least 5%, preferably at least 10%, more preferably at least 20%, more preferably at least 30%, more preferably at least 40%, or more preferably at least 50% of light having a wavelength of 430±30 nm, while having a luminous transmission of at least 80%.

A lens as described above is provided where the lens is an intraocular lens and selectively inhibits visible light between 435±20 nm.

A lens as described above is provided that may also selectively inhibit transmission of light within the UV wavelength range.

A lens as described above is provided where the lens contains a dye that causes the lens to selectively inhibit transmission of visible light between 450±50 nm. The dye may be selected from the following: bilirubin; chlorophyll a, diethyl ether; chlorophyll a, methanol; chlorophyll b; diprotonated-tetraphenylporphyrin; hematin; magnesium octaethylporphyrin; magnesium octaethylporphyrin (MgOEP); magnesium phthalocyanine (MgPc), PrOH; magnesium phthalocyanine (MgPc), pyridine; magnesium tetramesitylporphyrin (MgTMP); magnesium tetraphenylporphyrin (MgTPP); octaethylporphyrin; phthalocyanine (Pc); porphin; tetra-t-butylazaporphine; tetra-t-butylnaphthalocyanine; tetrakis(2,6-dichlorphenyl)porphyrin; tetrakis(o-aminophenyl)porphyrin; tetramesitylporphyrin (TMP); tetraphenylporphyrin (TPP); vitamin B12; zinc octaethylporphyrin (ZnOEP); zinc phthalocyanine (ZnPc), pyridine; zinc tetramesitylporphyrin (ZnTMP); zinc tetramesitylporphyrin radical cation; zinc tetraphenylporphyrin (ZnTPP); perylene and derivatives thereof.

A lens as described above is provided where the lens contains a dye where the dye is perylene or magnesium tetramesitylporphyrin (MgTMP) or magnesium tetraphenylporphyrin (MgTPP).

A non-ophthalmic material is provided specifically adapted to selectively inhibit transmission of visible light between 450±50 nm, wherein the lens has a yellowness index not more than 35.0.

A non-ophthalmic material as described above is provided that blocks at least 5%, preferably at least 10%, more preferably at least 20%, more preferably at least 30%, or more preferably at least 40% of light having a wavelength of 450±50 nm, while having a luminous transmission of at least 80%.

A non-ophthalmic material as described above is provided that selectively inhibits visible light between 430±30 nm.

A non-ophthalmic material as described above is provided that selectively inhibits visible light between 435±20 nm.

A non-ophthalmic material as described above is provided where the yellowness index is not more than 23.0 or preferably not more than 15.0.

BRIEF DESCRIPTION OF THE DRAWINGS

FIG. 6 illustrates exemplary ophthalmic systems using anti-reflective coatings.

FIG. 7A illustrates an exemplary combination of a blue blocking component, a color balancing component, and an ophthalmic component.

FIG. 7B illustrates another exemplary combination of a blue blocking component, a color balancing component, and an ophthalmic component.

FIG. 34A shows pupil diameter as a function of field illuminance.

FIG. 34B shows pupil area as a function of field illuminance.

FIG. 46 shows exemplary dyes.

DETAILED DESCRIPTION OF THE INVENTION

Figure 1A:
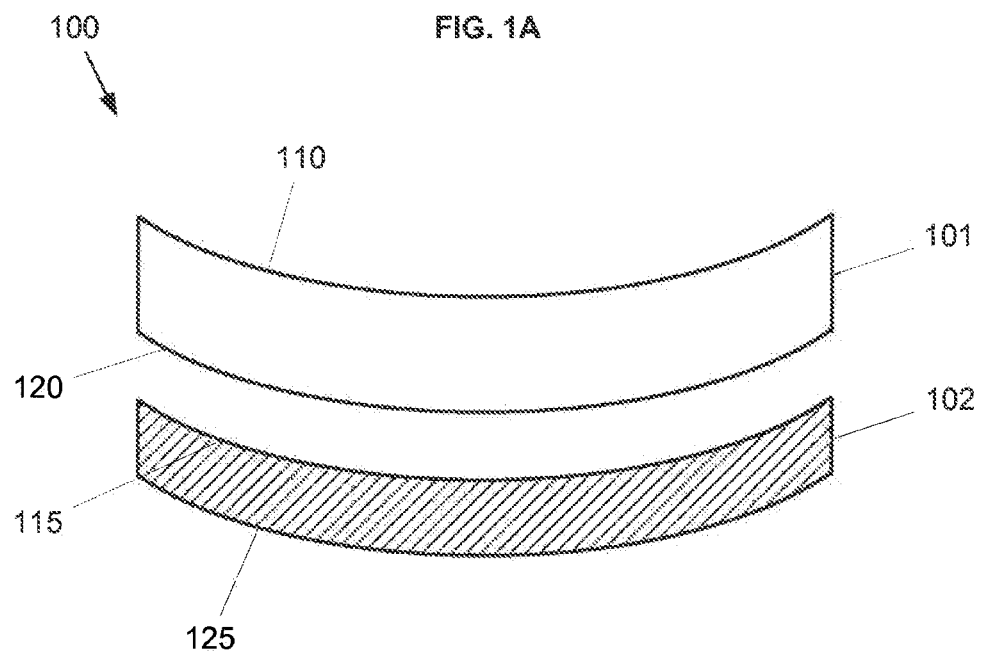
FIG. 1A shows an example of an ophthalmic system including a posterior blue blocking component and an anterior color balancing component.

Embodiments of the present invention relate to an ophthalmic system that performs effective blue blocking while at the same time providing a cosmetically attractive product, normal or acceptable color perception for a user, and a high level of transmitted light for good visual acuity. An ophthalmic system is provided that can provide an average transmission of 80% or better transmission of visible light, inhibit selective wavelengths of blue light ("blue blocking"), allow for the wearer's proper color vision performance, and provide a mostly color neutral appearance to an observer looking at the wearer wearing such a lens or lens system. As used herein, the "average transmission" of a system refers to the average transmission at wavelengths in a range, such as the visible spectrum. A system also may be characterized by the "luminous transmission" of the system, which refers to an average in a wavelength range, that is weighted according to the sensitivity of the eye at each wavelength. Systems described herein may use various optical coatings, films, materials, and absorbing dyes to produce the desired effect.

More specifically, embodiments of the invention may provide effective blue blocking in combination with color balancing. "Color balancing" or "color balanced" as used herein means that the yellow or amber color, or other unwanted effect of blue blocking is reduced, offset, neutralized or otherwise compensated for so as to produce a cosmetically acceptable result, without at the same time reducing the effectiveness of the blue blocking. For example, wavelengths at or near 400-460 nm may be blocked or reduced in intensity. •In particular, for example, wavelengths at or near 420-440 nm may be blocked or reduced in intensity. Furthermore, transmission of unblocked wavelengths may remain at a high level, for example at least 80%. Additionally, to an external viewer, the ophthalmic system may look clear or mostly clear. For a system user, color perception may be normal or acceptable.

An "ophthalmic system" as used here includes prescription or non-prescription ophthalmic lenses used, e.g., for clear or tinted glasses (or spectacles), sunglasses, contact lenses with and without visibility and/or cosmetic tinting, intra-ocular lenses (IOLs), corneal grafts, corneal inlays, corneal on-lays, and electro-active ophthalmic devices and may be treated or processed or combined with other components to provide desired functionalities described in further detail herein. Embodiments of the invention can be formulated so as to allow being applied directly into corneal tissue.

As used herein, an "ophthalmic material" is one commonly used to fabricate an ophthalmic system, such as a corrective lens. Exemplary ophthalmic materials include glass, plastics such as CR-39, Trivex, and polycarbonate materials, though other materials may be used and are known for various ophthalmic systems.

An ophthalmic system may include a blue blocking component posterior to a color-balancing component. Either of the blue blocking component or the color balancing component may be, or form part of, an ophthalmic component such as a lens. The posterior blue blocking component and anterior color balancing component may be distinct layers on or adjacent to or near a surface or surfaces of an ophthalmic lens. The color-balancing component may reduce or neutralize a yellow or amber tint of the posterior blue blocking component, to produce a cosmetically acceptable appearance. For example, to an external viewer, the ophthalmic system may look clear or mostly clear. For a system user, color perception may be normal or acceptable. Further, because the blue blocking and color balancing tints are not intermixed, wavelengths in the blue light spectrum may be blocked or reduced in intensity and the transmitted intensity of incident light in the ophthalmic system may be at least 80% for unblocked wavelengths.

As discussed previously, techniques for blue blocking are known. The known techniques to block blue light wavelengths include absorption, reflection, interference or any combination thereof. As discussed earlier, according to one technique, a lens may be tinted/dyed with a blue blocking tint, such as BPI Filter Vision 450 or BPI Diamond Dye 500, in a suitable proportion or concentration. The tinting may be accomplished, for example, by immersing the lens in a heated tint pot containing a blue blocking dye solution for some predetermined period of time. According to another technique, a filter is used for blue blocking. The filter could include, for example, organic or inorganic compounds exhibiting absorption and/or reflection of and/or interference with blue light wavelengths. The filter could comprise multiple thin layers or coatings of organic and/or inorganic substances. Each layer may have properties, which, either individually or in combination with other layers, absorbs, reflects or interferes with light having blue light wavelengths. Rugate notch filters are one example of blue blocking filters. Rugate filters are single thin films of inorganic dielectrics in which the refractive index oscillates continuously between high and low values. Fabricated by the co-deposition of two materials of different refractive index (e.g. SiO2 and TiO2), rugate filters are known to have very well defined stop-bands for wavelength blocking, with very little attenuation outside the band. The construction parameters of the filter (oscillation period, refractive index modulation, number of refractive index oscillations) determine the performance parameters of the filter (center of the stop-band, width of the stop band, transmission within the band). Rugate filters are disclosed in more detail in, for example, U.S. Pat. Nos. 6,984,038 and 7,066,596, each of which is by reference in its entirety. Another technique for blue blocking is the use of multi-layer dielectric stacks. Multi-layer dielectric stacks are fabricated by depositing discrete layers of alternating high and low refractive index materials. Similarly to rugate filters, design parameters such as individual layer thickness, individual layer refractive index, and number of layer repetitions determine the performance parameters for multi-layer dielectric stacks.

Color balancing may comprise imparting, for example, a suitable proportion or concentration of blue tinting/dye, or a suitable combination of red and green tinting/dyes to the color-balancing component, such that when viewed by an external observer, the ophthalmic system as a whole has a cosmetically acceptable appearance. For example, the ophthalmic system as a whole may look clear r mostly clear.

FIG. 1A shows an ophthalmic system including a posterior blue blocking component 101 and an anterior color balancing component 102. Each component has a concave posterior side or surface 110, 115 and a convex anterior side or surface 120, 125. In system 100, the posterior blue blocking component 101 may be or include an ophthalmic component, such as a single vision lens, wafer or optical pre-form. The single vision lens, wafer or optical pre-form may be tinted or dyed to perform blue blocking. The anterior color balancing component 102 may comprise a surface cast layer, applied to the single vision lens, wafer or optical pre-form according to known techniques. For example, the surface cast layer may be affixed or bonded to the single vision lens, wafer or optical pre-form using visible or UV light, or a combination of the two.

The surface cast layer may be formed on the convex side of the single vision lens, wafer or optical pre-form. Since the single vision lens, wafer or optical pre-form has been tinted or dyed to perform blue blocking, it may have a yellow or amber color that is undesirable cosmetically. Accordingly, the surface cast layer may, for example, be tinted with a suitable proportion of blue tinting/dye, or a suitable combination of red and green tinting/dyes.

Figure 2:
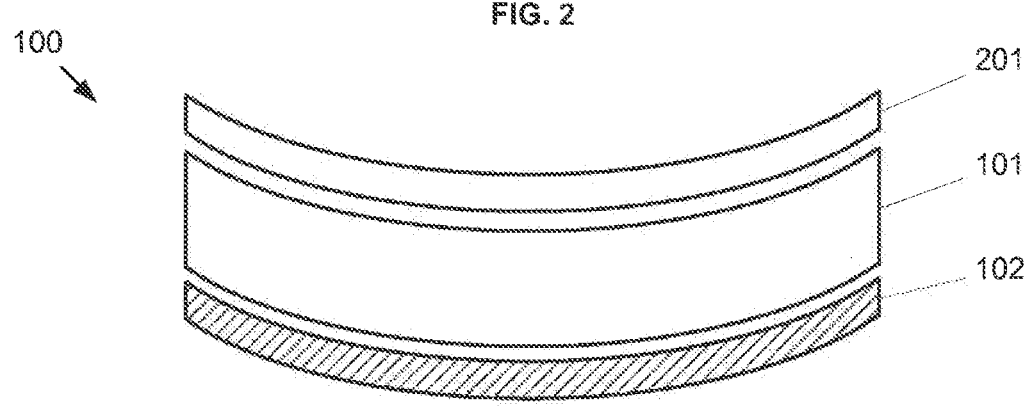
FIG. 2 shows an example of using a dye resist to form an ophthalmic system.

The surface cast layer may be treated with color balancing additives after it is applied to the single vision lens, wafer or optical pre-form that has already been processed to make it blue blocking. For example, the blue blocking single vision lens, wafer or optical pre-form with the surface cast layer on its convex surface may be immersed in a heated tint pot which has the appropriate proportions and concentrations of color balancing dyes in a solution. The surface cast layer will take up the color balancing dyes from the solution. To prevent the blue blocking single vision lens, wafer or optical pre-form from absorbing any of the color balancing dyes, its concave surface may be masked or sealed off with a dye resist, e.g. tape or wax or other coating. This is illustrated in FIG. 2, which shows an ophthalmic system 100 with a dye resist 201 on the concave surface of the single vision lens, wafer or optical pre-form 101. The edges of the single vision lens, wafer or optical pre-form may be left uncoated to allow them to become cosmetically color adjusted. This may be preferable for negative focal lenses having thick edges.

Figure 1B:
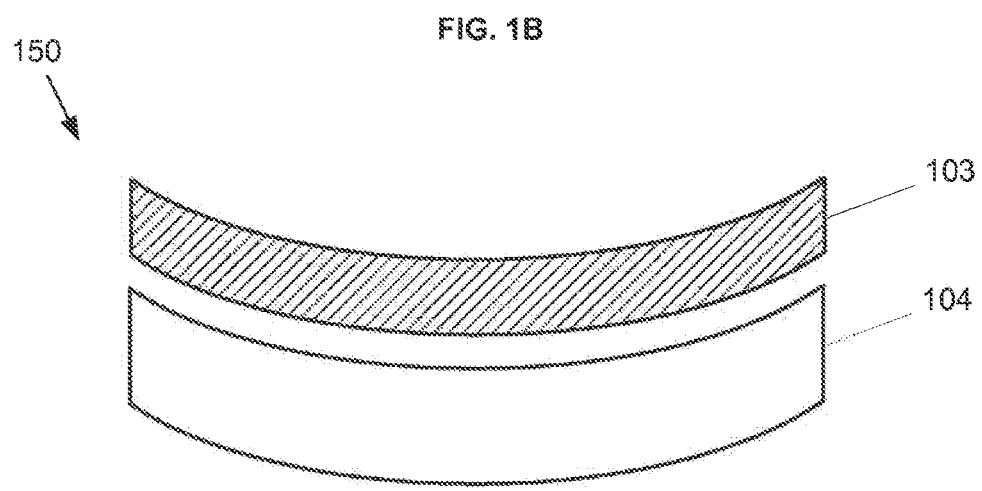
FIG. 1B shows another example of an ophthalmic system including a posterior blue blocking component and an anterior color balancing component.

FIG. 1B shows another ophthalmic system 150 in which the anterior color-balancing component 104 may be or include an ophthalmic component, such as a single vision or multi-focal lens, wafer or optical pre-form. The posterior blue blocking component 103 may be a surface cast layer. To make this combination, the convex surface of the color balancing single vision lens, wafer or optical pre-form may be masked with a dye resist as described above, to prevent it taking up blue blocking dyes when the combination is immersed in a heated tint pot containing a blue blocking dye solution. Meanwhile, the exposed surface cast layer will take up the blue blocking dyes.

It should be understood that the surface cast layer could be used in combination with a multi-focal, rather than a single vision, lens, wafer or optical pre-form. In addition, the surface cast layer could be used to add power to a single vision lens, wafer or optical pre-form, including multi-focal power, thus converting the single vision lens, wafer or optical perform to a multi-focal lens, with either a lined or progressive type addition. Of course, the surface cast layer could also be designed to add little or no power to the single vision lens, wafer or optical pre-form.

Figure 3:
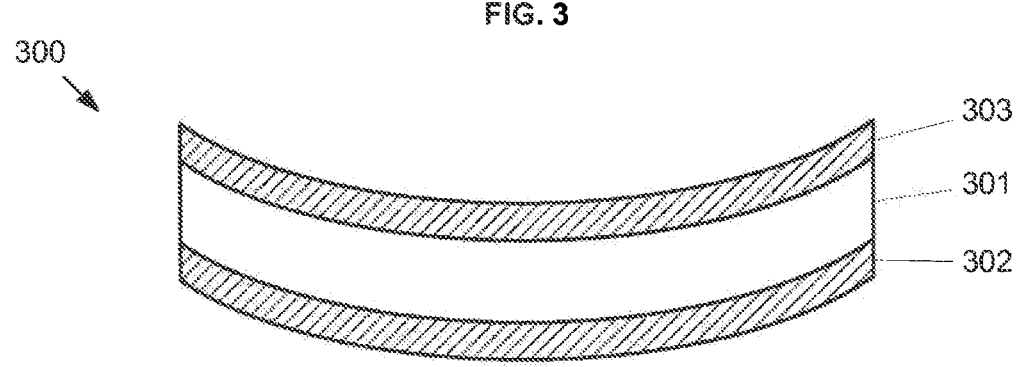
FIG. 3 illustrates an exemplary system with a blue blocking component and a color balancing component integrated into a clear or mostly clear ophthalmic lens.

FIG. 3 shows blue blocking and color balancing functionality integrated into an ophthalmic component. More specifically, in ophthalmic lens 300, a portion 303 corresponding to a depth of tint penetration into an otherwise clear or mostly clear ophthalmic component 301 at a posterior region thereof may be blue blocking. Further, a portion 302, corresponding to a depth of tint penetration into the otherwise clear or mostly clear ophthalmic component 301 at a frontal or anterior region thereof may be color balancing. The system illustrated in FIG. 3 may be produced as follows. The ophthalmic component 301 may, for example, initially be a clear or mostly clear single vision or multi-focal lens, wafer or optical pre-form. The clear or mostly clear single vision or multi-focal lens, wafer or optical pre-form may be tinted with a blue blocking tint while its front convex surface is rendered non-absorptive, e.g., by masking or coating with a dye resist as described previously.

As a result, a portion 303, beginning at the posterior concave surface of the clear or mostly clear single vision or multi-focal lens, wafer or optical pre-form 301 and extending inwardly, and having blue blocking functionality, may be created by tint penetration. Then, the anti-absorbing coating of the front convex surface may be removed. An anti-absorbing coating may then be applied to the concave surface, and the front convex surface and peripheral edges of the single vision or multi-focal lens, wafer or optical pre-form may be tinted (e.g. by immersion in a heated tint pot) for color balancing. The color balancing dyes will be absorbed by the peripheral edges and a portion 302 beginning at the front convex surface and extending inwardly, that was left untinted due to the earlier coating. The order of the foregoing process could be reversed, i.e., the concave surface could first be masked while the remaining portion was tinted for color balancing. Then, the coating could be removed and a depth or thickness at the concave region left untinted by the masking could be tinted for blue blocking.

Figure 4:
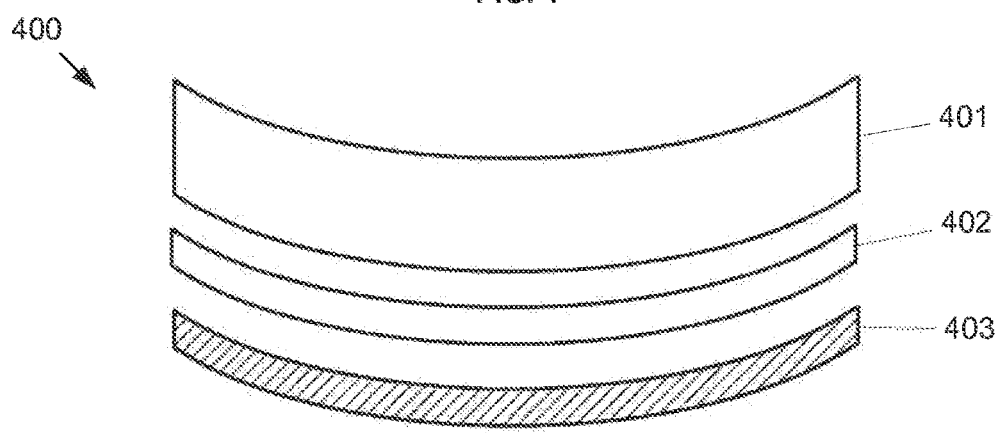
FIG. 4 illustrates an exemplary ophthalmic system formed using an in-mold coating.

Referring now to FIG. 4, an ophthalmic system 400 may be formed using an in-mold coating. More specifically, an ophthalmic component 401 such as a single vision or multi-focal lens, wafer or optical pre-form which has been dyed/tinted with a suitable blue blocking tint, dye or other additive may be color balanced via surface casting using a tinted in-mold coating 403. The in-mold coating 403, comprising a suitable level and/or mixtures of color balancing dyes, may be applied to the convex surface mold (i.e., a mold, not shown, for applying the coating 403 to the convex surface of the ophthalmic component 401). A colorless monomer 402 may be filled in and cured between the coating 403 and ophthalmic component 401. The process of curing the monomer 402 will cause the color balancing in-mold coating to transfer itself to the convex surface of the ophthalmic component 401. The result is a blue blocking ophthalmic system with a color balancing surface coating. The in-mold coating could be, for example, an anti-reflective coating or a conventional hard coating.

Figure 5:
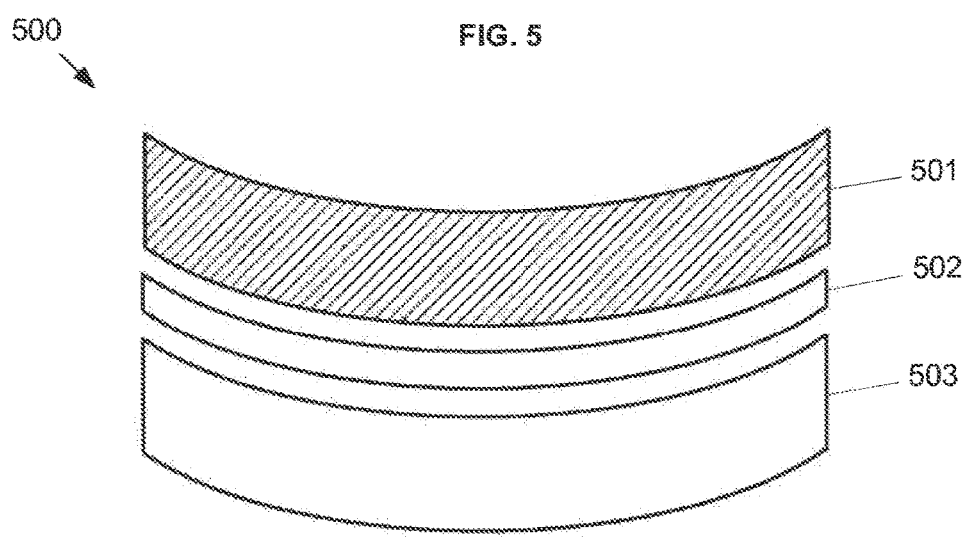
FIG. 5 illustrates the bonding of two ophthalmic components.

Referring now to FIG. 5, an ophthalmic system 500 may comprise two ophthalmic components, one blue blocking and the other color balancing. For example, a first ophthalmic component 501 could be a back single vision or concave surface multi-focal lens, wafer or optical pre-form, dyed/tinted with the appropriate blue blocking tint to achieve the desired level of blue blocking. A second ophthalmic component 503 could be a front single vision or convex surface multi-focal lens, wafer or optical pre-form, bonded or affixed to the back single vision or concave surface multi-focal lens, wafer or optical pre-form, for example using a UV or visible curable adhesive 502. The front single vision or convex surface multi-focal lens, wafer or optical pre-form could be rendered color balancing either before or after it was bonded with the back single vision or concave surface multi-focal lens, wafer or optical pre-form. If after, the front single vision or convex surface multi-focal lens, wafer or optical pre-form could be rendered color balancing, for example, by techniques described above. For example, the back single vision or concave surface multi-focal lens, wafer or optical pre-form may be masked or coated with a dye resist to prevent it taking up color balancing dyes. Then, the bonded back and front portions may be together placed in a heated tint pot containing a suitable solution of color balancing dyes, allowing the front portion to take up color balancing eyes.

Any of the above-described embodiments systems, may be combined with one or more anti-reflective (AR) components. This is shown in FIG. 6, by way of example, for the ophthalmic lenses 100 and 150 shown in FIGS. 1A and 1B. In FIG. 6, a first AR component 601, e.g. a coating, is applied to the concave surface of posterior blue blocking element 101, and a second AR component 602 is applied to the convex surface of color balancing component 102. Similarly, a first AR component 601 is applied to the concave surface of posterior blue blocking component 103, and a second AR component 602 is applied to the convex surface of color balancing component 104.

Figure 7C:
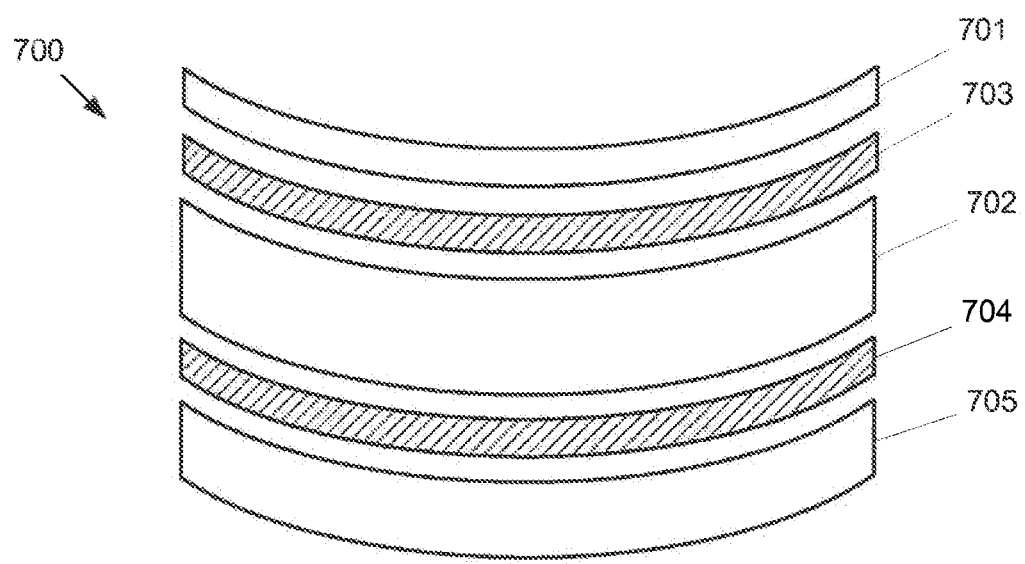
FIG. 7C illustrates another exemplary combination of a blue blocking component, a color balancing component, and an ophthalmic component.

FIGS. 7A-7C show further exemplary systems including a blue blocking component and a color-balancing component. In FIG. 7A, an ophthalmic system 700 includes a blue blocking component 703 and a color balancing component 704 that are formed as adjacent, but distinct, coatings or layers on or adjacent to the anterior surface of a clear or mostly clear ophthalmic lens 702. The blue blocking component 703 is posterior to the color-balancing component 704. On or adjacent to the posterior surface of the clear or mostly clear ophthalmic lens, an AR coating or other layer 701 may be formed. Another AR coating or layer 705 may be formed on or adjacent to the anterior surface of the color-balancing layer 704.

In FIG. 7B, the blue blocking component 703 and color-balancing component 704 are arranged on or adjacent to the posterior surface of the clear or mostly clear ophthalmic lens 702. Again, the blue blocking component 703 is posterior to the color-balancing component 704. An AR component 701 may be formed on or adjacent to the posterior surface of the blue blocking component 703. Another AR component 705 may be formed on or adjacent to the anterior surface of the clear or mostly clear ophthalmic lens 702.

In FIG. 7C, the blue blocking component 703 and the color-balancing component 704 are arranged on or adjacent to the posterior and the anterior surfaces, respectively, of the clear ophthalmic lens 702. Again, the blue blocking component 703 is posterior to the color-balancing component 704. An AR component 701 may be formed on or adjacent to the posterior surface of the blue blocking component 703, and another AR component 705 may be formed on or adjacent to the anterior surface of the color-balancing component 704.

Figure 8A:
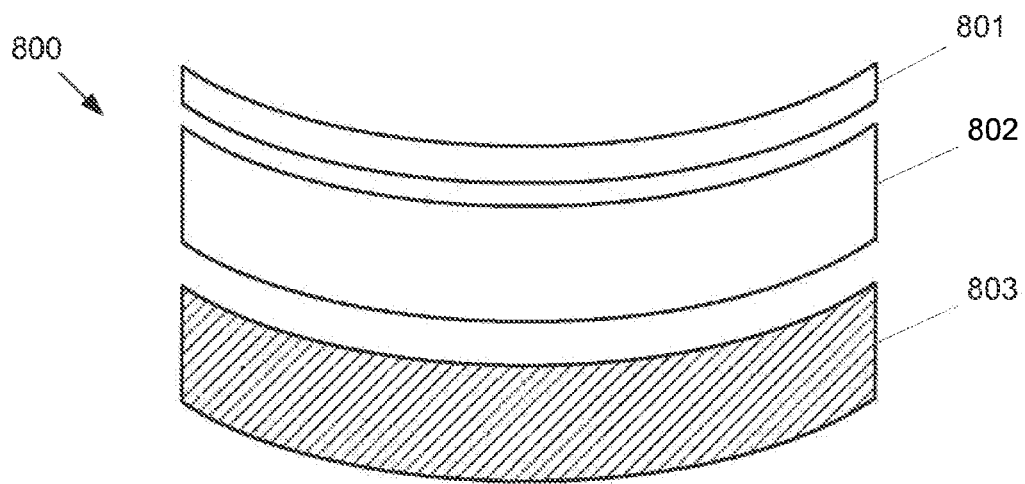
FIG. 8A shows an example of an ophthalmic system including a multi-functional blue blocking and color-balancing component.
Figure 8B:
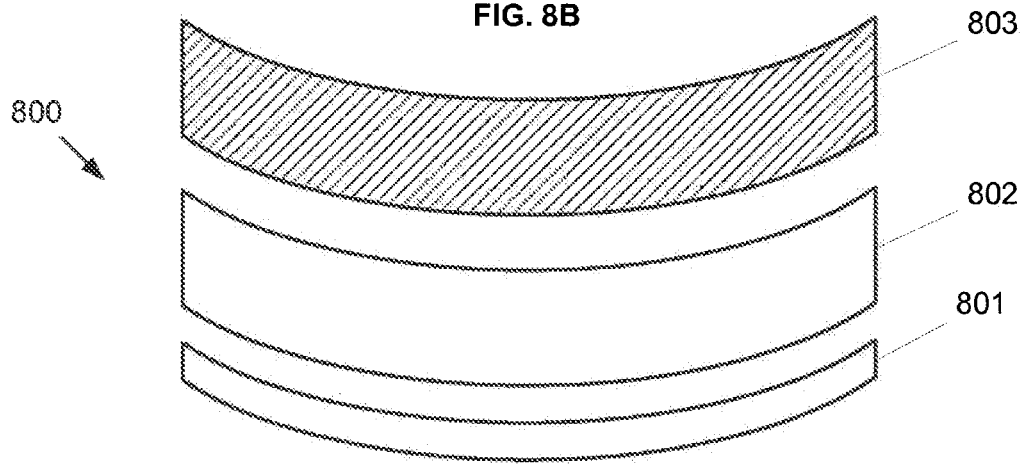
FIG. 8B shows another example of an ophthalmic system including a multi-functional blue blocking and color-balancing component.

FIGS. 8A and 8B show an ophthalmic system 800 in which functionality to both block blue light wavelengths and to perform color balancing may be combined in a single component 803. For example, the combined functionality component may block blue light wavelengths and reflect some green and red wavelengths as well, thus neutralizing the blue and eliminating the appearance of a dominant color in the lens. The combined functionality component 803 may be arranged on or adjacent to either the anterior or the posterior surface of a clear ophthalmic lens 802. The ophthalmic lens 800 may further include an AR component 801 on or adjacent to either the anterior or the posterior surface of the clear ophthalmic lens 802.

To quantify the effectiveness of a color balancing component, it may be useful to observe light reflected and/or transmitted by a substrate of an ophthalmic material. The observed light may be characterized by its CIE coordinates to indicate the color of observed light; •by comparing these coordinates to the CIE coordinates of the incident light, it is possible to determine how much the color of the light was shifted due to the reflection/transmission. White light is defined to have CIE coordinates of (0.33, 0.33). Thus, the closer an observed light's CIE coordinates are to (0.33, 0.33), the "more white" it will appear to an observer. To characterize the color shifting or balancing performed by a lens, (0.33, 0.33) white light may be directed at the lens, and the CIE of reflected and transmitted light observed. If the transmitted light has a CIE of about (0.33, 0.33), there will be no color shifting, and items viewed through the lens will have a natural appearance, i.e., the color will not be shifted relative to items observed without the lens. Similarly, if the reflected light has a CIE of about (0.33, 0.33), the lens will have a natural cosmetic appearance, i.e., it will not appear tinted to an observer viewing a user of the lens or ophthalmic system. Thus, it is desirable for transmitted and reflected light to have a CIE as close to (0.33, 0.33) as possible.

Figure 9:
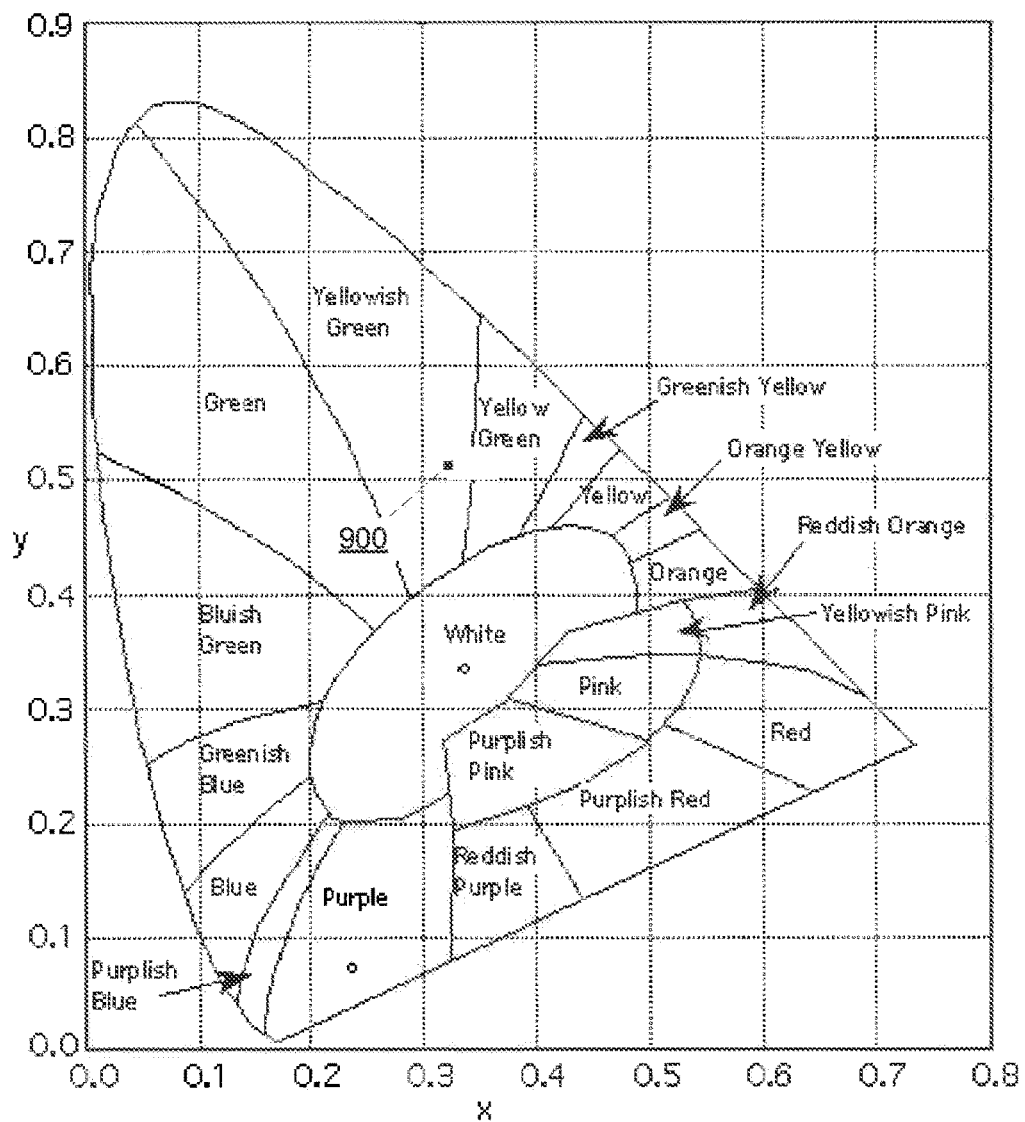
FIG. 9 shows a reference of observed colors that correspond to various CIE coordinates.

FIG. 9 shows a CIE plot indicating the observed colors corresponding to various CIE coordinates. A reference point 900 indicates the coordinates (0.33, 0.33). Although the central region of the plot typically is designated as "white," some light having CIE coordinates in this region can appear slightly tinted to a viewer. For example, light having CIE coordinates of (0.4, 0.4) will appear yellow to an observer. Thus, to achieve a color-neutral appearance in an ophthalmic system, it is desirable for (0.33, 0.33) light (i.e., white light) that is transmitted and/or reflected by the system to have CIE coordinates as close to (0.33, 0.33) as possible after the transmission/reflection. The CIE plot shown in FIG. 9 will be used herein as a reference to show the color shifts observed with various systems, though the labeled regions will be omitted for clarity.

Absorbing dyes may be included in the substrate material of an ophthalmic lens by injection molding the dye into the substrate material to produce lenses with specific light transmission and absorption properties. These dye materials can absorb at the fundamental peak wavelength of the dye or at shorter resonance wavelengths due to the presence of a Soret band typically found in porphyrin materials. Exemplary ophthalmic materials include various glasses and polymers such as CR-39®, TRIVEX, polycarbonate, polymethylmethacrylate, silicone, and fluoro-polymers, though other materials may be used and are known for various ophthalmic systems.

Figure 10:
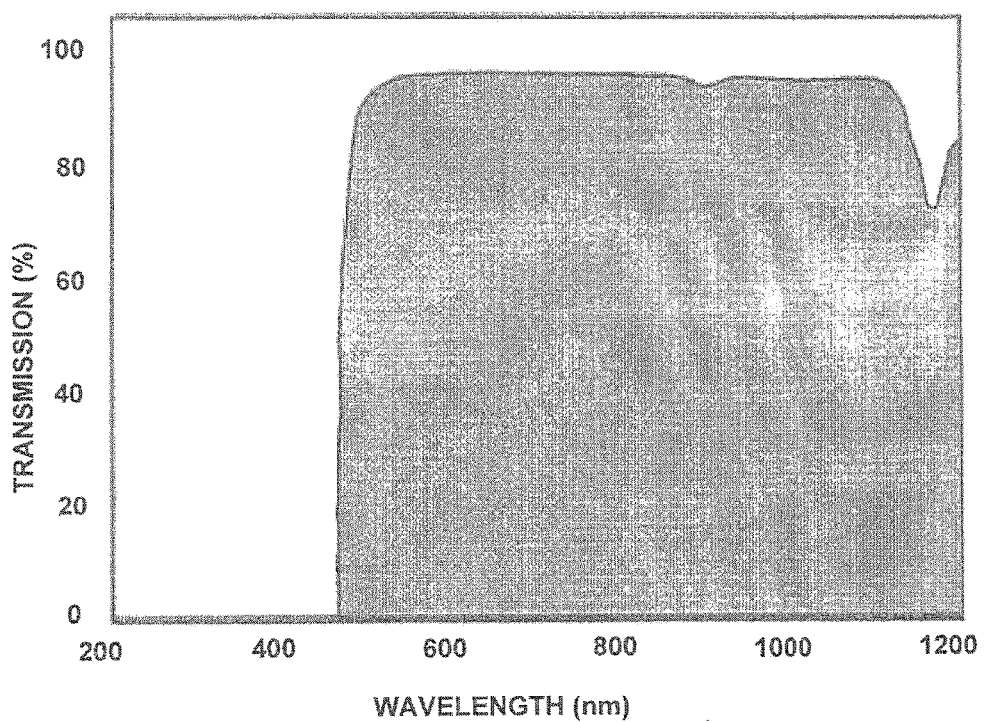
FIG. 10 shows the transmission of the GENTEX E465 absorbing dye.
Figure 11:
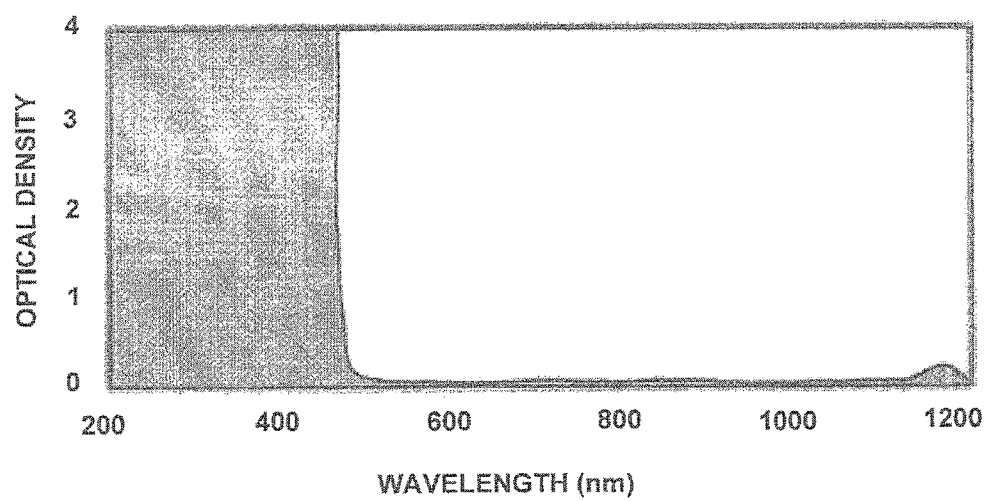
FIG. 11 shows the absorbance of the GENTEX E465 absorbing dye.

By way of example only, GENTEX day material E465 (available from Gentex Corp., Zeeland, Mich.) transmittance and absorbance is shown in FIGS. 10-11. The Absorbance (A) is related to the transmittance (T) by the equation, $A=\log_{10}(1/T)$. In this case, the transmittance is between 0 and 1 (0<T<1). Often transmittance is express as a percentage, i.e., 0%<T<100%. The E465 dye blocks those wavelengths less than 465 and is normally provided to block these wavelengths with high optical density (OD>4). Similar products are available to block other wavelengths. For example, E420 from GENTEX blocks wavelengths below 420 nm. Other exemplary dyes include porphyrins, perylene, and similar dyes that can absorb at blue wavelengths.

Figure 12:
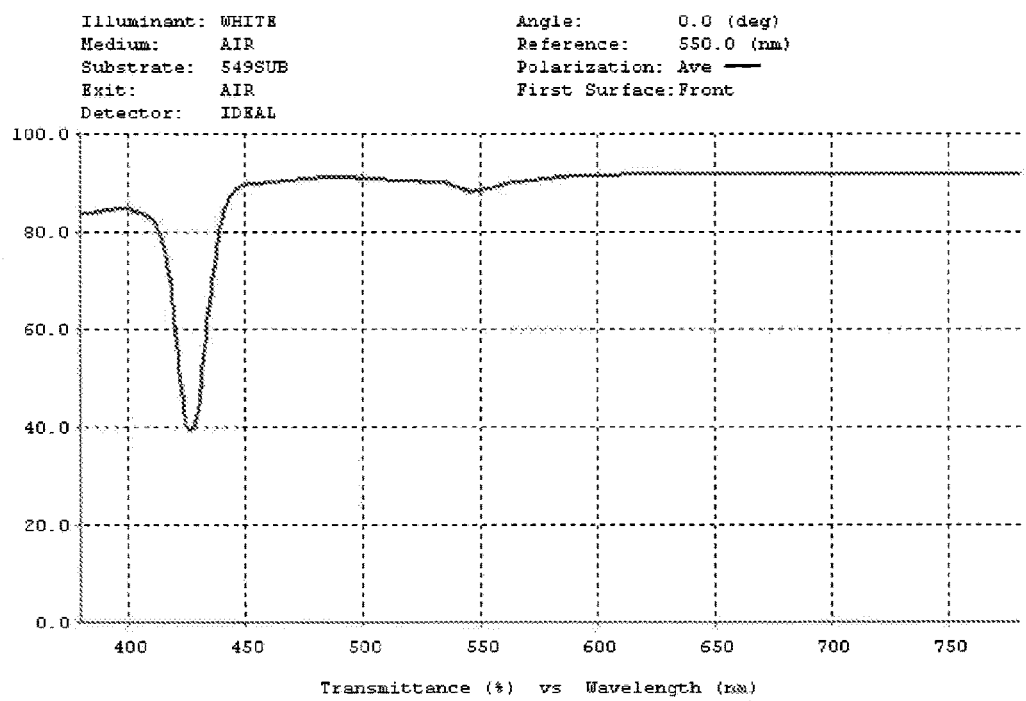
FIG. 12 shows the transmittance of a polycarbonate substrate with a dye concentration suitable for absorbing in the 430 nm range.

The absorbance at shorter wavelengths can be reduced by a reduction of the dye concentration. This and other dye materials can achieve a transmittance of ~50% in the 430 nm region. FIG. 12 shows the transmittance of a polycarbonate substrate with a dye concentration suitable for absorbing in the 430 nm range, and with some absorption in the range of 420-440 nm. This was achieved by reducing the concentration of the dye and including the effects of a polycarbonate substrate. The rear surface is at this point not antireflection coated.

The concentration of dye also may affect the appearance and color shift of an ophthalmic system. By reducing the concentration, systems with varying degrees of color shift may be obtained. A "color shift" as used herein refers to the amount by which the CIE coordinates of a reference light change after transmission and/or reflection of the ophthalmic system. It also may be useful to characterize a system by the color shift causes by the system due to the differences in various types of light typically perceived as white (e.g., sunlight, incandescent light, and fluorescent light). It therefore may be useful to characterize a system based on the amount by which the CIE coordinates of incident light are shifted when the light is transmitted and/or reflected by the system. For example, a system in which light with CIE coordinates of (0.33, 0.33) becomes light with a CIE of (0.30, 0.30) after transmission may be described as causing a color shift of (−0.03, −0.03), or, more generally, (±0.03, ±0.03). Thus the color shift caused by a system indicates how "natural" light and viewed items appear to a wearer of the system. As further described below, systems causing color shifts of less than (±0.05, ±0.05) to (±0.02, ±0.02) have been achieved.

A reduction in short-wavelength transmission in an ophthalmic system may be useful in reducing cell death due to photoelectric effects in the eye, such as excitation of A2E, a lipofuscin fluorophore. It has been shown that reducing incident light at 430±30 nm by about 50% can reduce cell death by about 80%. See, for example, Janet R. Sparrow et al., "Blue light-absorbing intraocular lens and retinal pigment epithelium protection in vitro," J. Cataract Refract. Surg. 2004, vol. 30, pp. 873-78, the disclosure of which is incorporated by reference in its entirety. It is further believed that reducing the amount of blue light, such as light in the 430-460 nm range, by as little as 5% may similarly reduce cell death and/or degeneration, and therefore prevent or reduce the adverse effects of conditions such as atrophic age-related macular degeneration.

Although an absorbing dye may be used to block undesirable wavelengths of light, the dye may produce a color tint in the lens as a side effect. For example, many blue blocking ophthalmic lenses have a yellow coloring that is often undesirable and/or aesthetically displeasing. To offset this coloring, a color balancing coating may be applied to one or both surfaces of a substrate including the absorbing dye therein.

Figure 13:
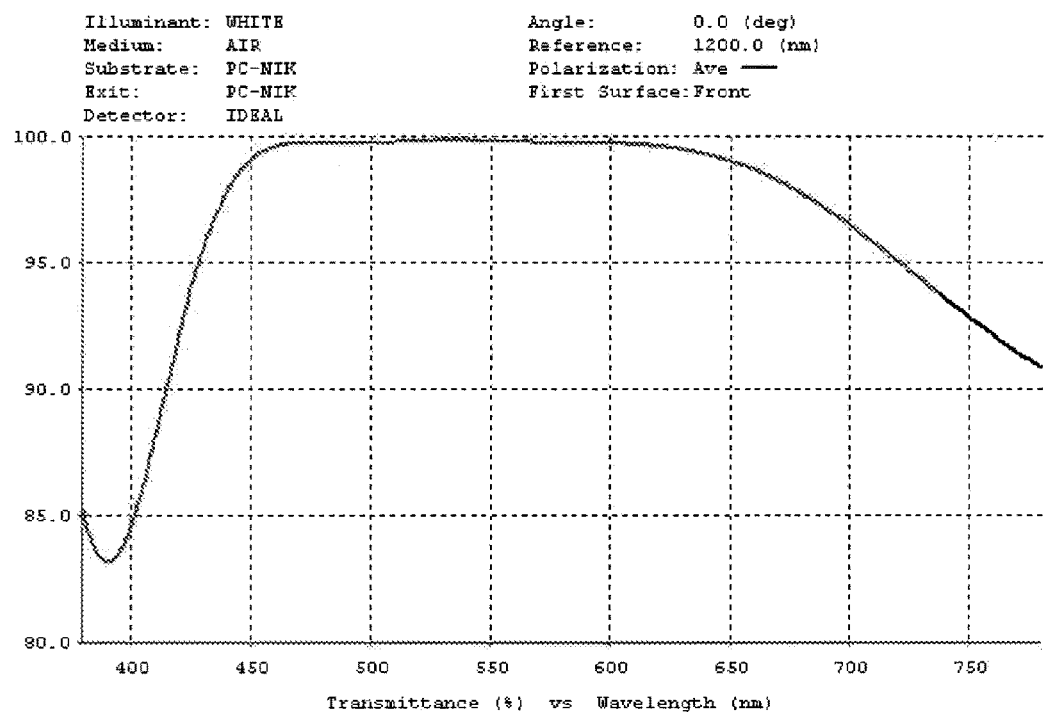
FIG. 13 shows the transmittance as a function of wavelength of a polycarbonate substrate with an antireflective coating.
Figure 14:
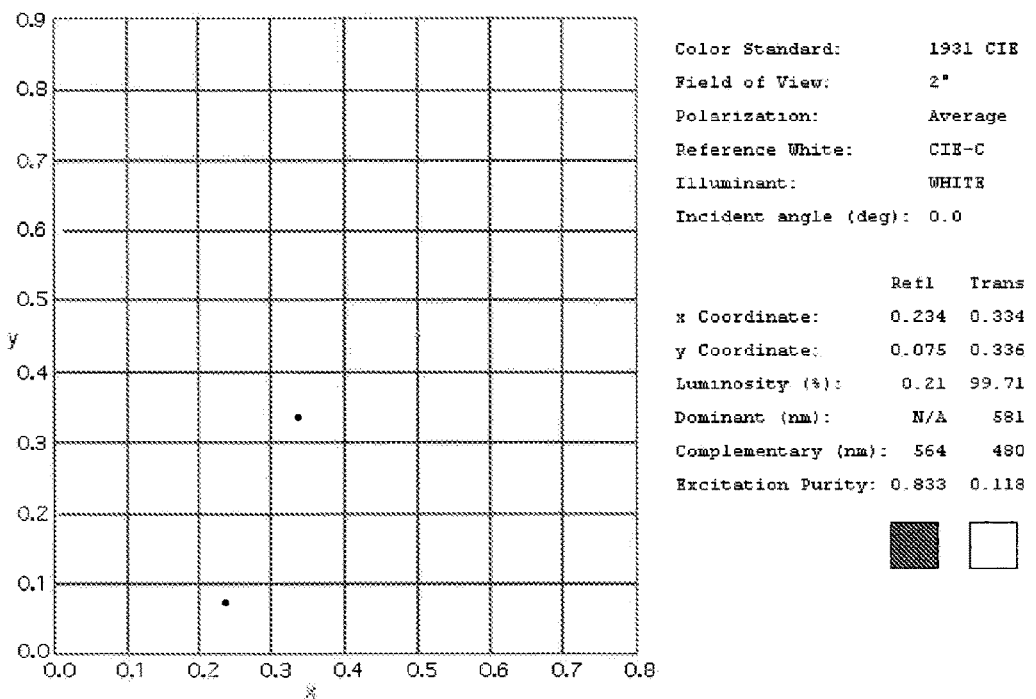
FIG. 14 shows the color plot of a polycarbonate substrate with an antireflective coating.

Antireflection (AR) coatings (which are interference filters) are well-established within the commercial ophthalmic coating industry. The coatings typically are a few layers, often less than 10, and typically are used to reduce the reflection from the polycarbonate surface to less than 1%. An example of such a coating on a polycarbonate surface is shown in FIG. 13. The color plot of this coating is shown in FIG. 14 and it is observed that the color is quite neutral. The total reflectance was observed to be 0.21%. The reflected light was observed to have CIE coordinates of (0.234, 0.075); the transmitted light had CIE coordinates of (0.334, 0.336).

Figure 15:
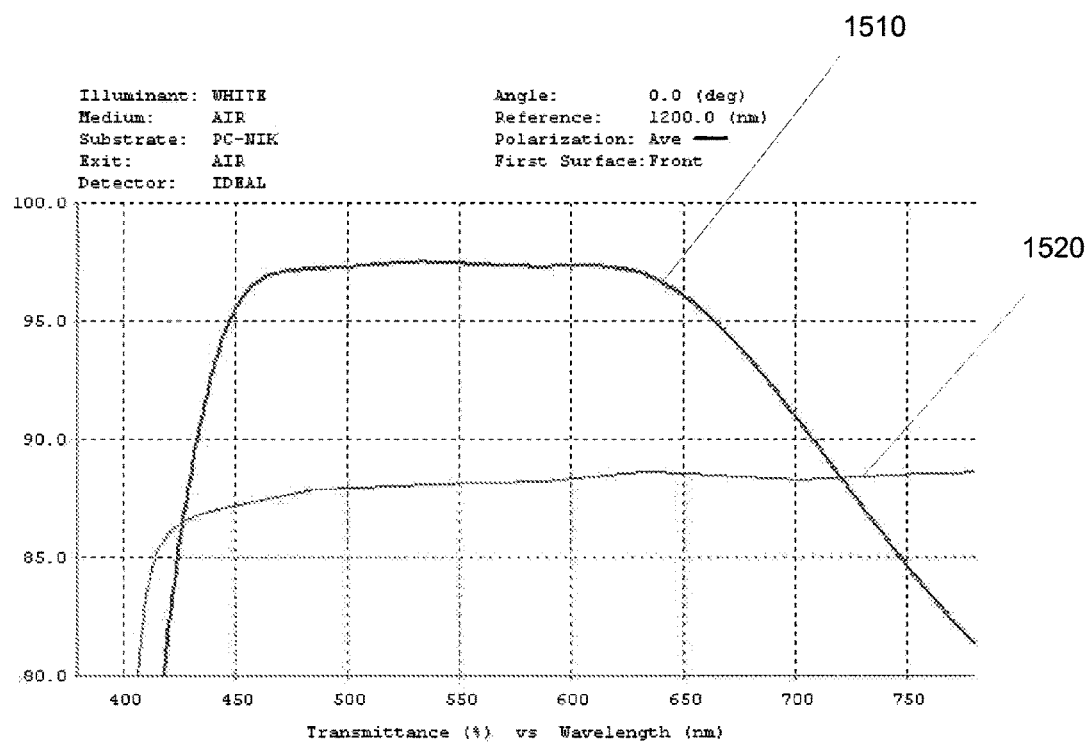
FIG. 15 shows the transmittance as a function of wavelength of an uncoated polycarbonate substrate and a polycarbonate substrate with an antireflective coating on both surfaces.

AR coatings may be applied to both surfaces of a lens or other ophthalmic device to achieve a higher transmittance. Such a configuration is shown in FIG. 15 where the darker line 1510 is the AR coated polycarbonate and the thinner line 1520 is an uncoated polycarbonate substrate. This AR coating provides a 10% increase in total transmitted light. There is some natural loss of light due to absorption in the polycarbonate substrate. The particular polycarbonate substrate used for this example has a transmittance loss of approximately 3%. In the ophthalmic industry AR coatings generally are applied to both surfaces to increase the transmittance of the lens.

In systems according to the embodiments of the present invention, AR coatings or other color balancing films may be combined with an absorbing dye to allow for simultaneous absorption of blue wavelength light, typically in the 430 nm region, and increased transmittance. As previously described, elimination of the light in the 430 nm region alone typically results in a lens that has some residual color cast. To spectrally tailor the light to achieve a color neutral transmittance, at least one of the AR coatings may be modified to adjust the overall transmitted color of the light. In ophthalmic systems according to the embodiments of the invention, this adjustment may be performed on the front surface of the lens to create the following lens structure:

Air (farthest from the user's eye)/Front convex lens coating/Absorbing ophthalmic lens substrate/rear concave anti-reflection coating/Air (closest to the user's eye).

In such a configuration, the front coating may provide spectral tailoring to offset the color cast resulting from the absorption in the substrate in addition to the antireflective function typically performed in conventional lenses. The lens therefore may provide an appropriate color balance for both transmitted and reflected light. In the case of transmitted light the color balance allows for proper color vision; in the case reflected light the color balance may provide the appropriate lens aesthetics.

In some cases, a color balancing film may be disposed between two layers of other ophthalmic material. For example, a filter, AR film, or other film may be disposed within an ophthalmic material. For example, the following configuration may be used:

Air (farthest from the user's eye)/ophthalmic material/film/ophthalmic material/air (closest to user's eye).

The color balancing film also may be a coating, such as a hardcoat, applied to the outer and/or inner surface of a lens. Other configurations are possible. For example, referring to FIG. 3, an ophthalmic system may include an ophthalmic material 301 doped with a blue-absorbing dye and one or more color balancing layers 302, 303. In another configuration, an inner layer 301 may be a color balancing layer surrounded by ophthalmic material 302, 303 doped with a blue-absorbing dye. Additional layers and/or coatings, such as AR coatings, may be disposed on one or more surfaces of the system. It will be understood how similar materials and configurations may be used, for example in the systems described with respect to FIGS. 4-8B.

Thus, optical films and/or coatings such as AR coatings may be used to fine-tune the overall spectral response of a lens having an absorbing dye. Transmission variation across the visible spectrum is well known and varies as a function of the thickness and number of layers in the optical coating. In embodiments of the invention one or more layers can be used to provide the needed adjustment of the spectral properties.

Figure 16:
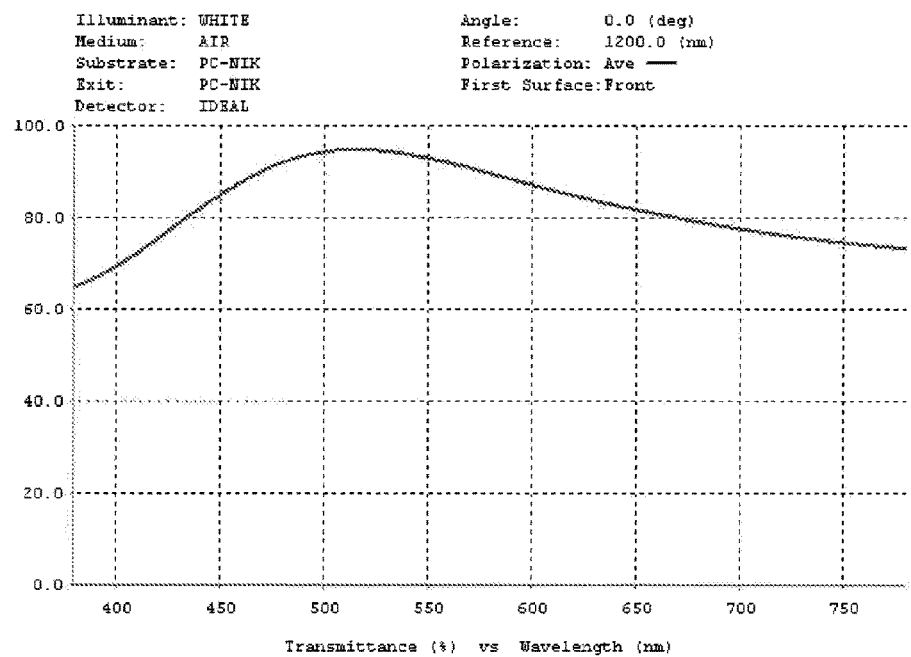
FIG. 16 shows the spectral transmittance of a 106 nm layer of $TiO_2$ on a polycarbonate substrate.
Figure 17:
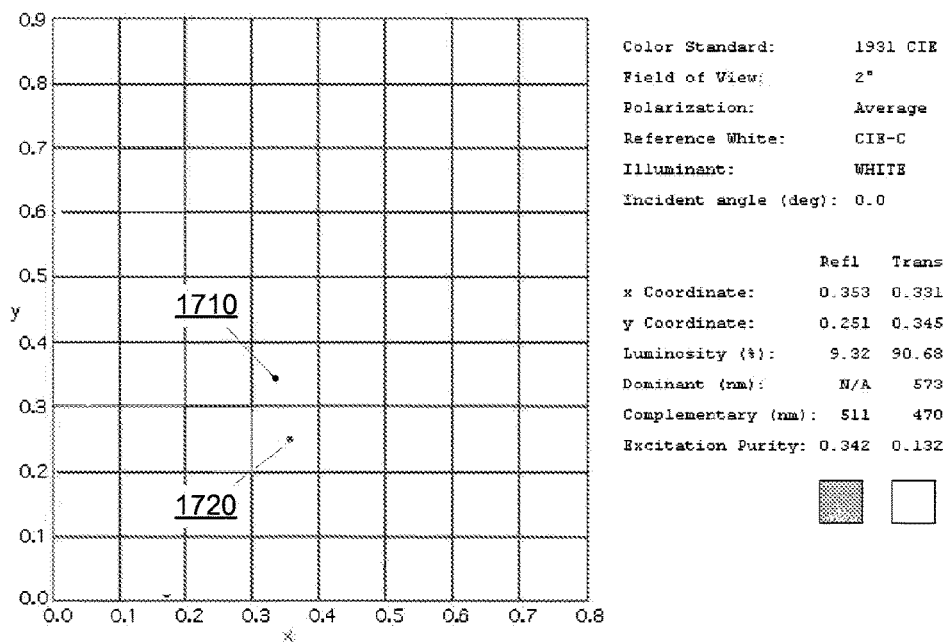
FIG. 17 shows the color plot of a 106 nm layer of TiO$_2$ on a polycarbonate substrate.

In an exemplary system, color variation is produced by a single layer of TiO2 (a common AR coating material). FIG. 16 shows the spectral transmittance of a 106 nm thick single layer of TiO2. The color plot of this same layer is shown in FIG. 17. The CIE color coordinates (x, y) 1710 shown for the transmitted light are (0.331, 0.345). The reflected light had CIE coordinates of (0.353, 0.251) 1720, resulting in a purplish-pink color.

Figure 18:
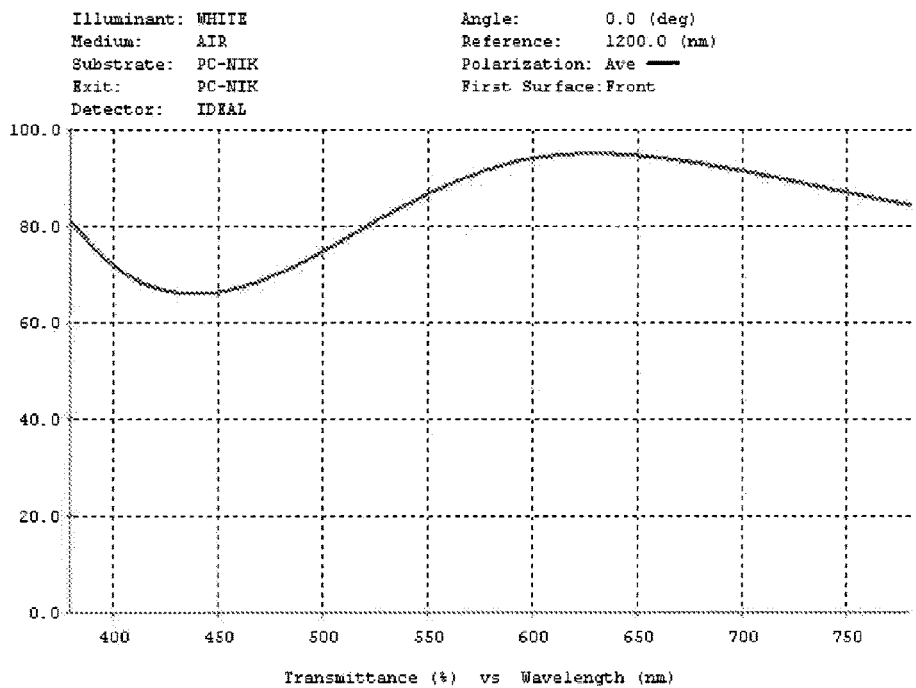
FIG. 18 shows the spectral transmittance of a 134 nm layer of TiO$_2$ on a polycarbonate substrate.
Figure 19:
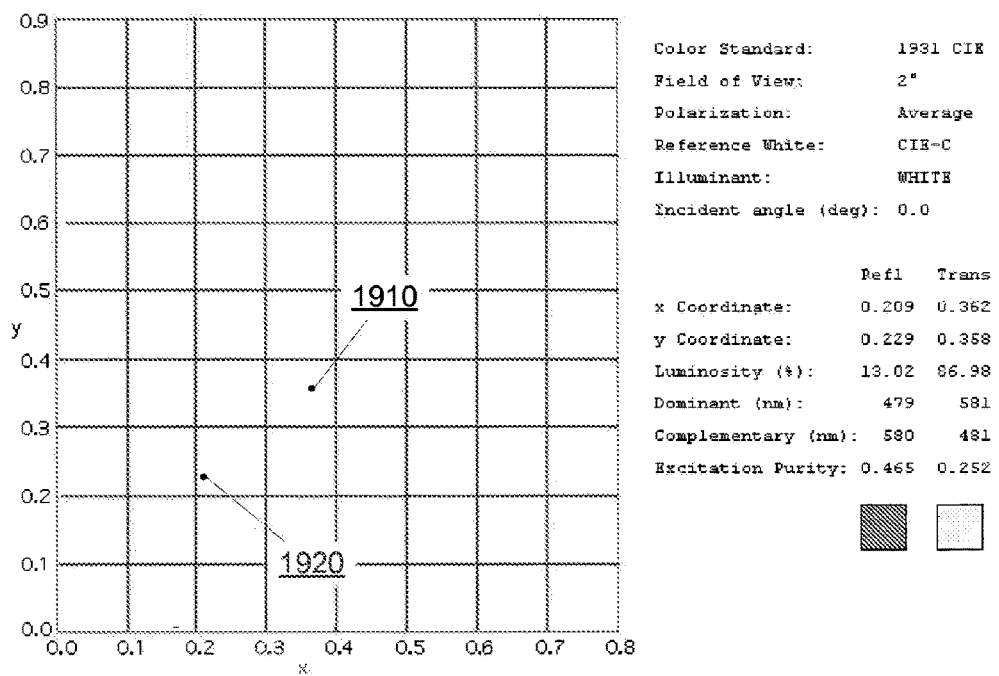
FIG. 19 shows the color plot of a 134 nm layer of TiO2 on a polycarbonate substrate.

Changing the thickness of the TiO$_2$ layer changes the color of the transmitted light as shown in the transmitted spectra and color plot for a 134 nm layer, shown in FIGS. 18 and 19 respectively. In this system, the transmitted light exhibited CIE coordinates of (0.362, 0.368) 1910, and the reflected light had CIE coordinates of (0.209, 0.229) 1920. The transmission properties of various AR coatings and the prediction or estimation thereof are known in the art. For example, the transmission effects of an AR coating formed of a known thickness of an AR material may be calculated and predicted using various computer programs. Exemplary, non-limiting programs include Essential Macleod Thin Films Software available from Thin Film Center, Inc., TFCalc available from Software Spectra, Inc., and FilmStar Optical Thin Film Software available from FTG Software Associates. Other methods may be used to predict the behavior of an AR coating or other similar coating or film.

Figure 20:
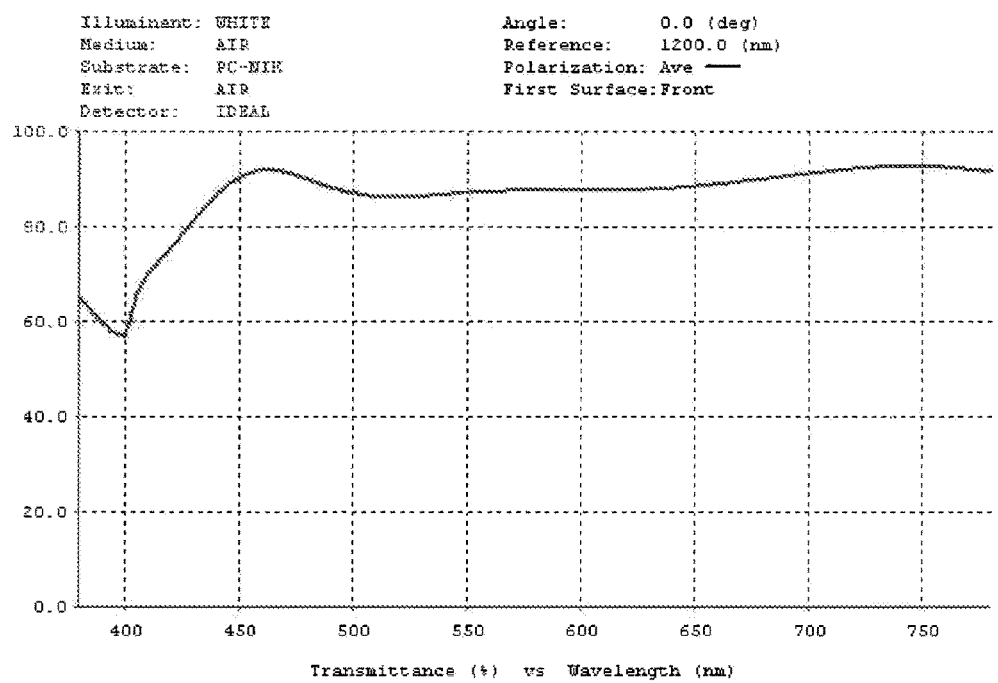
FIG. 20 shows the spectral transmittance of a modified AR coating suitable for color balancing a substrate having a blue absorbing dye.
Figure 21:
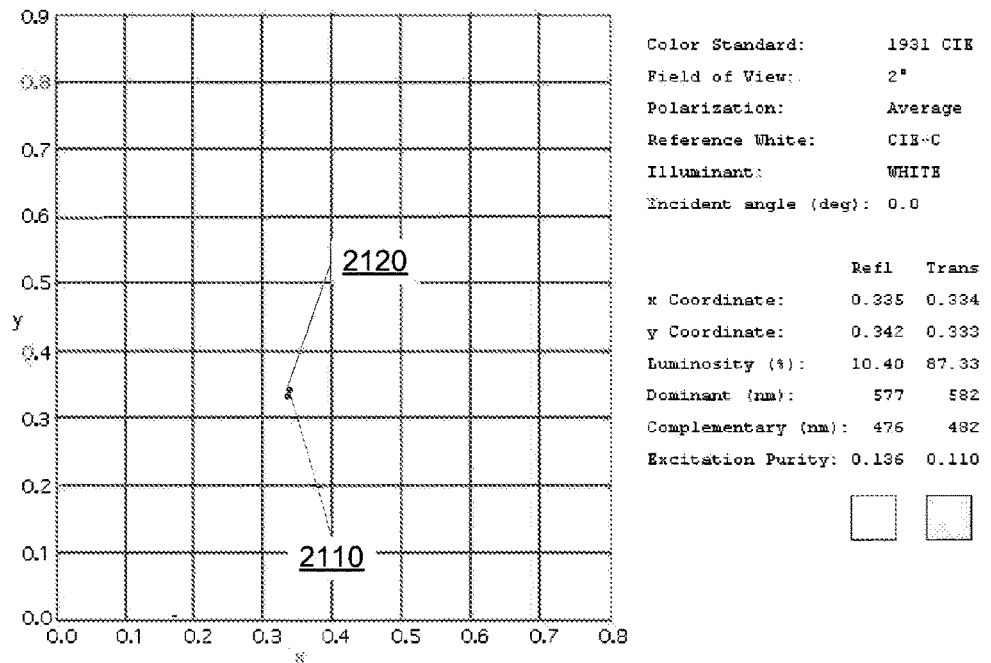
FIG. 21 shows the color plot of a modified AR coating suitable for color balancing a substrate having a blue absorbing dye.
Figure 22:
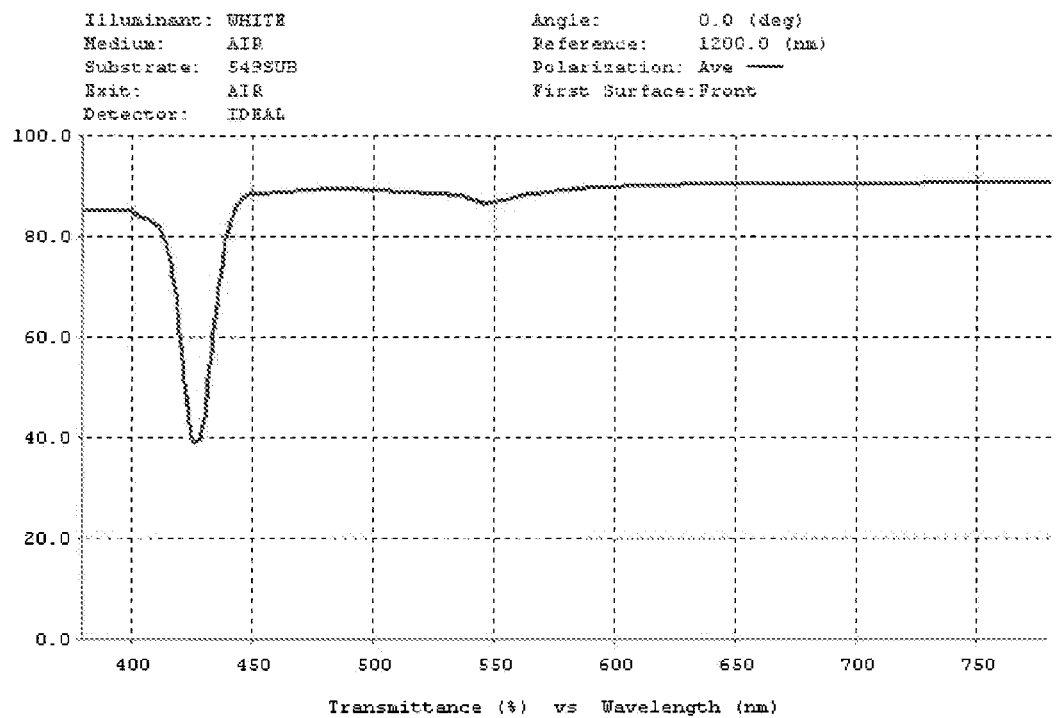
FIG. 22 shows the spectral transmittance of a substrate having a blue absorbing dye.
Figure 23:
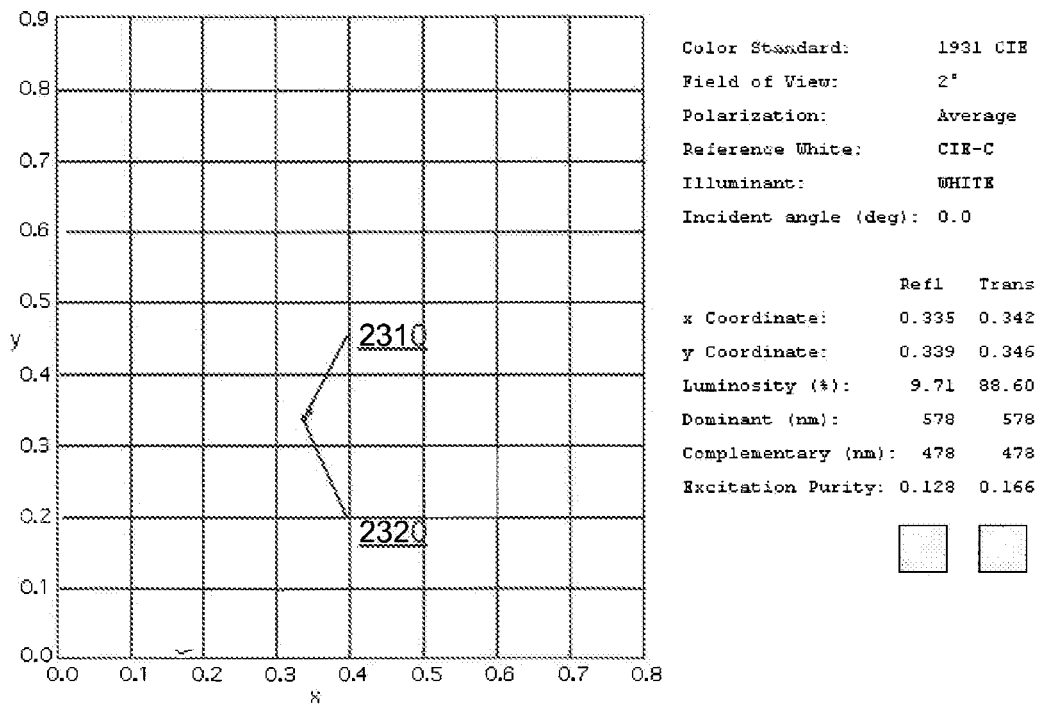
FIG. 23 shows the color plot of a substrate having a blue absorbing dye.
Figure 24:
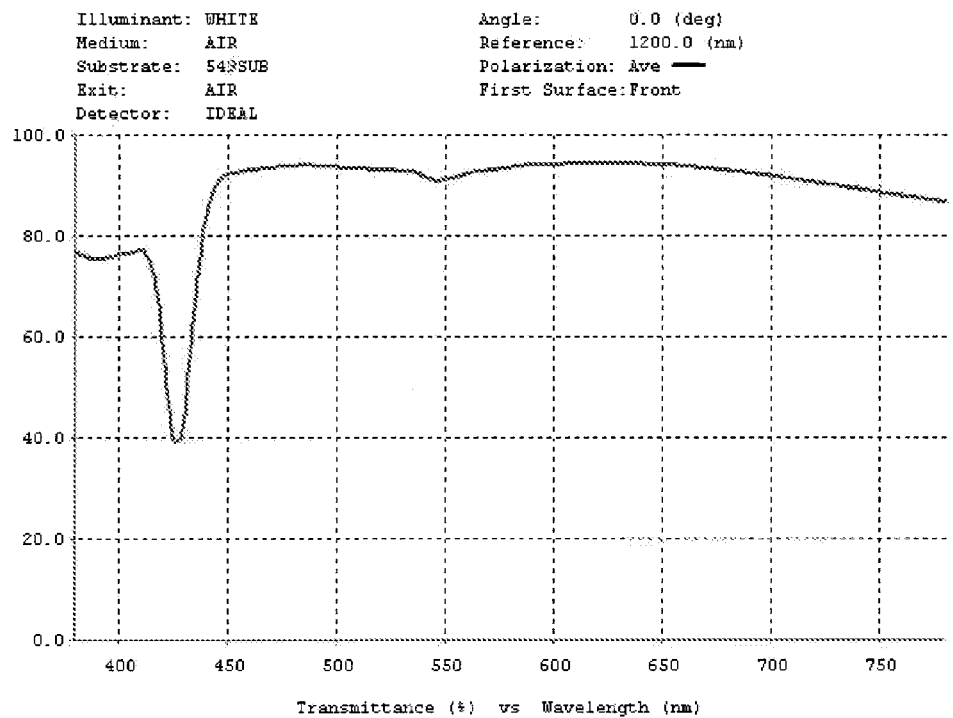
FIG. 24 shows the spectral transmittance of a substrate having a blue absorbing dye and a rear AR coating.
Figure 25:
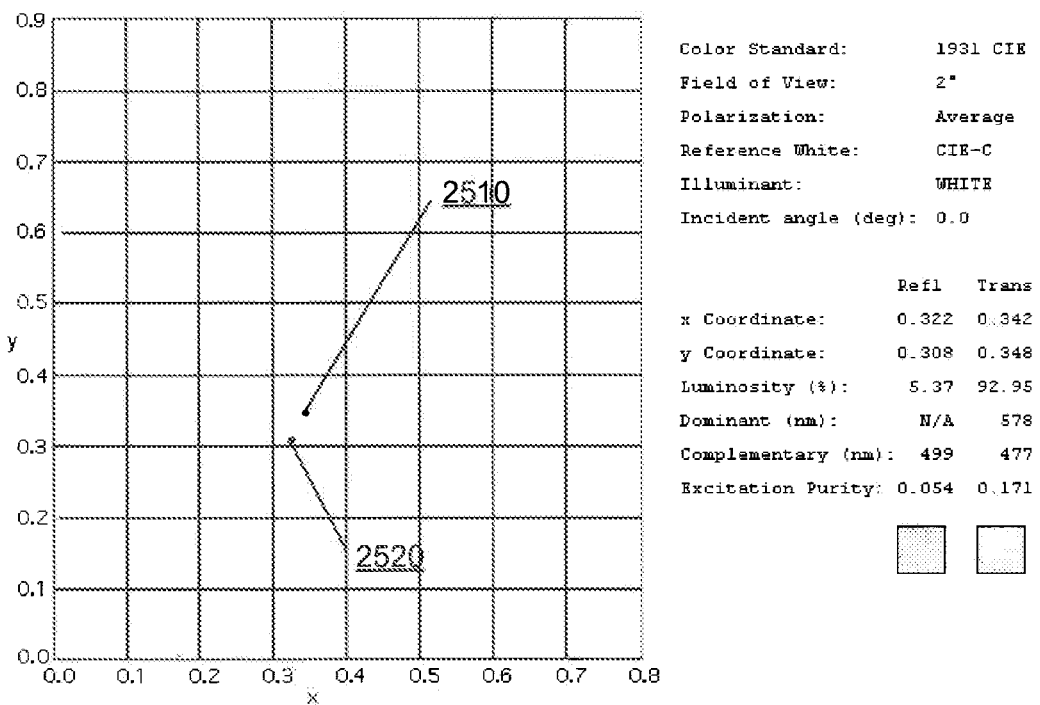
FIG. 25 shows the color plot of a substrate having a blue absorbing dye and a rear AR coating.

In systems according to embodiments of the invention, a blue-absorbing dye may be combined with a coating or other film to provide a blue blocking, color balanced system. The coating may be an AR coating on the front surface that is modified to correct the color of the transmitted and/or reflected light. The transmittance and color plot of an exemplary AR coating are shown in FIGS. 20 and 21, respectively. In FIG. 21, the transmitted light exhibited CIE coordinates of (0.334, 0.333) 2110, and the reflected light had CIE coordinates of (0.335, 0.342) 2120. FIGS. 22 and 23 show the transmittance and color plot, respectively, for a polycarbonate substrate having a blue absorbing dye without an AR coating. The dyed substrate absorbs most strongly in the 430 nm region, including some absorption in the 420-440 nm region. In FIG. 23, the transmitted light exhibited CIE coordinates of (0.342, 0.346) 2310, and the reflected light had CIE coordinates of (0.335, 0.339) 2320. The dyed substrate may be combined with an appropriate AR coating as illustrated in FIGS. 20-21 to increase the overall transmittance of the system. The transmittance and color plot for a dyed substrate having a rear AR coating are shown in FIGS. 24 and 25, respectively. In FIG. 25, the transmitted light exhibited CIE coordinates of (0.342, 0.348) 2510, and the reflected light had CIE coordinates of (0.322, 0.308) 2520.

Figure 26:
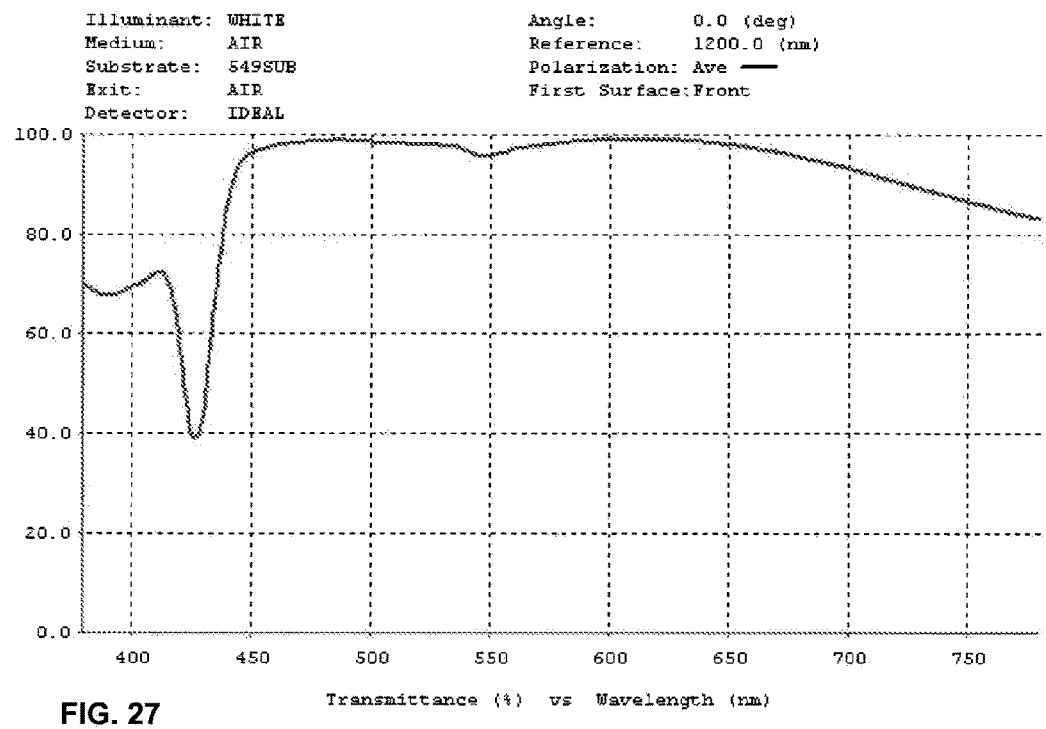
FIG. 26 shows the spectral transmittance of a substrate having a blue absorbing dye and AR coatings on the front and rear surfaces.
Figure 27:
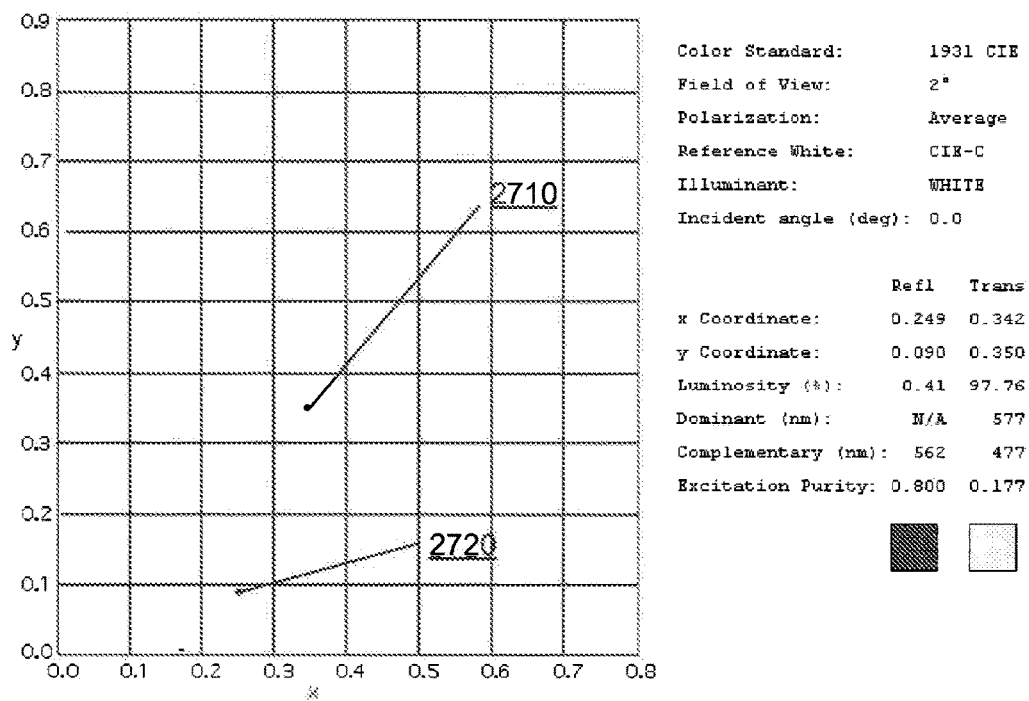
FIG. 27 shows the color plot of a substrate having a blue absorbing dye and AR coatings on the front and rear surfaces.
Figure 28:
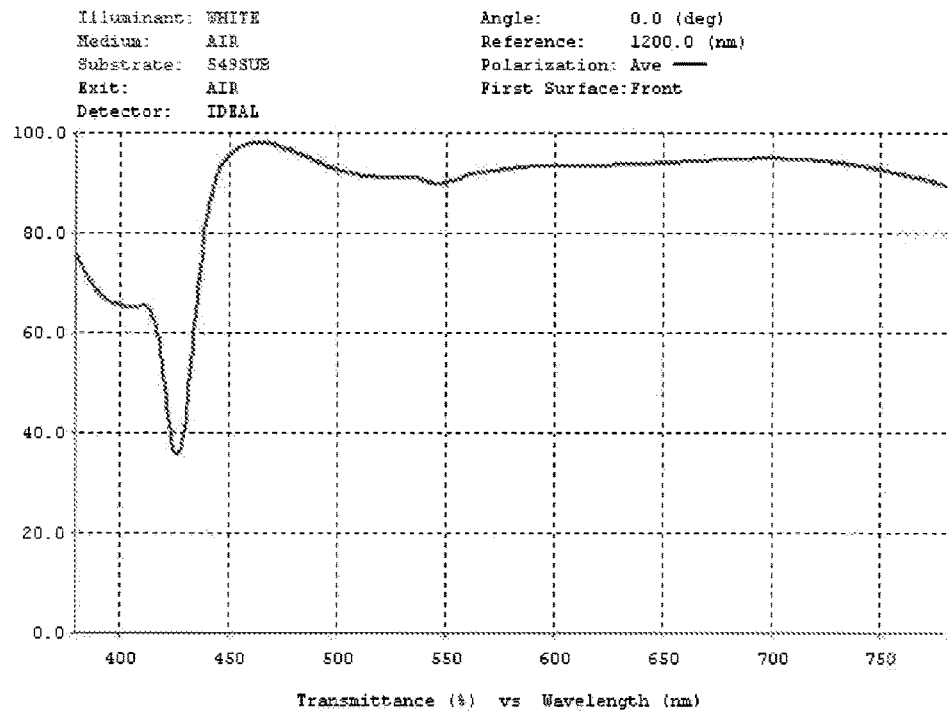
FIG. 28 shows the spectral transmittance of a substrate having a blue absorbing dye and a color balancing AR coating.
Figure 29:
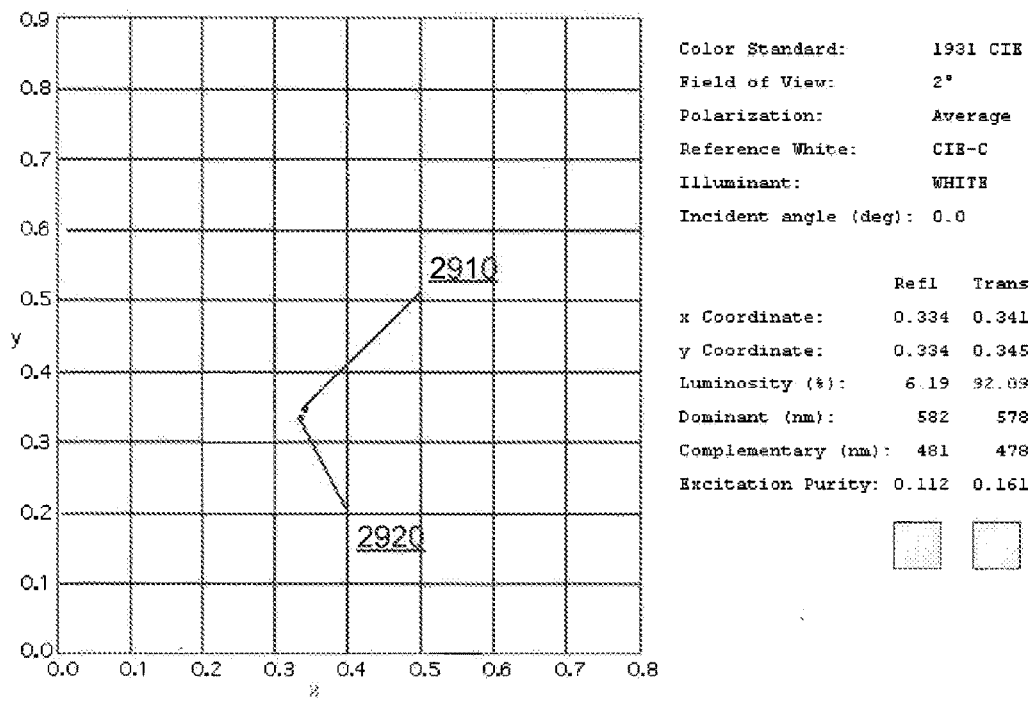
FIG. 29 shows the color plot of a substrate having a blue absorbing dye and a color balancing AR coating.

An AR coating also may be applied to the front of an ophthalmic system (i.e., the surface farthest from the eye of a wearer of the system), resulting in the transmittance and color plot shown in FIGS. 26 and 27, respectively. Although the system exhibits a high transmission and transmitted light is relatively neutral, the reflected light has a CIE of (0.249, 0.090) 2720. Therefore, to more completely color balance the effects of the blue absorbing dye, the front AR coating may be modified to achieve the desired color balance to produce a color neutral configuration. The transmittance and the color plot of this configuration are shown in FIGS. 28 and 29 respectively. In this configuration, both the transmitted and reflected light may be optimized to achieve color neutrality. It may be preferred for the interior reflected light to be about 6%. Should the reflectivity level be annoying to the wearer of the system, the reflection can be further reduced by way of adding an additional different absorbing dye into the lens substrate that would absorb a different wavelength of visible light. However, the design of this configuration achieves remarkable performance and satisfies the need for a blue blocking, color balanced ophthalmic system as described herein. The total transmittance is over 90% and both the transmitted and reflected colors are quite close to the color neutral white point. As shown in FIG. 29, the reflected light has a CIE of (0.334, 0.334) 2920, and the transmitted light has a CIE of (0.341, 0.345) 2910, indicating little or no color shifting.

In some configurations, the front modified anti-reflection coating can be designed to block 100% of the blue light wave length to be inhibited. However, this may result in a back reflection of about 9% to 10% for the wearer. This level of reflectivity can be annoying to the wearer. Thus by combining an absorbing dye into the lens substrate this reflection with the front modified anti-reflection coating the desired effect can be achieved along with a reduction of the reflectivity to a level that is well accepted by the wearer. The reflected light observed by a wearer of a system including one or more AR coatings may be reduced to 8% or less, or more preferably 3% or less.

The combination of a front and rear AR coating may be referred to as a dielectric stack, and various materials and thicknesses may be used to further alter the transmissive and reflective characteristics of an ophthalmic system. For example, the front AR coating and/or the rear AR coating may be made of different thicknesses and/or materials to achieve a particular color balancing effect. In some cases, the materials used to create the dielectric stack may not be materials traditionally used to create antireflective coatings. That is, the color balancing coatings may correct the color shift caused by a blue absorbing dye in the substrate without performing an anti-reflective function.

As discussed previously, filters are another technique for blue blocking. Accordingly, any of the blue blocking components discussed could be or include or be combined with blue blocking filters. Such filters may include rugate filters, interference filters, band-pass filters, band-block filters, notch filters or dichroic filters.

In embodiments of the invention, one or more of the above-disclosed blue-blocking techniques may be used in conjunction with other blue-blocking techniques. By way of example only, a lens or lens component may utilize both a dye/tint and a rugate notch filter to effectively block blue light.

Any of the above-disclosed structures and techniques may be employed in an ophthalmic system according to embodiments of the present invention to perform blocking of blue light wavelengths at or near 400-460 nm. For example, in embodiments the wavelengths of blue light blocked may be within a predetermined range. In embodiments, the range may be 430±30 nm. In other embodiments, the range may be 430±20 nm. In still other embodiments, the range may be 430±10 nm. In embodiments, the ophthalmic system may limit transmission of blue wavelengths within the above defined ranges to substantially 90% of incident wavelengths. In embodiments, the ophthalmic system may limit transmission of blue wavelengths within the above-defined ranges to substantially 80% of incident wavelengths. In other embodiments, the ophthalmic system may limit transmission of the blue wavelengths within the above-defined ranges to substantially 70% of incident wavelengths. In other embodiments, the ophthalmic system may limit transmission of the blue wavelengths within the above-defined ranges to substantially 60% of incident wavelengths. In other embodiments, the ophthalmic system may limit transmission of the blue wavelengths within the above-defined ranges to substantially 50% of incident wavelengths. In other embodiments, the ophthalmic system may limit transmission of the blue wavelengths within the above-defined ranges to substantially 40% of incident wavelengths. In still other embodiments, the ophthalmic system may limit transmission of the blue wavelengths within the above-defined ranges to substantially 30% of incident wavelengths. In still other embodiments, the ophthalmic system may limit transmission of the blue wavelengths within the above-defined ranges to substantially 20% of incident wavelengths. In still other embodiments, the ophthalmic system may limit transmission of the blue wavelengths within the above-defined ranges to substantially 10% of incident wavelengths. In still other embodiments, the ophthalmic system may limit transmission of the blue wavelengths within the above-defined ranges to substantially 5% of incident wavelengths. In still other embodiments, the ophthalmic system may limit transmission of the blue wavelengths within the above-defined ranges to substantially 1% of incident wavelengths. In still other embodiments, the ophthalmic system may limit transmission of the blue wavelengths within the above-defined ranges to substantially 0% of incident wavelengths. Stated otherwise, attenuation by the ophthalmic system of the electromagnetic spectrum at wavelengths in the above-specified ranges may be at least 10%; or at least 20%; or at least 30%; or at least 40%; or at least 50%; or at least 60%; or at least 70%; or at least 80%; or at least 90%; or at least 95%; or at least 99%; or substantially 100%.

In some cases it may be particularly desirable to filter a relatively small portion of the blue spectrum, such as the 400-460 nm region. For example, it has been found that blocking too much of the blue spectrum can interfere with scotopic vision and circadian rhythms. Conventional blue blocking ophthalmic lenses typically block a much larger amount of a wide range of the blue spectrum, which can adversely affect the wearer's "biological clock" and have other adverse effects. Thus, it may be desirable to block a relatively narrow range of the blue spectrum as described herein. Exemplary systems that may filter a relatively small amount of light in a relatively small range include system that block or absorb 5-50%, 5-20%, and 5-10% of light having a wavelength of 400-460 nm, 410-450 nm, and 420-440 nm.

At the same time as wavelengths of blue light are selectively blocked as described above, at least 80%, at least 85%, at least 90%, or at least 95% of other portions of the visual electromagnetic spectrum may be transmitted by the ophthalmic system. Stated otherwise, attenuation by the ophthalmic system of the electromagnetic spectrum at wavelengths outside the blue light spectrum, e.g. wavelengths other than those in a range around 430 nm may be 20% or less, 15% or less, 10% or less, and in other embodiments, 5% or less.

Additionally, embodiments of the present invention may further block ultra-violet radiation the UVA and UVB spectral bands as well as infra-red radiation with wavelengths greater than 700 nm.

Any of the above-disclosed ophthalmic system may be incorporated into an article of eyewear, including externally-worn eyewear such as eyeglasses, sunglasses, goggles or contact lenses. In such eyewear, because the blue-blocking component of the systems is posterior to the color balancing component, the blue-blocking component will always be closer to the eye than the color-balancing component when the eyewear is worn. The ophthalmic system may also be used in such articles of manufacture as surgically implantable intraocular lenses.

Several embodiments use a film to block the blue light. The film in an ophthalmic or other system may selectively inhibit at least 5%, at least 10%, at least 20%, at least 30%, at least 40%, and/or at least 50% of blue light within the 400-460 nm range. As used herein, a film "selectively inhibits" a wavelength range if it inhibits at least some transmission within the range, while having little or no effect on transmission of visible wavelengths outside the range. The film and/or a system incorporating the film may be color balanced to allow for being perception by an observer and/or user as colorless. Systems incorporating a film according to embodiments of the present invention may have a scotopic luminous transmission of 85% or better of visible light, and further allow someone looking through the film or system to have mostly normal color vision.

Figure 30:
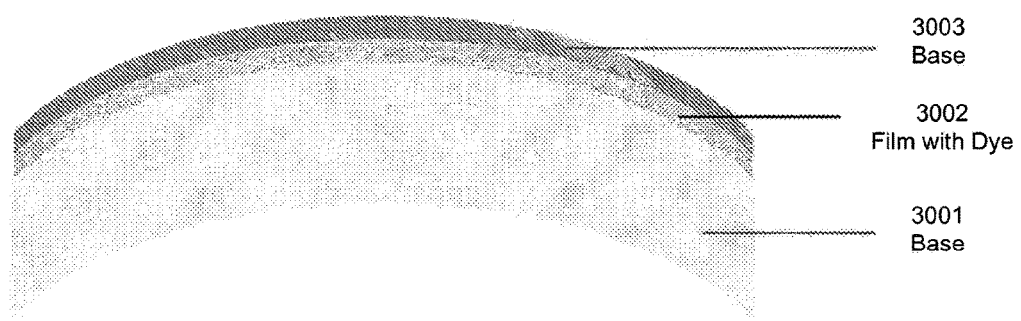
FIG. 30 shows an exemplary ophthalmic device comprising a film.

FIG. 30 shows an exemplary embodiment of the present invention. A film 3002 may be disposed between two layers or regions of one or more base materials 3001, 3003. As further described herein, the film may contain a dye that selectively inhibits certain wavelengths of light. The base material or materials may be any material suitable for a lens, ophthalmic system, window, or other system in which the film may be disposed.

Figure 31:
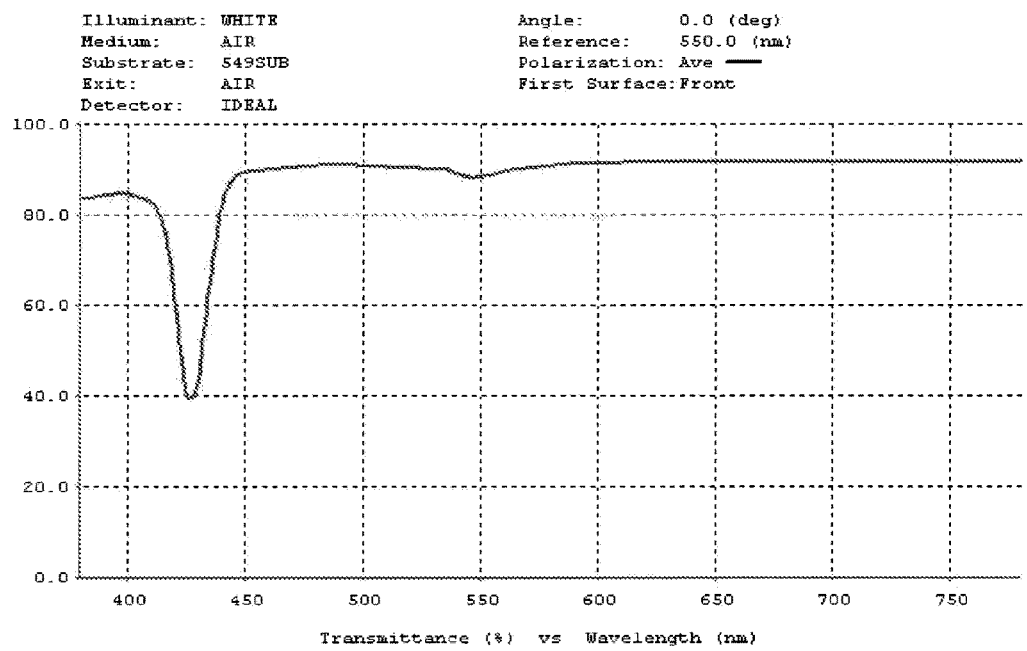
FIG. 31 shows the optical transmission characteristic of an exemplary film.

The optical transmission characteristic of an exemplary film according to an embodiment of the invention is shown in FIG. 31 where about 50% of blue light in the range of 430±10 nm is blocked, while imparting minimal losses on other wavelengths within the visible spectrum. The transmission shown in FIG. 31 is exemplary, and it will be understood that for many applications it may be desirable to selectively inhibit less than 50% of blue light, and/or the specific wavelengths inhibited may vary. It is believed that in many applications cell death may be reduced or prevented by blocking less than 50% of blue light. For example, it may be preferred to selectively inhibit about 40%, more preferably about 30%, more preferably about 20%, more preferably about 10%, and more preferably about 5% of light in the 400-460 nm range. Selectively inhibiting a smaller amount of light may allow for prevention of damage due to high-energy light, while being minimal enough that the inhibition does not adversely affect scotopic vision and/or circadian cycles in a user of the system.

Figure 32:
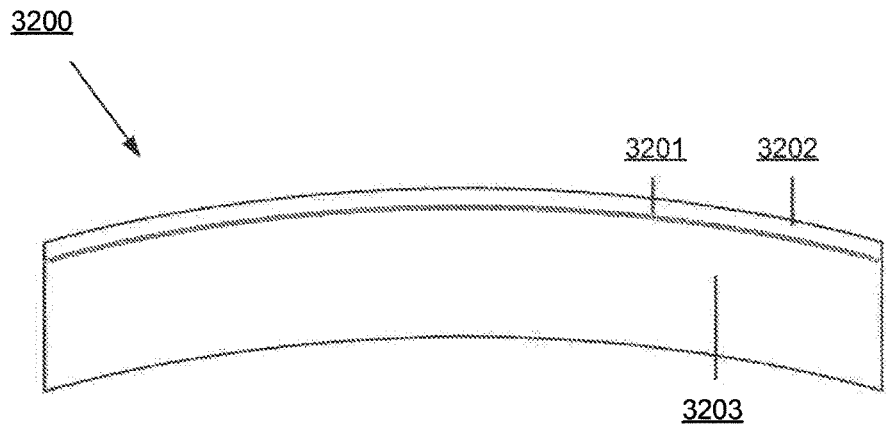
FIG. 32 shows an exemplary ophthalmic system comprising a film.

FIG. 32 shows a film 3201 incorporated into an ophthalmic lens 3200 according to an embodiment of the present invention, where it is sandwiched between layers of ophthalmic material 3202, 3203. The thickness of the front layer of ophthalmic material is, by way of example only, in the range of 200 microns to 1,000 microns.

Figure 33:
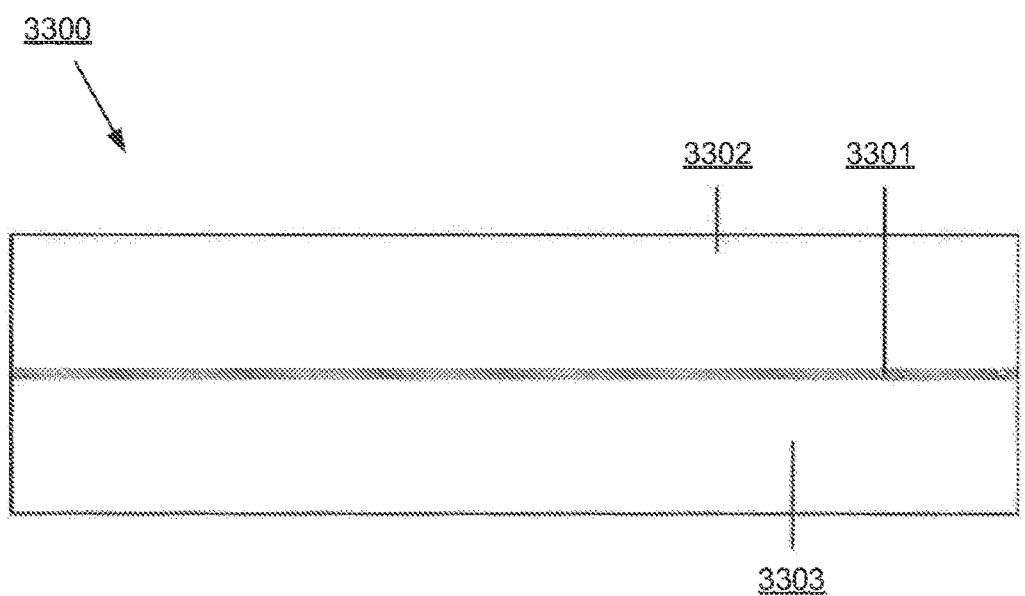
FIG. 33 shows an exemplary system comprising a film.

Similarly, FIG. 33 shows an exemplary system 3300, such as an automotive windshield, according to embodiments of the present invention. A film 3301 may be incorporated into the system 3300, where it is sandwiched between layers of base material 3302, 3303. For example, where the system 3300 is an automotive windshield, the base material 3302, 3303 may be windshield glass as is commonly used. It will be understood that in various other systems, including visual, display, ophthalmic, and other systems, different base materials may be used without departing from the scope of embodiments of the present invention.

In an embodiment, a system according to the invention may be operated in an environment where the relevant emitted visible light has a very specific spectrum. In such a regime, it may be desirable to tailor a film's filtering effect to optimize the light transmitted, reflected, or emitted by the item. This may be the case, for example, where the color of the transmitted, reflected, or emitted light is of primary concern. For example, when a film according to embodiments of the present invention is used in or with a camera flash or flash filter, it may be desirable for the perceived color of the image or print to be as close to true color as possible. As another example, a film according to embodiments of the present invention may be used in instrumentation for observing the back of a patient's eye for disease. In such a system, it may be preferable for the film not to interfere with the true and observed color of the retina. As another example, certain forms of artificial lighting may benefit from a wavelength-customized filter utilizing the inventive film.

In an embodiment, the inventive film may be utilized within a photochromatic, electro-chromic, or changeable tint ophthalmic lens, window or automotive windshield. Such a system may allow for protection from UV light wavelengths, direct sunlight intensity, and blue light wavelengths in an environment where the tinting is not active. In this embodiment the film's blue light wavelengths protective attributes may be effective regardless of whether the tinting is active.

In an embodiment, a film may allow for selective inhibition of blue light while being color balanced and will have an 85% or greater scotopic luminous transmission of visible light. Such a film may be useful for lower light transmission uses such as driving glasses or sport glasses, and may provide increased visual performance due to increased contrast sensitivity.

For some applications, it may be desirable for a system according to the present embodiments of the to electively inhibit blue light as described herein, and have a luminous transmission of less than about 85%, typically about 80-85%, across the visible spectrum. This may be the case where, for example, a base material used in the system inhibits more light across all visible wavelengths due to its higher index of refraction. As a specific example, high index (e.g., 1.7) lenses may reflect more light across wavelengths leading to a luminous transmission less than 85%.

To avoid, reduce, or eliminate problems present in conventional blue-blocking systems, it may be desirable to reduce, but not eliminate, transmission of phototoxic blue light. The pupil of the eye responds to the photopic retinal illuminance, in trolands, which is the product of the incident flux with the wavelength-dependent sensitivity of the retina and the projected area of the pupil. A filter placed in front of the retina, whether within the eye, as in an intraocular lens, attached to the eye, as in a contact lens or corneal replacement, or otherwise in the optical path of the eye as in a spectacle lens, may reduce the total flux of light to the retina and stimulate dilation of the pupil, and thus compensate for the reduction in field illuminance. When exposed to a steady luminance in the field the pupil diameter generally fluctuates about a value that increases as the luminance falls.

A functional relationship between pupil area and field illuminance described by Moon and Spencer, J. Opt. Soc. Am. v. 33, p. 260 (1944) using the following equation for pupil diameter:

$$d = 4.9 - 3 \tan h(\text{Log}(L)+1) \tag{0.1}$$

where d is in millimeters and L is the illuminance in cd/m². FIG. 34A shows pupil diameter (mm) as a function of field illuminance (cd/m²). FIG. 34B shows pupil area (mm²) as a function of field illuminance.

The illuminance is defined by the international CIE standards as a spectrally weighted integration of visual sensitivity over wavelength:

$$L = K_m \int L_{e,\lambda} V_\lambda d\lambda \text{ photopic}$$

$$L' = K'_m \int L_{e,\lambda} V'_\lambda d\lambda \text{ scotopic} \tag{0.2}$$

where K'm is equal to 1700.06 lm/W for scotopic (night) vision, $K_m = 683.2$ lm/W for photopic (day) vision and the spectral luminous efficiency functions $V_\lambda$ and $V'_\lambda$ define the standard photopic and scotopic observers. The luminous efficiency functions $V_\lambda$ and $V'_\lambda$ are illustrated in, e.g., FIG. 9 of Michael Kalloniatis and Charles Luu, "Psychophysics of Vision," available at http://webvision.med.utah.edu/Phychl. html, last visited Aug. 8, 2007, which is incorporated by reference herein.

Interposition of an absorptive ophthalmic element in the form of an intraocular, contact, or spectacle lens reduces the illuminance according to the formula:

$$L = K_m \int T_\lambda L_{e,\lambda} V_\lambda d\lambda \text{ photopic}$$

$$L' = K'_m \int T_\lambda L_{e,\lambda} V'_\lambda d\lambda \text{ scotopic} \tag{0.3}$$

where $T_\lambda$ is the wavelength-dependent transmission of the optical element. Values for the integrals in equation 1.3 normalized to the unfiltered illuminance values computed from equation 1.2 for each of the prior-art blue blocking lenses are shown in Table I.

TABLE I

| Reference | FIG. | Photopic Ratio | Scotopic Ratio |
|---|---|---|---|
| Unfiltered | | 1.000 | 1.000 |
| Pratt '430 | | 0.280 | 0.164 |
| Mainster 2005/0243272 | | 0.850 | 0.775 |
| Present System | 35 | 0.996 | 0.968 |
| Present System | 36 (solid line) | 0.993 | 0.947 |
| Present System | 37 | 0.978 | 0.951 |

Referring to Table I, the ophthalmic filter according to Pratt reduces scotopic sensitivity by 83.6% of its unfiltered value, an attenuation that will both degrade night vision and stimulate pupil dilation according to equation 1.1. The device described by Mainster reduces scotopic flux by 22.5%, which is less severe than the Pratt device but still significant.

In contrast, a film according to embodiments of the present invention partially attenuates violet and blue light using absorptive or reflective ophthalmic elements while reducing the scotopic illuminance by no more than 15% of its unfiltered value. Surprisingly, systems according to embodiments of the present invention were found to selectively inhibit a desired region of blue light, while having little to no effect on photopic and scotopic vision.

Figure 35:
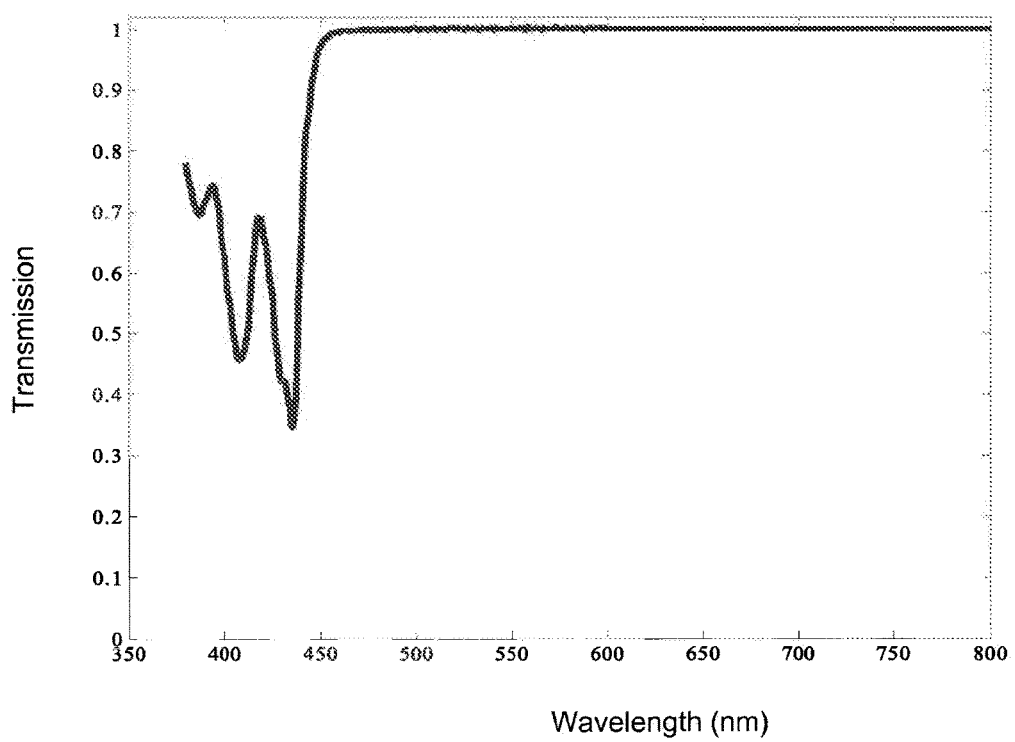
FIG. 35 shows the transmission spectrum of a film that is doped with perylene dye where the product of concentration and path length yield about 33% transmission at about 437 nm.
Figure 36:
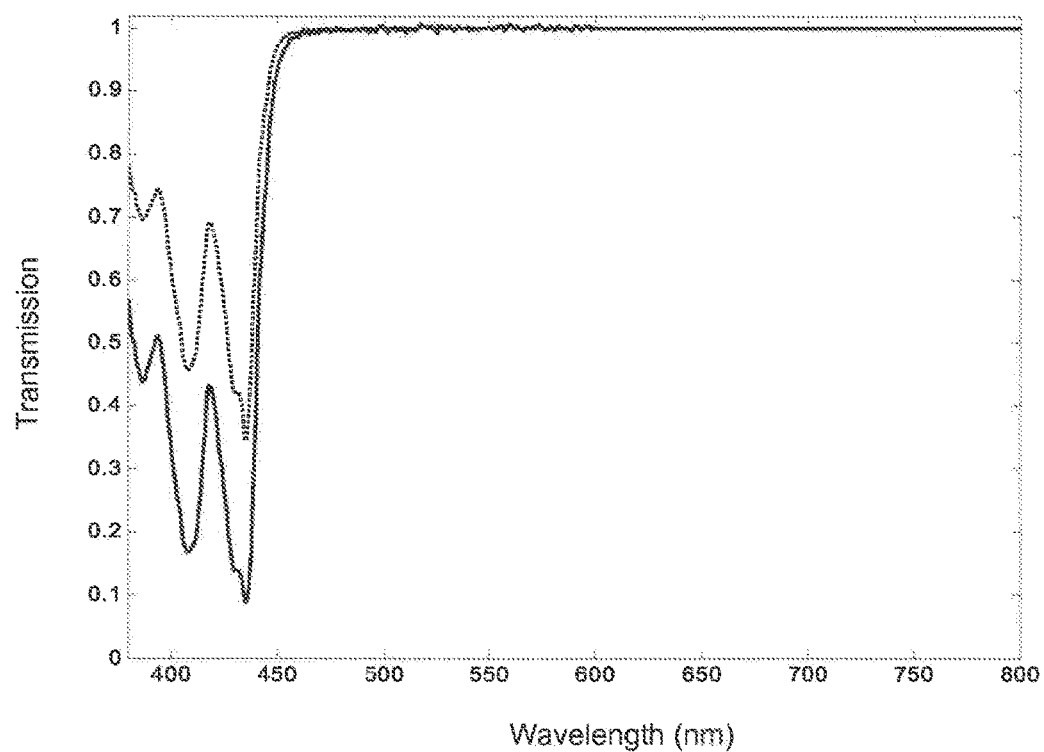
FIG. 36 shows the transmission spectrum of a film according to the present invention with a perylene concentration about 2.27 times higher than that illustrated in the previous figure.

In an embodiment, perylene (C20HI2, CAS #19855-0) is incorporated into an ophthalmic device at a concentration and thickness sufficient to absorb about two thirds of the light at its absorption maximum of 437 nm. The transmission spectrum of this device is shown in FIG. 35. The change in illuminance that results from this filter is only about 3.2% for scotopic viewing conditions and about 0.4% under photopic viewing conditions, as displayed in Table I. Increasing the concentration or thickness of perylene in the device decreases the transmission at each wavelength according to Beer's law. FIG. 36 shows the transmission spectrum of a device with a perylene concentration 2.27 times higher than that for FIG. 6. Although this device selectively blocks more of the phototoxic blue light than the device in FIG. 6, it reduces scotopic illuminance by less than 6% and photopic illuminance by less than 0.7%. Note that reflection has been removed from the spectra in FIGS. 35 and 36 to show only the effect of absorption by the dye.

Dyes other than perylene may have strong absorption in blue or roughly blue wavelength ranges and little or no absorbance in other regions of the visible spectrum. Examples of such dyes, illustrated in FIG. 46, include porphyrin, coumarin, and acridine based molecules which may be used singly or in combination to give transmission that is reduced, but not eliminated, at 400-460 nm. The methods and systems described herein therefore may use similar dyes based on other molecular structures at concentrations that mimic the transmission spectra of perylene, porphyrin, coumarin, and acridine.

The insertion of dye into the optical path according to embodiments of the present invention may be accomplished by diverse methods familiar to those practiced in the art of optical manufacturing. The dye or dyes may be incorporated directly into the substrate, added to a polymeric coating, imbibed into the lens, incorporated in a laminated structure that includes a dye-impregnated layer, or as a composite material with dye-impregnated microparticles.

Figure 37:
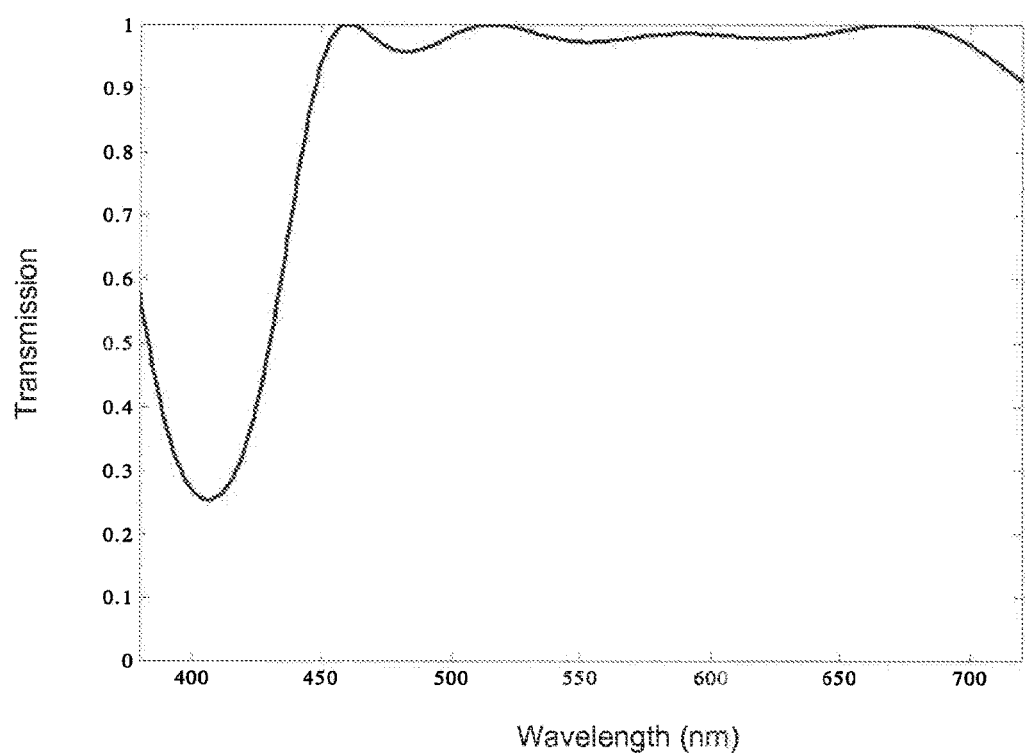
FIG. 37 shows an exemplary transmission spectrum for a six-layer stack of SiO$_2$ and ZrO$_2$.

According to another embodiment of the invention a dielectric coating that is partially reflective in the violet and blue spectral regions and antireflective at longer wavelengths may be applied. Methods for designing appropriate dielectric optical filters are summarized in textbooks such as Angus McLeod, Thin Film Optical Filters (McGraw-Hill: NY) 1989. An exemplary transmission spectrum for a six-layer stack of $SiO_2$ and $ZrO_2$ according to the present invention is shown in FIG. 37. Referring again to Table 1, it is seen that this optical filter blocks phototoxic blue and violet light while reducing scotopic illuminance by less than 5% and photopic illuminance by less than 3%.

Although many conventional blue blocking technologies attempt to inhibit as much blue light as possible, current research suggests that in many applications it may be desirable to inhibit a relatively small amount of blue light. For example, to prevent undesirable effects on scotopic vision, it may be desirable for an ophthalmic system according to embodiments of the invention to inhibit only about 30% of blue (i.e., 380-500 nm) wavelength light, or more preferably only about 20% of blue light, more preferably about 10%, and more preferably about 5%. It is believed that cell death may be reduced by inhibiting as little as 5% of blue light, while this degree of blue light reduction has little or no effect on scotopic vision and/or circadian behavior of those using the system.

As used herein, a film according to embodiments of the invention that selectively inhibits blue light is described as inhibiting an amount of light measured relative to the base system incorporating the film. For example, an ophthalmic system may use a polycarbonate or other similar base for a lens. Materials typically used for such a base may inhibit a various amount of light at visible wavelengths. If a blue-blocking film according to embodiments of the present invention is added to the system, it may selectively inhibit 5%, 10%, 20%, 30%, 40%, and/or 50% of all blue wavelengths, as measured relative to the amount of light that would be transmitted at the same wavelength(s) in the absence of the film.

The methods and devices disclosed herein may minimize, and preferably eliminate, the shift in color perception that results from blue-blocking. The color perceived by the human visual system results from neural processing of light signals that fall on retinal pigments with different spectral response characteristics. To describe color perception mathematically, a color space is constructed by integrating the product of three wavelength-dependent color matching functions with the spectral irradiance. The result is three numbers that characterize the perceived color. A uniform (L*, a*, b*) color space, which has been established by the Commission Internationale de L'eclairage (CIE), may be used to characterize perceived colors, although similar calculations based on alternative color standards are familiar to those practiced in the art of color science and may also be used. The (L*, a*, b*) color space defines brightness on the L* axis and color within the plane defined by the a* and b* axes. A uniform color space such as that defined by this CIE standard may be preferred for computational and comparative applications, since the Cartesian distances of the space are proportional to the magnitude of perceived color difference between two objects. The use of uniform color spaces generally is recognized in the art, such as described in Wyszecki and Stiles, Color Science: Concepts and Methods, Quantitative Data and Formulae (Wiley: New York) 1982.

Figure 38:
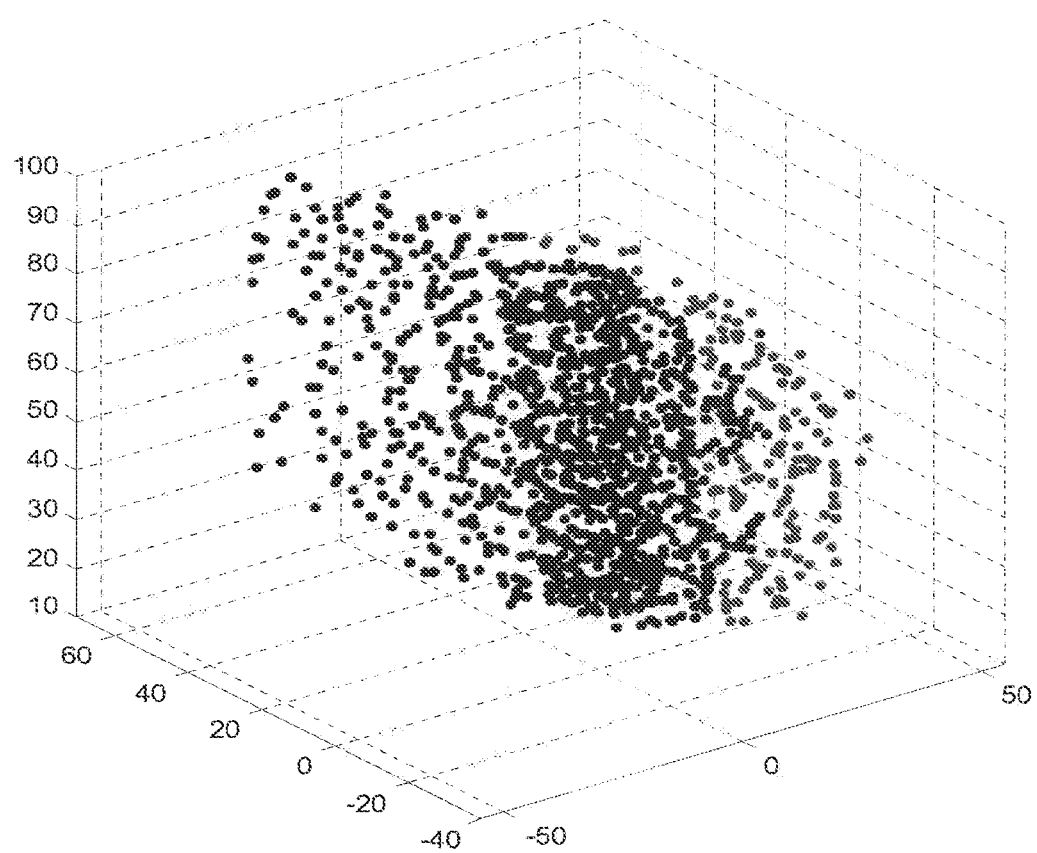
FIG. 38 shows reference color coordinates corresponding to Munsell tiles illuminated by a prescribed illuminant in (L*, a*, b*) color space.
Figure 39A:
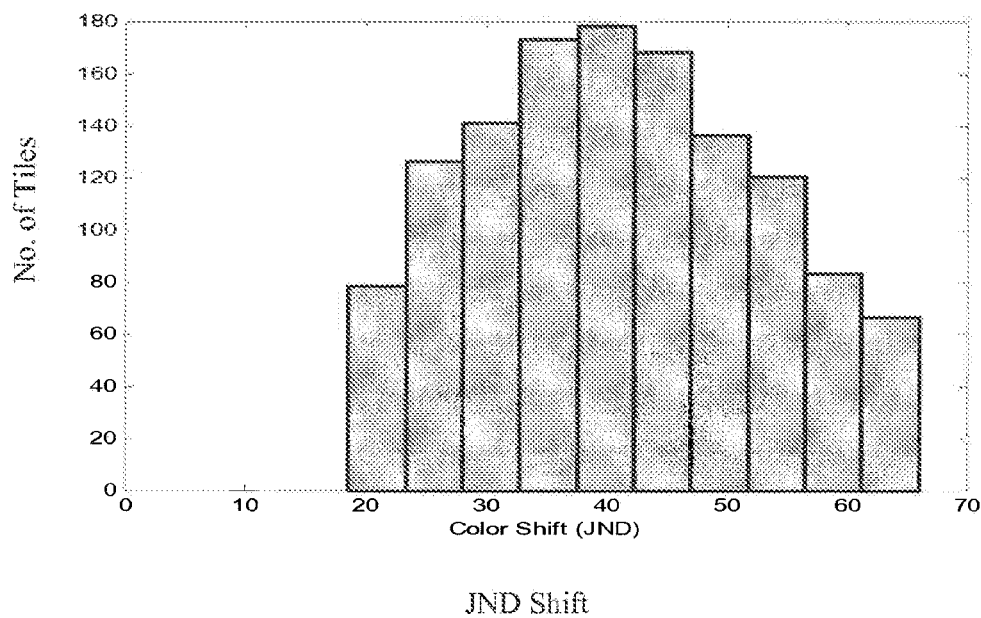
FIG. 39A shows a histogram of the color shifts for Munsell color tiles for a related filter.

An optical design according to the methods and systems described herein may use a palette of spectra that describe the visual environment. A non-limiting example of this is the Munsell matte color palette, which is comprised of 1,269 color tiles that have been established by psycho-physical experiments to be just noticeably different from each other. The spectral irradiance of these tiles is measured under standard illumination conditions. The array of color coordinates corresponding to each of these tiles illuminated by a D65 daylight illuminant in (L*, a*, b*) color space is the reference for color distortion and is shown in FIG. 38. The spectral irradiance of the color tiles is then modulated by a blue-blocking filter and a new set of color coordinates is computed. Each tile has a perceived color that is shifted by an amount corresponding to the geometric displacement of the (L*, a*, b*) coordinates. This calculation has been applied to the blue-blocking filter of Pratt, where the average color distortion is 41 just noticeable difference (JND) units in (L*, a*, b*) space. The minimum distortion caused by the Pratt filter is 19 JNDs, the maximum is 66, and the standard deviation is 7 JNDs. A histogram of the color shifts for all 1,269 color tiles is shown in FIG. 39A (top).

Figure 39B:
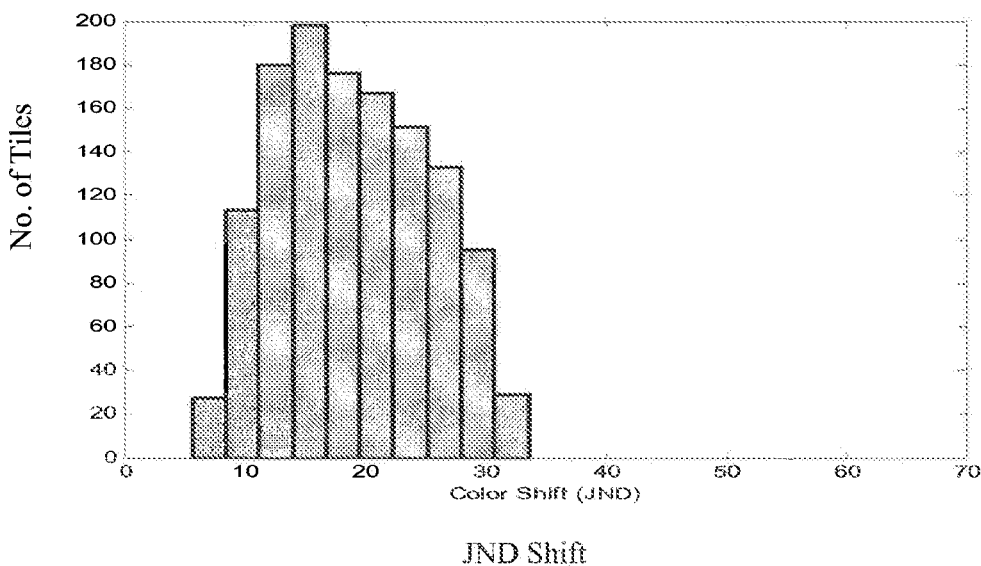
FIG. 39B shows a color shift induced by a related blue-blocking filter.

Referring now to FIG. 39B, the color shift induced by the Mainster blue-blocking filter has a minimum value of 6, an average of 19, a maximum of 34, and a standard deviation of 6 JNDs.

Embodiments of the present invention using perylene dye at two concentrations or the reflective filter described above may have substantially smaller color shifts than conventional devices whether measured as an average, minimum, or maximum distortion, as illustrated in Table II.

Figure 40:
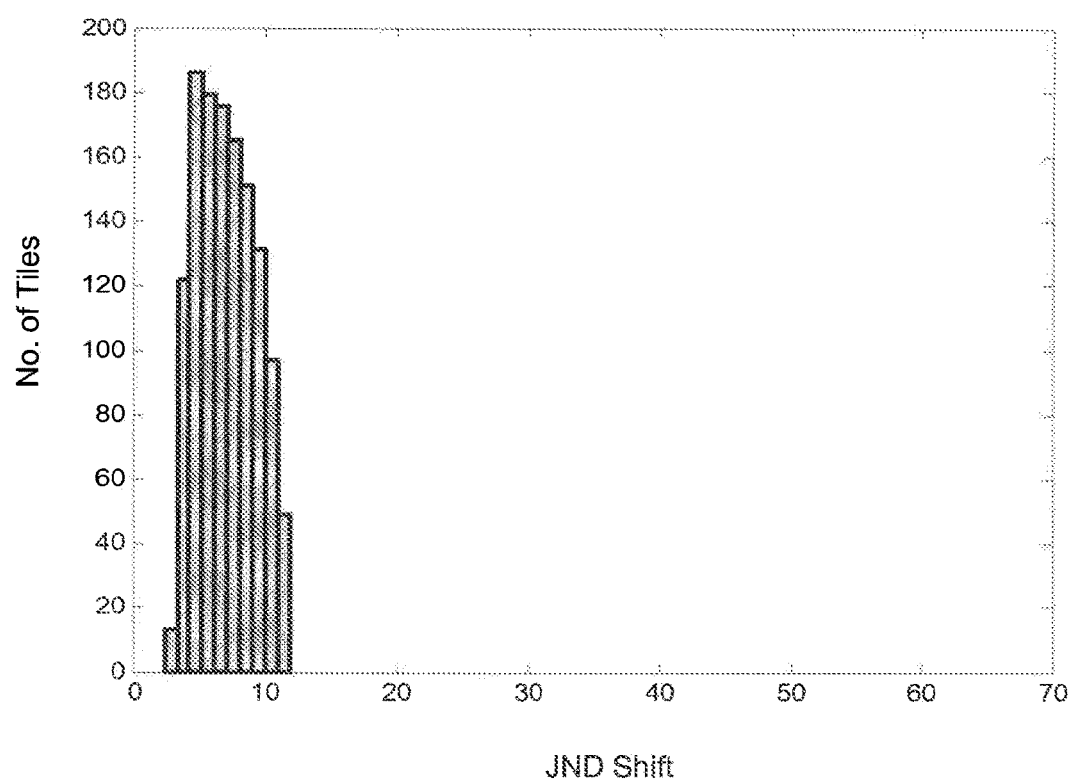
FIG. 40 shows a histogram of color shifts for a perylene-dyed substrate according to the present invention.

FIG. 40 shows a histogram of color shifts for a perylene-dyed substrate according to embodiments of the present invention whose transmission spectrum is shown in FIG. 35. Notably, the shift across all color tiles was observed to be substantially lower and narrower than those for conventional devices described by Mainster, Pratt, and the like. For example, simulation results showed (L*, a*, b*) shifts as low as 12 and 20 JNDs for films according to embodiments of the present invention, with average shifts across all tiles as low as 7-12 JNDs.

TABLE II

| Reference | FIG. | Avg. δ (L*, a*, b*) | Min. δ (L*, a*, b*) | Max. δ (L*, a*, b*) | Std. Deviation δ (L*, a*, b*) |
|---|---|---|---|---|---|
| Pratt | | 41 | 19 | 66 | 12 |
| Mainster | | 19 | 6 | 34 | 6 |
| Present System | 35 | 7 | 2 | 12 | 2 |
| Present System | 36 | 12 | 4 | 20 | 3 |
| Present System | 37 | 7 | 2 | 12 | 2 |

Figure 41:
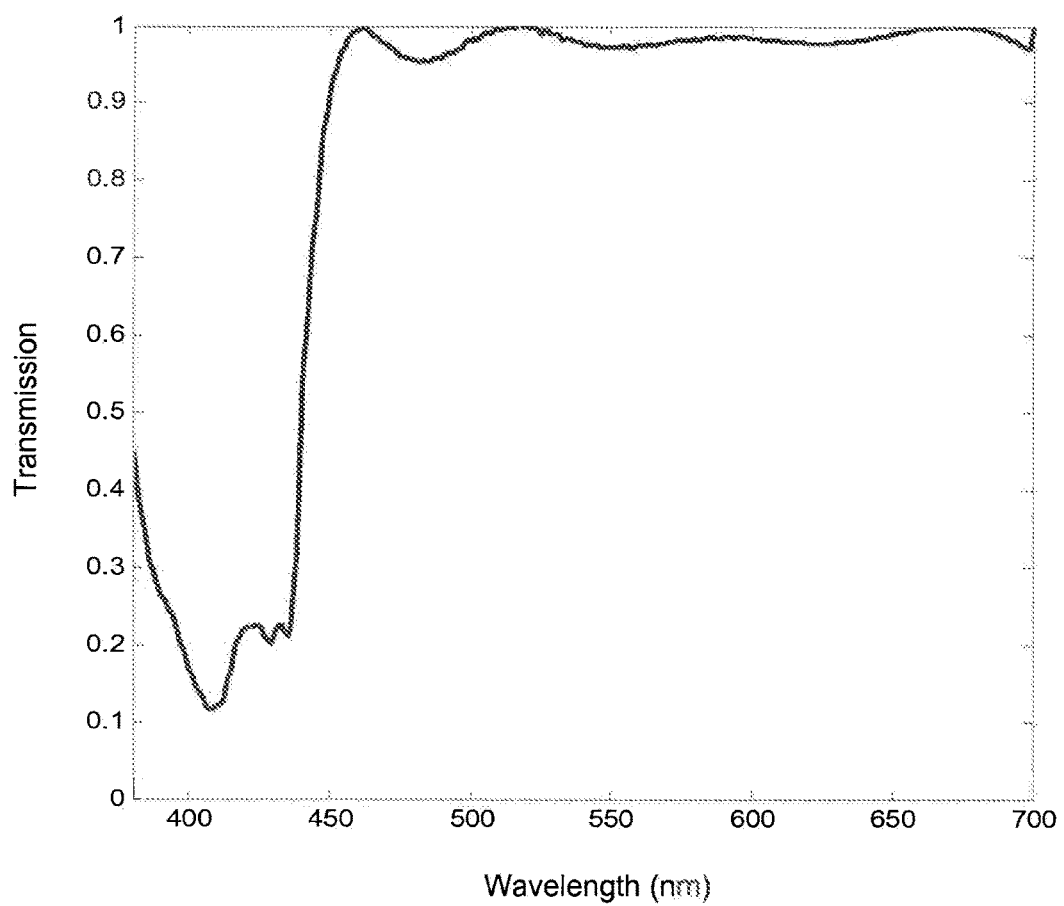
FIG. 41 shows the transmission spectrum of a system according to the present invention.
Figure 42:
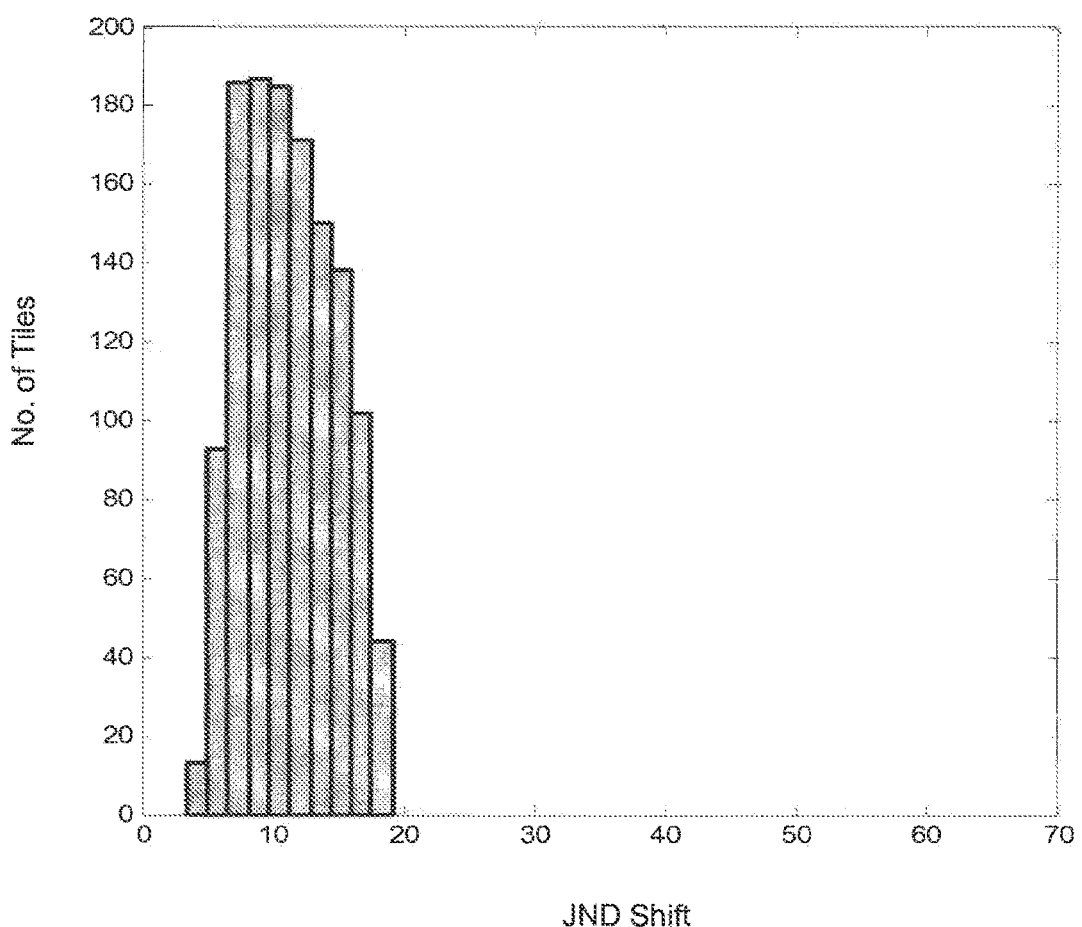
FIG. 42 shows a histogram summarizing color distortion of a device according to the present invention for Munsell tiles in daylight.

In an embodiment, a combination of reflective and absorptive elements may filter harmful blue photons while maintaining relatively high luminous transmission. This may allow a system according to embodiments of the invention to avoid or reduce pupil dilation, preserve or prevent damage to night vision, and reduce color distortion. An example of this approach combines the dielectric stacks shown in FIG. 37 with the perylene dye of FIG. 35, resulting in the transmission spectrum shown in FIG. 41. The device was observed to have a photopic transmission of 97.5%, scotopic transmission of 93.2%, and an average color shift of 11 JNDs. The histogram summarizing color distortion of this device for the Munsell tiles in daylight is shown in FIG. 42.

Figure 43A:
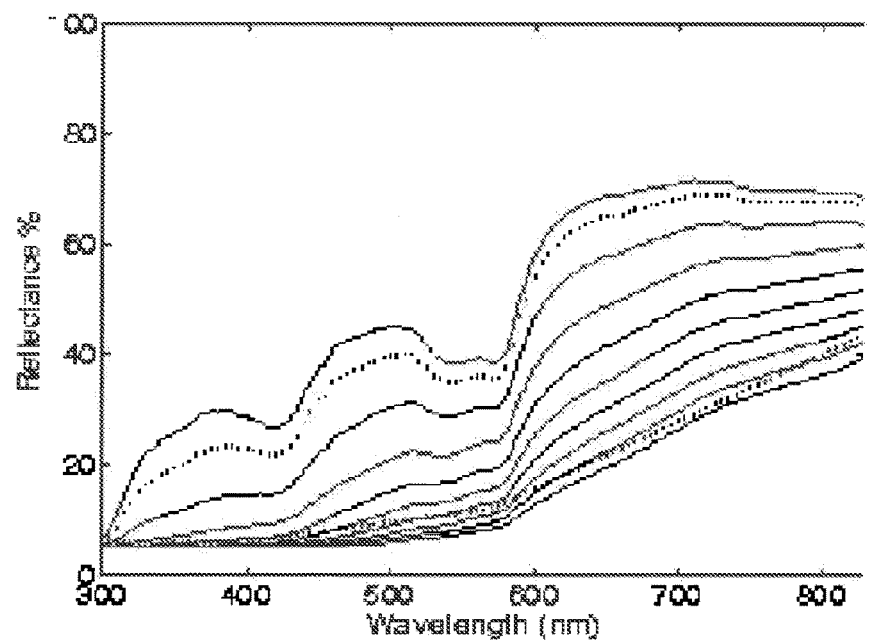
FIG. 43A shows representative series of skin reflectance spectra from subjects of different races.
Figure 43B:
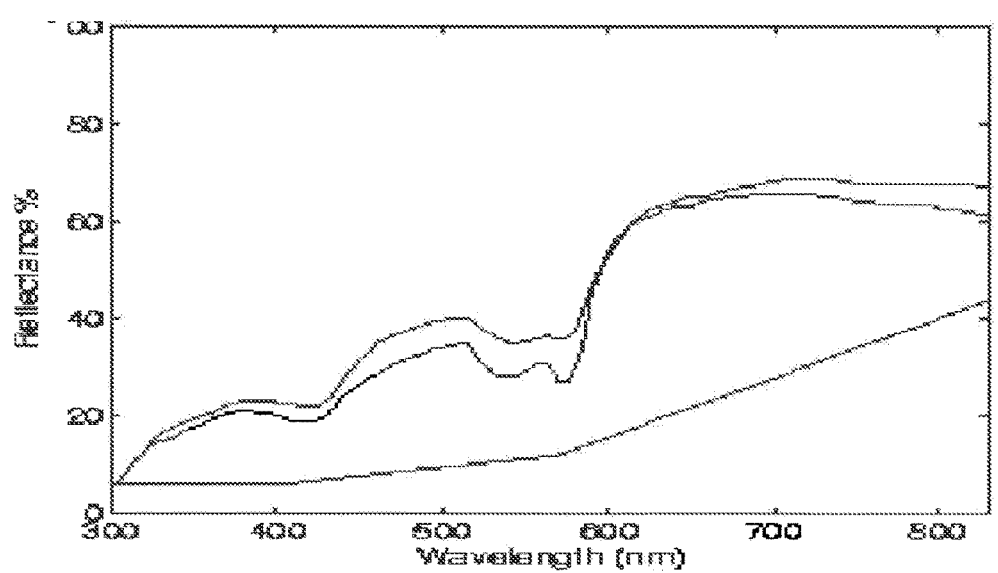
FIG. 43B shows another representative series of skin reflectance spectra from subjects of different races.
Figure 44:
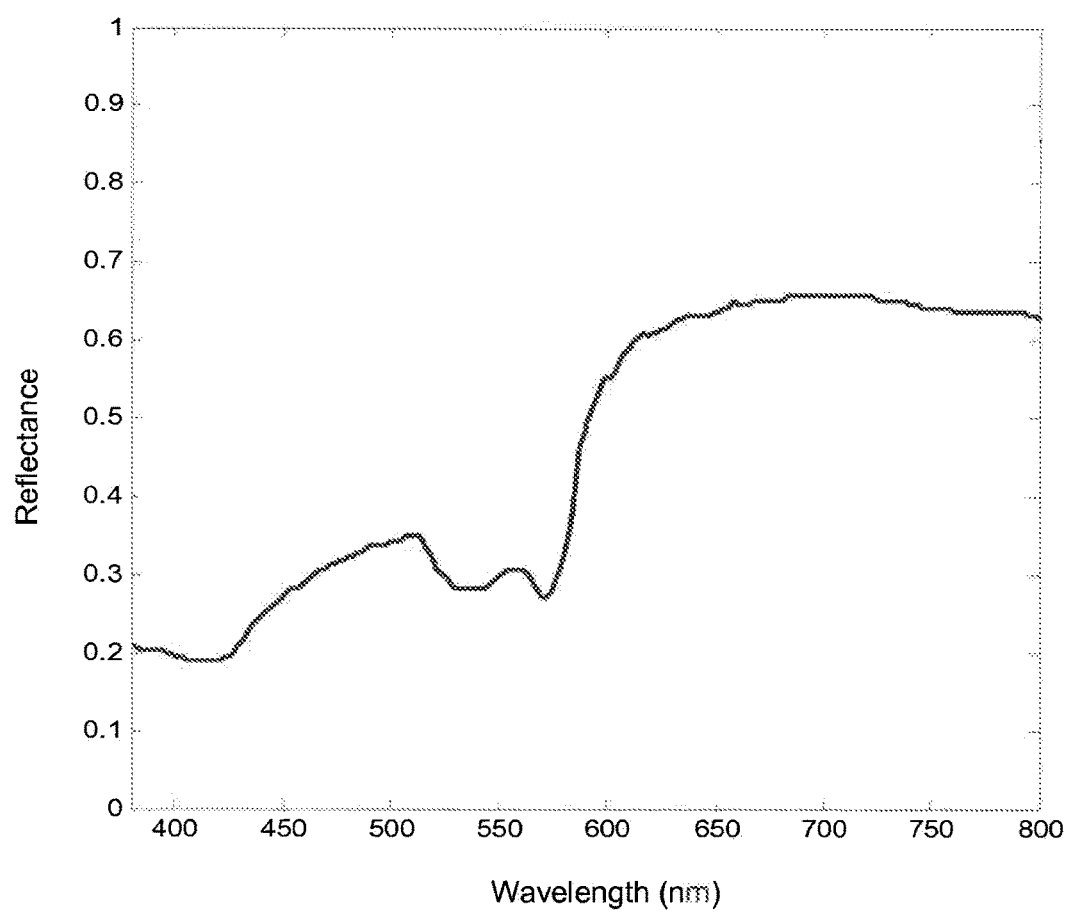
FIG. 44 shows an exemplary skin reflectance spectrum for a Caucasian subject.

In another embodiment, an ophthalmic filter is external to the eye, for example a spectacle lens, goggle, visor, or the like. When a traditional filter is used, the color of the wearer's face when viewed by an external observer may be tinted by the lens, i.e., the facial coloration or skin tone typically is shifted by a blue-blocking lens when viewed by another person. This yellow discoloration that accompanies blue light absorption is often not cosmetically desirable. The procedure for minimizing this color shift is identical to that described above for the Munsell tiles, with the reflectance of the wearer's skin being substituted for those of the Munsell color tiles. The color of skin is a function of pigmentation, blood flow, and the illumination conditions. A representative series of skin reflectance spectra from subjects of different races is shown in FIGS. 43A-B. An exemplary skin reflectance spectrum for a Caucasian subject is shown in FIG. 44. The (L*, a*, b*) color coordinates of this skin in daylight (D65) illumination are (67.1, 18.9, 13.7). Interposition of the Pratt blue-blocking filter changes these color coordinates to (38.9, 17.2, 44.0), a shift of 69 JND units. The Mainster blue-blocking filter shifts the color coordinates by 17 JND units to (62.9, 13.1, 29.3). By contrast, a perylene filter as described herein causes a color shift of only 6 JNDs, or one third that of the Mainster filter. A summary of the cosmetic color shift of an exemplary Caucasian skin under daylight illumination using various blue-blocking filters is shown in Table III. The data shown in Table I refer are normalized to remove any effect caused by a base material.

TABLE III

| Reference | FIG. | L* | a* | b* | δ(L*, a*, b*) |
|---|---|---|---|---|---|
| Skin | 14-15 | 67 | 19 | 14 | 0 |
| Pratt | | 39 | 17 | 44 | 69 |
| Mainster | | 63 | 13 | 29 | 17 |
| Present System. | 35 | 67 | 17 | 19 | 6 |
| Present System | 36 | 67 | 15 | 23 | 10 |
| Present System | 37 | 67 | 17 | 19 | 6 |

In an embodiment, an illuminant may be filtered to reduce but not eliminate the flux of blue light to the retina. This may be accomplished with absorptive or reflective elements between the field of view and the source of illumination using the principles described herein. For example, an architectural window may be covered with a film that contains perylene so that the transmission spectrum of the window matches that shown in FIG. 35. Such a filter typically would not induce pupil dilation when compared to an uncoated window, nor would it cause appreciable color shifts when external daylight passes through it. Blue filters according to embodiments of the present invention may be used on artificial illuminants such as fluorescent, incandescent, arc, flash, and diode lamps, displays, and the like.

Various materials may be used in making films according to embodiments of the invention. Two such exemplary materials are Poly Vinyl Alcohol (PVA) and Poly Vinyl Butyral (PVB). In the case of PVA film it may be prepared by partial or complete hydrolysis of polyvinyl acetate to remove the acetate groups. PYA film may be desirable due to beneficial film forming, emulsifying, and adhesive properties. In addition, PYA film has high tensile strength, flexibility, high temperature stability, and provides an excellent oxygen barrier.

PVB film may be prepared from a reaction of polyvinyl alcohol in butanal. PVB may be suitable for applications where high strength, optical clarity, flexibility and toughness is preferred. PVB also has excellent film forming and adhesive properties.

PYA, PVB, and other suitable films may be extruded, cast from a solution, spin coated and then cured, or dip coated and then cured. Other manufacturing methods known in the art also may be used. There are several ways of integrating the dyes needed to create the desired spectral profile of the film. Exemplary dye-integration methods include vapor deposition, chemically cross linked within the film, dissolved within small polymer micro-spheres and then integrated within the film. Suitable dyes are commercially available from companies including Keystone, BPI & Phantom.

Most dyeing of spectacle lenses is done after the lens has been shipped from the manufacturer. Therefore, it may be desirable to incorporate a blue-absorbing dye during the manufacture of the lens itself. To do so, the filtering and color balancing dyes may be incorporated into a hard coating and/or an associated primer coating which promotes adhesion of the hard coating to the lens material. For example, a primer coat and associated hard coat are often added to the top of a spectacle lens or other ophthalmic system at the end of the manufacturing process to provide additional durability and scratch resistance for the final product. The hard coat typically is an outer-most layer of the system, and may be placed on the front, back, or both the front and back surfaces of the system.

Figure 47:
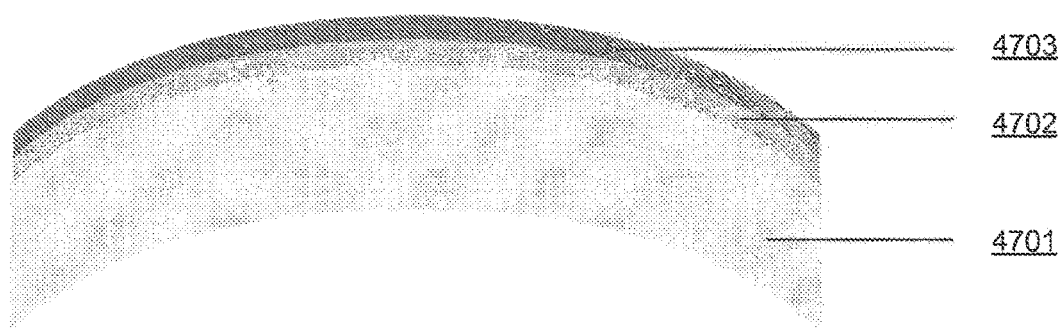
FIG. 47 shows an ophthalmic system having a hard coat.

FIG. 47 shows an exemplary system having a hard coating 4703 and its associated adhesion-promoting primer coat 4702. Exemplary hard coatings and adhesion promoting primer coating are available from manufacturers such as Tokuyama, UltraOptics, SDC, PPG, and LTI.

In systems according to embodiments of the invention, both a blue blocking dye and a color balancing dye may be included in the primer coating 1802. Both the blue blocking and color balancing dyes also may be included in the hard coating 1803. The dyes need not be included in the same coating layer. For example, a blue blocking dye may be included in the hard coating 1803, and a color balancing dye included in the primer coating 1802. The color balancing dye may be included in the hard coating 1803 and the blue blocking dye in the primer coating 1802.

Primer and hard coats according to embodiments of the invention may be deposited using methods known in the art, including spin-coating, dip-coating, spray-coating, evaporation, sputtering, and chemical vapor deposition. The blue blocking and/or color balancing dyes to be included in each layer may be deposited at the same time as the layer, such as where a dye is dissolved in a liquid coating material and the resulting mixture applied to the system. The dyes also may be deposited in a separate process or sub-process, such as where a dye is sprayed onto a surface before the coat is cured or dried or applied.

A hard coat and/or primer coat may perform functions and achieve benefits described herein with respect to a film. Specifically, the coat or coats may selectively inhibit blue light, while maintaining desirable photopic vision, scotopic vision, circadian rhythms, and phototoxicity levels. Hard coats and/or primer coats as described herein also may be used in an ophthalmic system incorporating a film as described herein, in any and various combinations. As a specific example, an ophthalmic system may include a film that selectively inhibits blue light and a hard coat that provides color correction.

The selective filter of embodiments of the present invention can also provide increased contrast sensitivity. Such a system functions to selectively filter harmful invisible and visible light while having minimal effect on photopic vision, scotopic vision, color vision, and/or circadian rhythms while maintaining acceptable or even improved contrast sensitivity. Embodiments of the invention can be formulated such that in certain embodiments the end residual color of the device to which the selective filter is applied is mostly colorless, and in other embodiments where a mostly clear residual color is not required the residual color can be yellowish. Preferably, the yellowness of the selective filter is unobjectionable to the subjective individual wearer. Yellowness can be measured quantitatively using a yellowness index such as ASTM E313-05. Preferably, the selective filter has a yellowness index that is no more than 50, 40, 35, 30, 25, 23, 20, 15, 10, 9, 7, or 5.

Embodiments of the invention could include selective light wavelength filtering embodiments such as: windows, automotive windshields, light bulbs, flash bulbs, fluorescent lighting, LED lighting, television, computer monitors, etc. Any light that impacts the retina can be selectively filtered by embodiments of the invention. Embodiments of the invention can be enabled, by way of example only, a film comprising a selective filtering dye or pigment, a dye or pigment component added after a substrate is fabricated, a dye component that is integral with the fabrication or formulation of the substrate material, synthetic or non-synthetic pigment such as melanin, lutein, or zeaxanthin, selective filtering dye or pigment provided as a visibility tint (having one or more colors) as in a contact lens, selective filtering dye or pigment provided in an ophthalmic scratch resistant coating (hard coat), selective filtering dye or pigment provided in an ophthalmic anti-reflective coat, selective light wave length filtering dye or pigment provided in a hydrophobic coating, an interference filter, selective light wavelength filter, selective light wavelength filtering dye or pigment provided in a photochromic lens, or selective light wavelength filtering dye or pigment provided in a matrix of a light bulb or tube. It should be pointed out that embodiments of the invention contemplates the selective light wavelength filter selectively filtering out one specific range of wavelengths, or multiple specific ranges of wavelengths, but never filtering out wavelengths evenly across the visible spectrum.

Those skilled in the art will know readily how to provide the selective light wavelength filter to the substrate material. By way of example only, the selective filter can be: imbibed, injected, impregnated, added to the raw materials of the substrate, added to the resin prior to polymerization, layered within in the optical lens by way of a film comprising the selective filter dye or pigments.

Figure 48:
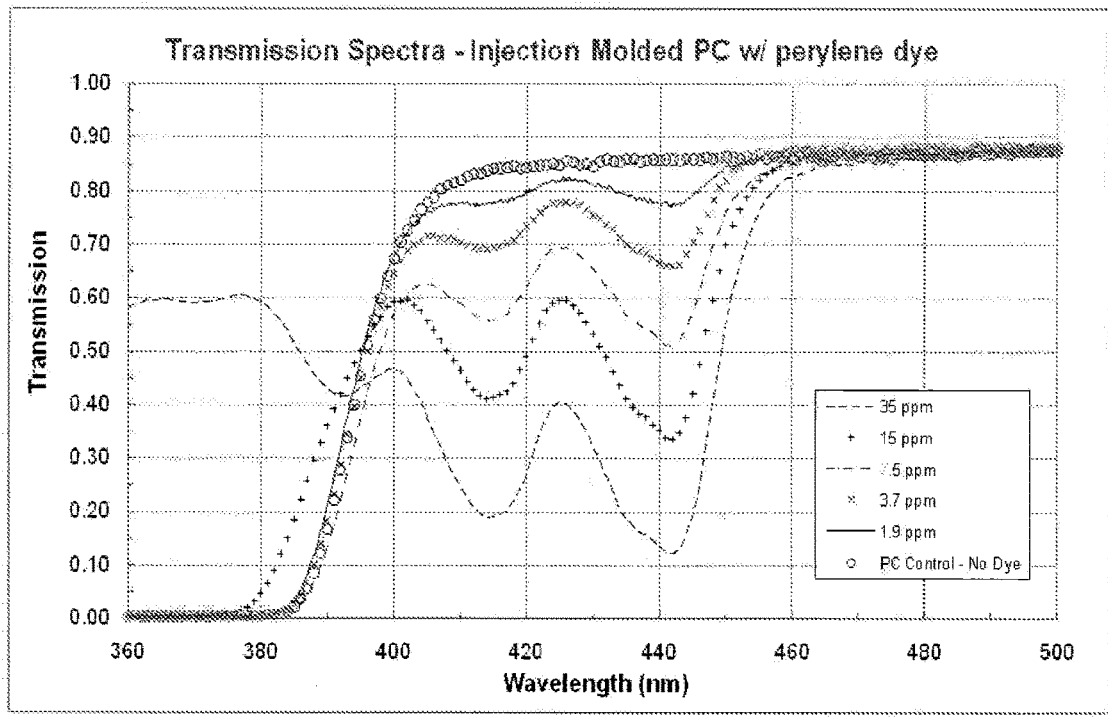
FIG. 48 shows the transmittance as a function of wavelength for a selective filter with strong absorption band around 430 nm.

Embodiments of the invention may utilize a proper concentration of a dye and or pigment such as, by way of example only, perylene, porphrin or their derivatives. Refer to FIG. 48 to observe varying concentration of perylene and the functional ability to block wavelengths of light at around 430 nm. The transmission level can be controlled by dye concentration. Other dye chemistries allow adjustment of the absorption peak positions.

Perylene with appropriate concentration levels provides balance in photopic, scotopic, circadian, and phototoxicity ratios while maintaining a mostly colorless appearance:

TABLE IV

| Reference | Photopic Ratio - $V_\lambda$ (%) | Scotopic Ratio - $V'_\lambda$ (%) | Phototoxicity Ratio ($B_\lambda$) (%) | Circadian Ratio ($M'_\lambda$) (%) |
|---|---|---|---|---|
| Unfiltered | 100 | 100 | 100 | 100 |
| Polycarbonate - undyed | 88 | 87 | 86 | 74 |
| Pratt | 28 | 16 | 4 | 7 |
| Mainster | 86 | 78 | 39 | 46 |
| Mainster (−20 nm shift) | 86 | 83 | 63 | 56 |
| Mainster (+20 nm shift) | 84 | 68 | 15 | 32 |
| HPOO dye (2x) | 88 | 81 | 50 | 62 |
| HPOO dye (x) | 88 | 84 | 64 | 63 |
| HPOO (x/2) | 87 | 84 | 72 | 66 |
| HPOO (x/4) | 89 | 87 | 79 | 71 |

In Table IV the dye concentrations are approximately 35 ppm (2x), 15 ppm (x), 7.5 ppm (x/2), and 3.8 ppm (x/4).

Increases in contrast sensitivity are observed with appropriate concentration of perylene. See Example 2, Table VI. It should be pointed out that the family of perylene based dyes or pigments are used, by way of example only, for enabling embodiments of the invention. When such a dye is used, depending upon the embodiment or application, the dye may be formulated such that it is bonded molecularly or chemically to the substrate or a coating that is applied to the substrate such that the dye does not leach out. By way of example only, applications of this would be for use with contact lenses, IOLs, corneal in-lays, corneal on-lays, etc.

Selective filters can be combined to hinder other target wavelengths as science discovers other visible light wavelength hazards.

In one embodiment of the invention, a contact lens is comprised of a perylene dye formulated such that it will not leach out of the contact lens material. The dye is further formulated such that it provides a tint having a yellow cast. This yellow cast allows for the contact lens to have what is known as a handling tint for the wearer. The perylene dye or pigment further provides the selective filtering as shown by FIG. 48. This filtering provides retinal protection and enhanced contrast sensitivity without compromising in any meaningful way one's photopic vision, scotopic vision, color vision, or circadian rhythms.

In the case of the inventive embodiment of a contact lens the dye or pigment can be imparted into the contact lens by way of example only, by imbibing, so that it is located within a central 10 mm diameter or less circle of the contact lens, preferably within 6-8 mm diameter of the center of the contact lens coinciding with the pupil of the wearer. In this embodiment the dye or pigment concentration which provides selective light wavelength filtering is increased to a level that provides the wearer with an increase in contrast sensitivity (as oppose to without wearing the contact lens) and without compromising in any meaningful way (one or more, or all of) the wearer's photopic vision, scotopic vision, color vision, or circadian rhythms.

Preferably, an increase in contrast sensitivity is demonstrated by an increase in the user's Functional Acuity Contrast Test (FACT) score of at least about 0.1, 0.25, 0.3, 0.5, 0.7, 1, 1.25, 1.4, or 1.5. With respect to the wearer's photopic vision, scotopic vision, color vision, and/or circadian rhythms, the ophthalmic system preferably maintains one or all of these characteristics to within 15%, 10%, 5%, or 1% of the characteristic levels without the ophthalmic system.

In another inventive embodiment that utilizes a contact lens the dye or pigment is provided that causes a yellowish tint that it is located over the central 5-7 mm diameter of the contact lens and wherein a second color tint is added peripherally to that of the central tint. In this embodiment the dye concentration which provides selective light wavelength filtering is increased to a level that provides the wearer very good contrast sensitivity and once again without compromising in any meaningful way (one or more, or all of) the wearer's photopic vision, scotopic vision, color vision, or circadian rhythms.

In still another inventive embodiment that utilizes a contact lens the dye or pigment is provided such that it is located over the full diameter of the contact lens from approximately one edge to the other edge. In this embodiment the dye concentration which provides selective light wavelength filtering is increased to a level that provides the wearer very good contrast sensitivity and once again without compromising in any meaningful way (one or more, or all of) the wearer's photopic vision, scotopic vision, color vision, or circadian rhythms.

When various inventive embodiments are used in or on human or animal tissue the dye is formulated in such a way to chemically bond to the inlay substrate material thus ensuring it will not leach out in the surrounding corneal tissue. Methods for providing a chemical hook that allow for this bonding are well known within the chemical and polymer industries.

In still another inventive embodiment an intraocular lens includes a selective light wavelength filter that has a yellowish tint, and that further provides the wearer improved contrast sensitivity without compromising in any meaningful way (one or more, or all of) the wearer's photopic vision, scotopic vision, color vision, or circadian rhythms. When the selective filter is utilized on or within an intraocular lens it is possible to increase the level of the dye or pigment beyond that of a spectacle lens as the cosmetics of the intraocular lens are invisible to someone looking at the wearer. This allows for the ability to increase the concentration of the dye or pigment and provides even higher levels of improved contrast sensitivity without compromising in any meaningful way (one or more, or all of) the wearer's photopic vision, scotopic vision, color vision, or circadian rhythms.

In still another embodiment of the invention, a spectacle lens includes a selective light wave length filter comprising a dye having perylene wherein the dye's formulation provides a spectacle lens that has a mostly colorless appearance. And furthermore that provides the wearer with improved contrast sensitivity without compromising in any meaningful way (one or more, or all of) the wearer's photopic vision, scotopic vision, color vision, or circadian rhythms. In this particular embodiment of the invention, the dye or pigment is imparted within a film that is located within or on the surface of the spectacle lens.

EXAMPLES

Example 1

Figure 45:
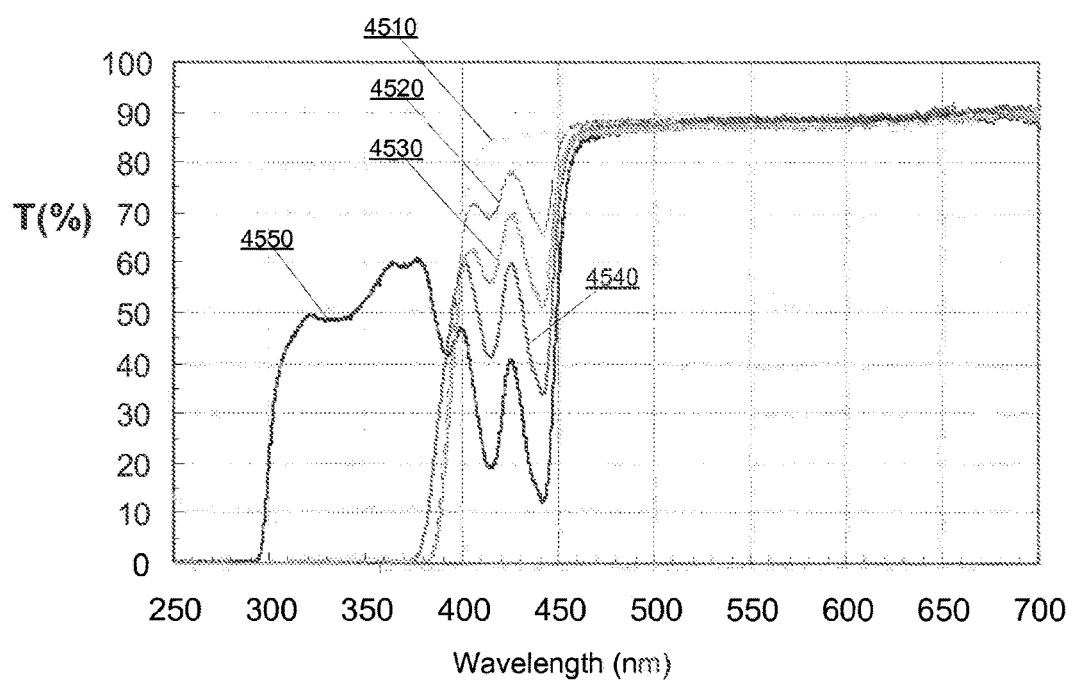
FIG. 45 shows transmission spectra for various lenses.

A polycarbonate lens having an integral film with varying concentrations of blue-blocking dye was fabricated and the transmission spectrum of each lens was measured as shown in FIG. 45. Perylene concentrations of 35, 15, 7.6, and 3.8 ppm (weight basis) at a lens thickness of 2.2 mm were used. Various metrics calculated for each lens are shown in Table V, with references corresponding to the reference numerals in FIG. 45. Since the selective absorbance of light depends primarily on the product of the dye concentration and coating thickness according to Beer's law, it is believed that comparable results are achievable using a hard coat and/or primer coat in conjunction with or instead of a film.

TABLE V

| Lens | Ref. | Photopic Ratio ($V_\lambda$) | Scotopic Ratio ($V'_\lambda$) | Circadian Ratio ($M'_\lambda$) | Phototoxicity Ratio ($B_\lambda$) |
|---|---|---|---|---|---|
| Unfiltered light (no lens) | | 100.0% | 100.0% | 100.0% | 100.0% |
| Polycarbonate Lens (no dye) | 4510 | 87.5% | 87.1% | 74.2% | 85.5% |
| 3.8 ppm (2.2 mm) | 4520 | 88.6% | 86.9% | 71.0% | 78.8% |
| 7.6 ppm (2.2 mm) | 4530 | 87.0% | 84.1% | 65.9% | 71.1% |
| 15 ppm (2.2 mm) | 4540 | 88.3% | 83.8% | 63.3% | 63.5% |
| 35 ppm (2.2 mm) | 4550 | 87.7% | 80.9% | 61.5% | 50.2% |

With the exception of the 35 ppm dyed lens, all the lenses described in Table IV and FIG. 45 include a UV dye typically used in ophthalmic lens systems to inhibit UV wavelengths below 380 nm. The photopic ratio describes normal vision, and is calculated as the integral of the filter transmission spectrum and $V\lambda$ (photopic visual sensitivity) divided by the integral of unfiltered light and this same sensitivity curve. The scotopic ratio describes vision in dim lighting conditions, and is calculated as the integral of the filter transmission spectrum and $V'\lambda$, (scotopic visual sensitivity) divided by the integral of unfiltered light and this same sensitivity curve. The circadian ratio describes the effect of light on circadian rhythms, and is calculated as the integral of the filter transmission spectrum and $M'\lambda$, (melatonin suppression sensitivity) divided by the integral of unfiltered light and this same sensitivity curve. The phototoxicity ratio describes damage to the eye caused by exposure to high-energy light, and is calculated as the integral of the filter transmission and the $B\lambda$ (phakic UV-blue phototoxicity) divided by the integral of unfiltered light and this same sensitivity curve. Response functions used to calculate these values correspond to those disclosed in Mainster and Sparrow, "How Much Blue Light Should an IOL Transmit?" Br. J. Ophthalmol., 2003, v. 87, pp. 1523-29, Mainster, "Intraocular Lenses Should Block UV Radiation and Violet but not Blue Light," Arch. Ophthal., v. 123, p. 550 (2005), and Mainster, "Violet and Blue Light Blocking Intraocular Lenses: Photoprotection vs. Photoreception", Br. J. Ophthalmol, 2006, v. 90, pp. 784-92. For some applications, a different phototoxicity curve is appropriate but the methodology for calculation is the same. For example, for intraocular lens (IOL) applications, the aphakic phototoxicity curve should be used. Moreover, new phototoxicity curves may be applicable as the understanding of the phototoxic light mechanisms improves.

As shown by the exemplary data described above, a system according to embodiments of the present invention may selectively inhibit blue light, specifically light in the 400 nm-460 nm region, while still providing a photopic luminous transmission of at least about 85% and a phototoxicity ration of less than about 80%, more preferably less than about 70%, more preferably less than about 60%, and more preferably less than about 50%. As previously described, a photopic luminous transmission of up to 95% or more also may be achievable using the techniques described herein.

The principles described herein may be applied to varied illuminants, filters, and skin tones, with the objective of filtering some portion of phototoxic blue light while reducing pupil dilation, scotopic sensitivity, color distortion through the ophthalmic device, and cosmetic color of an external ophthalmic device from the perspective of an observer that views the person wearing the device on their face.

Several embodiments of the invention are specifically illustrated and/or described herein. However, it will be appreciated that modifications and variations of embodiments of the invention are covered by the above teachings and within the purview of the appended claims without departing from the spirit and intended scope of embodiments of the invention. For examples, although the methods and systems described herein have been described using examples of specific dyes, dielectric optical filters, skin tones, and illuminants, it will be understood that alternative dyes, filters, skin colors, and illuminants may be used.

Example 2

Nine patients were tested for contrast sensitivity using dye concentrations of 1× and 2× against a clear filter as a control 7 of the 9 patients showed overall improved contrast sensitivity according to the Functional Acuity Contrast Test (FACT). See Table VI:

TABLE VI

Contrast sensitivity test for dye samples with loadings of X and 2X. Test was done in February, 2007 at Vision Associates in Havre de Grace, Maryland by Dr. Andy Ishak.
The test consisted of 10 patients, each tested with two filters, using the FACT contrast sensitivity testing process

|   |   |   | 3 | 4 Dotted A | 5 | 6 | 7 Dotted B | 8 | 9 | 10 Dotted C | 11 | 12 | 13 Dotted D | 14 | 15 | 16 Dotted E | 17 | 18 | 19 Solid A | 20 |
|---|---|---|---|---|---|---|---|---|---|---|---|---|---|---|---|---|---|---|---|---|
| 3 | 1 | 2 | NO | Lt | Dk | NO | Lt | Dk | NO | Lt | Dk | NO | Lt | Dk | NO | Lt | Dk | NO | Lt | Dk |
| 4 | 1 | JP | 5 | 6 | 6 | 6 | 6 | 6 | 6 | 6 | 6 | 5 | 5 | 5 | 4 | 4 | 4 | 7 | 6 | 7 |
| 5 |   |   |   | 1* | 1* |   | 0 | 0 |   | 0 | 0 |   | 0 | 0 |   | 0 | 0 |   | -1** | 0 |
| 6 | 2 | BJ | 6 | 7 | 7 | 7 | 7 | 7 | 7 | 6 | 6 | 3 | 3 | 3 | 4 | 3 | 3 | 7 | 5 | 6 |
| 7 |   |   |   | 1* | 1* |   | 0 | 0 |   | -1** | -1** |   | 0 | 0 |   | -1** | -1** |   | -2** | -1** |
| 8 | 3 | JB | 8 | 8 | 8 | 6 | 7 | 7 | 5 | 5 | 7 | 5 | 4 | 5 | 1 | 3 | 5 | 9 | 9 | 9 |
| 9 |   |   |   | 0 | 0 |   | 1* | 1* |   | 0 | 2* |   | -1** | 0 |   | 2* | 4* |   | 0 | 0 |
| 10 | 4 | AW | 7 | 7 | 8 | 6 | 7 | 8 | 6 | 5 | 7 | 5 | 5 | 6 | 4 | 4 | 5 | 6 | 7 | 7 |
| 11 |   |   |   | 0 | 1* |   | 1* | 2* |   | -1** | 1* |   | 0 | 1* |   | 0 | 1* |   | 1* | 1* |
| 12 | 5 | LL | 7 | 6 | 6 | 6 | 6 | 5 | 2 | 5 | 3 | 1 | 4 | 4 | 1 | 3 | 2 | 6 | 6 | 6 |
| 13 |   |   |   | -1** | -1** |   | 0 | -** |   | 3* | 1* |   | 3* | 3* |   | 2* | 1* |   | 0 | 0 |
| 14 | 6 | TS | 7 | 9 | 9 | 8 | 9 | 9 | 8 | 9 |   | 6 | 7 | 7 | 4 | 7 | 5 | 5 | 8 | 8 |
| 15 |   |   |   | 2* | 2* |   | 1* | 1* |   | 1* | 0 |   | 1* | 1* |   | 3* | 1* |   | 3* | 3* |
| 16 | 7 | KS | 6 | 6 | 6 | 5 | 5 | 5 | 5 | 4 | 4 | 3 | 2 | 2 | 2 | 1 | 1 | 5 | 6 | 5 |
| 17 |   |   |   | 0 | 0 |   | 0 | 0 |   | -1** | -1** |   | -1** | -1** |   | -1** | -1** |   | 1* | 0 |
| 18 | 9 | DS | 5 | 6 | 6 | 5 | 7 | 7 | 5 | 6 | 6 | 3 | 5 | 5 | 1 | 4 | 4 | 5 | 6 | 7 |
| 19 |   |   |   | 1* | 1* |   | 2* | 2* |   | 1* | 1* |   | 2* | 2* |   | 3* | 3* |   | 1 | 2* |
| 20 | 10 | NK |   |   |   |   |   |   |   |   |   |   |   |   |   |   |   | 9 | 9 | 9 |
| 21 |   |   |   |   |   |   |   |   |   |   |   |   |   |   |   |   |   |   | 0 | 0 |
| 22 Tot |   |   | 51 | 55 | 56 | 49 | 54 | 54 | 44 | 46 | 47 | 31 | 35 | 37 | 21 | 29 | 29 | 59 | 62 | 64 |
| 23 Delta |   |   |   | 4 | 5 |   | 5 | 5 |   | 2 | 3 |   | 4 | 6 |   | 8 | 8 |   | 3 | 5 |
| 24 Avg |   |   | 6.4 | 6.9 | 7.0 | 6.1 | 6.8 | 6.8 | 5.5 | 5.8 | 5.9 | 3.9 | 4.4 | 4.6 | 2.6 | 3.6 | 3.6 | 6.6 | 6.9 | 7.1 |
| 25 Delta |   |   |   | 0.5 | 0.6 |   | 0.6 | 0.6 |   | 0.3 | 0.4 |   | 0.5 | 0.8 |   | 1.0 | 1.0 |   | 0.3 | 0.6 |
| 26 |   |   |   |   |   |   |   |   |   |   |   |   |   |   |   |   |   |   |   |   |
| 27 Better (gr) |   |   |   | 4* | 5* |   | 4* | 4* |   | 3 | 4* |   | 3* | 4* |   | 4* | 5* |   | 4* | 3* |
| 28 Worst (rd) |   |   |   | 2 | 1 |   | 1 | 2 |   | 3 | 2 |   | 2 | 1 |   | 3 | 3 |   | 3 | 2 |

|   |   |   | 21 | 22 Solid B | 23 | 24 | 25 Solid C | 26 | 27 | 28 Solid D | 29 | 30 | 31 Solid E | 32 | 33 | 34 Number Better (gr) | 35 Worse (rd) |
|---|---|---|---|---|---|---|---|---|---|---|---|---|---|---|---|---|---|
| 3 |   |   | NO | Lt | Dk | NO | Lt | Dk | NO | Lt | Dk | NO | Lt | Dk | Tot Diff |   |   |
| 4 | 1 | JP | 6 | 6 | 7 | 6 | 7 | 6 | 5 | 5 | 5 | 5 | 2 | 4 |   |   |   |
| 5 |   |   |   | 1* |   |   | 1* | 0 |   | 0 | 0 |   | -3** | -1** | -1 | 4* | 3 |
| 6 | 2 | BJ | 7 | 7 | 7 | 8 | 7 | 7 | 6 | 6 | 6 | 4 | 5 | 5 |   |   |   |
| 7 |   |   |   |   | 0 |   | -1** | -1** |   | 0 | 0 |   | 1* | 1* | -5 | 4 | 6** |
| 8 | 3 | JB | 7 | 9 | 9 | 8 | 8 | 8 | 5 | 6 | 9 | 4 | 4 | 5 |   |   |   |
| 9 |   |   |   |   | 2* |   | 0 | 0 |   | 1 | 4 |   | 0 | 1* | 19 | 10* | 1 |
| 10 | 4 | AW | 6 | 6 | 7 | 5 | 6 | 7 | 3 | 4 | 6 | 3 | 5 | 6 |   |   |   |
| 11 |   |   |   |   | 1* |   | 1* | 2* |   | 1 | 3 |   | 2* | 3* | 21 | 15* | 1 |
| 12 | 5 | LL | 6 | 5 | 6 | 2 | 6 | 4 | 3 | 2 | 3 | 2 | 4 | 2 |   |   |   |
| 13 |   |   |   |   | 0 |   | 4* | 2* |   | -1** | 0 |   | 2* | 0 | 16 | 9* | 6 |
| 14 | 6 | TS | 6 | 8 | 8 | 7 | 8 | 8 | 4 | 5 | 5 | 4 | 4 | 4 |   |   |   |
| 15 |   |   |   |   | 2* |   | 1* | 1* |   | 1 | 1 |   | 0 | 0 | 27 | 17* | 0 |
| 16 | 7 | KS | 5 | 5 | 4 | 2 | 4 | 4 | 2 | 2 | 3 | 1 | 1 | 1 |   |   |   |
| 17 |   |   |   |   | -1** |   | 2* | 2* |   | 0 | 1 |   | 0 | 0 | -1 | 4 | 7** |
| 18 | 9 | DS | 6 | 6 | 6 | 5 | 5 | 5 | 3 | 4 | 4 | 2 | 3 | 3 |   |   |   |

TABLE VI-continued

Contrast sensitivity test for dye samples with loadings of X and 2X. Test was done in February, 2007 at Vision Associates in Havre de Grace, Maryland by Dr. Andy Ishak.
The test consisted of 10 patients, each tested with two filters, using the FACT contrast sensitivity testing process

| 19 |    |    |     |     | 0   |     | 0   | 0   |     | 1   | 1   |     | 1*  | 1*  | 25  | 16* | 0 |
|----|----|----|-----|-----|-----|-----|-----|-----|-----|-----|-----|-----|-----|-----|-----|-----|---|
| 20 | 10 | NK | 9   | 9   | 8   | 7   | 7   | 8   | 4   | 5   | 7   | 4   | 6   | 8   |     |     |   |
| 21 |    |    |     | 0   | -1**|     | 0   | 1*  |     | 1   | 3   |     | 2*  | 4*  | 10  | 5*  | 1 |
| 22 | Tot |   | 58  | 61  | 62  | 50  | 58  | 57  | 35  | 39  | 48  | 29  | 34  | 38  |     |     |   |
| 23 | Delta |  |    | 3   | 4   |     | 8   | 7   |     | 4   | 13  |     | 5   | 9   | 111 |     |   |
| 24 | Avg |   | 6.4 | 6.8 | 6.9 | 5.6 | 6.4 | .3  | 3.9 | 4.3 | 5.3 | 3.2 | 3.8 | 4.2 | 5.6 |     |   |
| 25 | Delta |  |    | 0.3 | 0.4 |     | 0.9 | 0.8 |     | 0.4 | 1.4 |     | 0.6 | 1.0 |     |     |   |
| 26 |    |    |     |     |     |     |     |     |     |     |     |     |     |     |     |     |   |
| 27 | Better (gr) | | | 2 | 4* |   | 5*  | 5*  |     | 5*  | 5*  |     | 5*  | 5*  |     |     |   |
| 28 | Worst (rd) |  |   | 2 | 3  |   | 2   | 2   |     | 2   | 1   |     | 2   | 2   |     |     |   |

Comments:
1. Patient number 8 data was dropped. This patient was a 60 yr old, diabetic, with cataracts
2. Patient 10 was tested in one eye only
3. The terms dotted and solid refer to the two eyes of the patients, how they were shown on test result forms
4. The headings "NO", refer to lenses with clear filter, ie control. The terms Lt and Dk refer to the dye loading in the tested filters.
5. For each patient, the top line is their actual score. Second line is the difference with filters versus non filtered "control"
6. Boxes marked with (*) showed improvement, boxes with (**) showed negative results.
7. Total scores (line 22) add up how all patients scored on a specific test column
8. Total Difference (column 33) shows how each patient scored overall on all 5 test columns (A-E) for both eyes
9. Note, each patient (except #10) had 20 opportunities to score a difference -- 2 eyes × 5 columns on the test × 2 filters
10. Better and Worse numbers (rows 27-28, columns 34-35) simply add up the opportunities that scored better with the filters or worse, versus the clear control
Results
1. 7 of the 9 patients showed overall improved contrast sensitivity results (columns 33-35)
2. Patients overall showed improvement in both eyes on 18 of the 20 opportunities (2 eyes × two filters × five FACT columns) (rows 27-28)
3. On average, patients improved by 0.3-1.4 for all 20 opportunities (row 25)

In an embodiment of the invention, an ophthalmic lens is comprised of a dye that causes the lens to selectively inhibit transmission of visible light between 450±50 nm and has a yellowness index of not more than 35.0. More preferably, the dye selectively inhibits transmission of visible light between 430±30 nm and has a yellowness index of not more than 35.0. The dye selected to inhibit transmission would also block light wavelengths across the entire range, as well providing a more focused blocking in just the preferred subset of the range. More preferably, the dye would cause the lens to block at least 5%, preferably 10%, more preferably 20%, more preferably 30%, or most preferably 40% of light having a wavelength of 450±50 nm. Further, the dye would cause the lens to block at least 5%, preferably 10%, more preferably 20%, more preferably 30%, more preferably 40%, or most preferably 50% of light having a wavelength of 430±30 nm.

As used herein, "dye" refers to a chemical or chemicals that can be added to the lens materials or coatings which absorb light at a specific wavelength or wavelengths.

It is preferred to selectively inhibit transmission of visible light between 450±50 nm because blue light wavelengths fall in the approximate range of 400 nm to 500 nm. Blue light in this range is believed to cause damage to eye cells that can result in a number of adverse conditions such as macular degeneration and other retinal disease such a uveal melanoma. Thus, it is desirable to block the specific light wavelengths that have been shown to cause adverse conditions. Further, for many applications it may be desirable to selectively inhibit less than 50% of blue light, and/or the specific wavelengths inhibited may vary. It is believed that in many applications cell death may be reduced or prevented by blocking less than 50% of blue light. For example, it may be preferred to selectively inhibit about 40%, more preferably about 30%, more preferably about 20%, more preferably about 10%, and more preferably about 5% of light. Selectively inhibiting a smaller amount of light may allow for prevention of damage due to high-energy light, while being minimal enough that the inhibition does not adversely affect scotopic vision and/or circadian cycles in a user of the system. Additionally, in some cases it may be preferred to block a lower percentage such as 5% in order to maintain a low yellowness index so as not to distort the viewer's perception of color. In other cases it may be preferable to provide more blocking, such as at 50%, where due to the nature and material of the lens, the effects of a higher yellowness index may be better tolerated or accepted by the user. In other cases, due to the type of ophthalmic lens and dye utilized, a blocking of at least 10% to at least 40% is preferred in order to strike a balance between protection from blue light waves and other concerns such as aesthetic appeal and adverse biological effects.

In some cases it may be particularly desirable to filter a relatively small portion of the blue spectrum, such as light between 430±30 nm. It has been found that blocking too much of the blue spectrum can interfere with scotopic vision and circadian rhythms. Conventional blue blocking ophthalmic lenses typically block a much larger amount of wide range of the blue spectrum, which can adversely affect the wearer's "biological clock" and have other adverse effects. Thus, it may be desirable to block a relatively narrow range of the blue spectrum as described herein. Exemplary system that may filter a relatively small range include systems block or absorb at least 5%, at least 10%, at least 20%, at least 30%, at least 40%, or at least 50%. Further as discussed above, in some cases it may be preferred to block a lower percentage such as 5% in order to maintain a low yellowness index so as not to distort the viewer's perception of color. In other cases it may be preferable to provide more blocking, such as at 50%, where due to the nature and material of the lens, the effects of a higher yellowness index may be better tolerated or accepted by the user. In other cases, due to the type of ophthalmic lens and dye utilized, a blocking of at least 10% to at least 40% is preferred in order to strike a balance between protection from blue light wavelengths and other concerns such as aesthetic appeal and adverse biological effects.

The ophthalmic lens may be selected from prescription or non-prescription ophthalmic lenses known to those of skill in the art. By way of example, see lenses listed and described above.

Some embodiments of the invention use a dye such as bilirubin; chlorophyll a, diethyl ether; chlorophyll a, methanol; chlorophyll b; diprotonated-tetraphenylporphyrin; hematin; magnesium octaethylporphyrin; magnesium octaethylporphyrin (MgOEP); magnesium phthalocyanine (MgPc), PrOH; magnesium phthalocyanine (MgPc), pyridine; magnesium tetramesitylporphyrin (MgTMP); magnesium tetraphenylporphyrin (MgTPP); octaethylporphyrin; phthalocyanine (Pc); porphin; tetra-t-butylazaporphine; tetra-t-butylnaphthalocyanine; tetrakis(2,6-dichlorphenyl) porphyrin; tetrakis(o-aminophenyl)porphyrin; tetramesitylporphyrin (TMP); tetraphenylporphyrin (TPP); vitamin B12; zinc octaethylporphyrin (ZnOEP); zinc phthalocyanine (ZnPc), pyridine; zinc tetramesitylporphyrin (ZnTMP); zinc tetramesitylporphyrin radical cation; zinc tetraphenylporphyrin (ZnTPP); perylene and derivatives thereof, or any dye, synthetic or non-synthetic pigments, antioxidants, photochromics, visibility and/or cosmetic tint in a contact lens or any material means that elicits a yellowness index of 35.0 or less.

By way of example, in embodiments of the present invention that utilize a dye, the dye may be: within the polymer, in a film or films, in a coating or coatings, in one or more anti-reflective coatings, in one or more hard coats, in one or more primer coats, in any layer of the lens, in various concentration (ppm) based upon the yellowness index specifications, a visibility tint or tints in a contact lens, in a sunglass, incorporated in a photochromic lens, in one or more rings, zones, layers and/or peaks, a cosmetic tint or tints, varying in slope or slopes, color balancing, or any combination of the above. It is understood that the previous list is non-exclusive and is merely exemplary.

In a further embodiment, the dye would block 5%-40% of light having a wavelength of 450±50 nm, while have a luminous transmission of at least 80%. More preferably, the dye would block 5%-50% of light having a wavelength of 430±30 nm, while have a luminous transmission of at least 80%.

In another inventive embodiment, the dye used would cause the lens to block at least 5%•of light having a wavelength of X±15 nm, where X is a wavelength in the range of 415-485 nm. More preferably, the dye would cause the lens to block at least 10%, or more preferably 20%, or more preferably 30%, or most preferably 40% of light having a wavelength of X±15 nm.

It is a further embodiment to utilize a contact lens wherein the yellowness index is not more than 35.0, or more preferably not more than 27.5, or most preferably not more than 20.0.

For embodiments that utilize contact lenses, it may be preferred to maintain a low yellowness index of not more than 35.0 in order to avoid affecting perceived color and in order to avoid a cosmetically unappealing appearance of yellowness in the lens itself, while still maintaining protection from the blue spectrum. As contact lenses are a type of ophthalmic lens that are handled by the wearer, are small relative to spectacle lenses, and may be difficult to find if dropped, a slightly higher yellowness index may be tolerated, and perhaps even be desirable to provide a handling tint, in a contact lens as opposed to other ophthalmic lenses. However, it is still desirable to maintain a yellowness sufficiently low as to avoid undesirable cosmetic effects.

Thus, a yellowness index value of no more than 35.0 is desired, as anything above this value may result in a lens that is too yellow and subsequently will not cosmetically appealing as its color may be observable even while it is in place in the user's eye. In some cases it may be preferred to maintain a yellowness index of not more than 27.5 in order to balance protection, color perception and cosmetic appeal, and in other instances a yellowness index of not more than 20.0 may be preferred.

It is a further embodiment to utilize a spectacle lens wherein the yellowness index is not more than 15.0, more preferably not more than 12.5, or most preferably not more than 10.0.

For embodiments that utilize spectacle lenses, it may be preferred to maintain a low yellowness index of not more than 15.0 in order to avoid affecting perceived color and in order to avoid a cosmetically unappealing appearance of yellowness in the spectacle lens itself, while still maintaining protection from the blue spectrum. A yellowness index value of no more than 15.0 is preferred as yellowness index values that are higher may result in a yellow tint in the spectacle lens that is cosmetically unappealing. In some cases it may be preferred to maintain a yellowness index of not more than 12.5 in order to balance protection, color perception and cosmetic appeal, and in other instances a yellowness index of not more than 10.0 may be preferred.

It is a further embodiment to utilize an intraocular lens wherein the yellowness index is not more than 23.0 or more preferably not more than 15.0.

For embodiments that utilize intraocular lenses, it may be preferred to maintain a low yellowness index of not more than 23.0 in order to avoid affecting perceived color and in order to avoid a cosmetically unappealing appearance of yellowness in the spectacle lens itself, while still maintaining protection from the blue spectrum. This value may be higher than that for other embodiments, such as spectacle lenses, as in the case of intraocular lenses the lens is implanted into the eye and thus, the concern for cosmetic appeal is somewhat lessened. In some cases it may be preferred to maintain a yellowness index of not more than 15.0 in order to balance protection, color perception and cosmetic appeal.

Furthermore, embodiments of the invention may include one or more front and/or back AR coats, film(s), primer(s), hardcoat(s), Hydrophobic coats(s), central/peripheral zone differential(s), electroactive(s), or any additional coating or layer or combination of coatings or layers.

In order to further protect the human eye from exposure to both harmful high energy visible light wavelengths and UV light and optionally IR light non-ophthalmic applications for embodiments of the invention are also included. A "non-ophthalmic system" includes any light transmissive structure, excluding ophthalmic lenses, through which light passes on its way to a viewer, as well as skin creams and lotions. By way of example only some non-ophthalmic systems may include: artificial lighting (non-sunlight), diffusers, any type of light bulb, windows, windshields, aircraft windows, instruments, operating devices and other equipment used by ophthalmologists and other eye care professionals to examine the eyes of patients, medical devices, telescopes, binoculars, hunting scopes for rifles, shotguns, and pistols, computer monitors, television sets, camera flashes, virtually any and all electronic devices that emit or transmit visible light, or any type of product or device whereby visible light is emitted or travels through said product or device whereby light from that product or device enters the human eye whether the light is filtered or not by the product or device can be enabled with embodiments of the invention. A non-ophthalmic system may further include dermatological products such as any skin or hair product, suntan and sunscreen products, lip stick, lip balm, anti-ageing products, oils, or acne products. Furthermore, military and space applications also apply as acute and/or chronic exposure to high energy visible light, UV, and also IR can potentially have a deleterious effect on soldiers and astronauts.

It is another embodiment of this invention to provide a non-ophthalmic system where the system contains at least one dye that causes the lens to selectively inhibit transmission of visible light between 450±50 nm and has a yellowness index of not more than 35.0. Preferably, the dye selectively inhibits transmission of visible light between 430±30 nm and has a yellowness index of not more than 35.0. More preferably, the dye selectively inhibits transmission of visible light between 435±20 nm and has a yellowness index of not more than 35.0. The dye selected to inhibit transmission would also block light wavelengths across the entire range, as well providing a more focused blocking in just the preferred subset of the range. More preferably, the dye would cause the lens to block at least 10%, or more preferably at least 20%, or more preferably at least 30%, or most preferably 40% of light having a wavelength of 450±50 nm while having a luminous transmission of at least 80%. Further, the dye may block at least 10%, or more preferably at least 20%, or more preferably at least 30%, or most preferably 40% light, or most preferably 50% of light having a wavelength of 430±30 nm while having a luminous transmission of at least 80%.

It is a further embodiment that the non-ophthalmic system may have a yellowness index of not more than 23.0 or more preferably not more than 15.0.

Embodiments described with respect to ophthalmic application may also be used in non-ophthalmic embodiments.

Figure 49A:
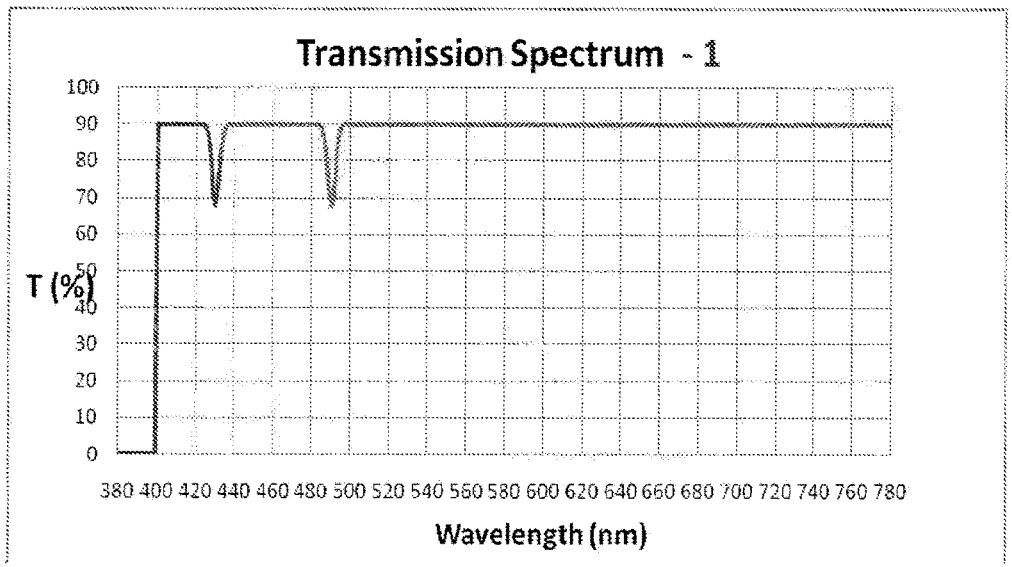
FIG. 49A shows a double selective filter with two peaks within the visible light spectrum along with some or all UV protection.
Figure 49B:
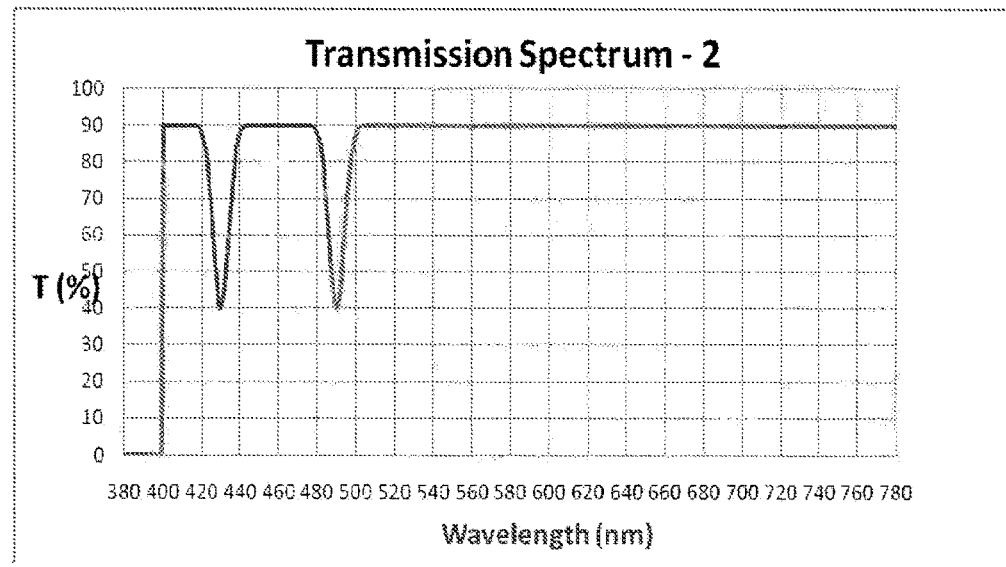
FIG. 49B shows a double selective filter with two peaks within the visible light spectrum along with some or all UV protection.
Figure 49C:
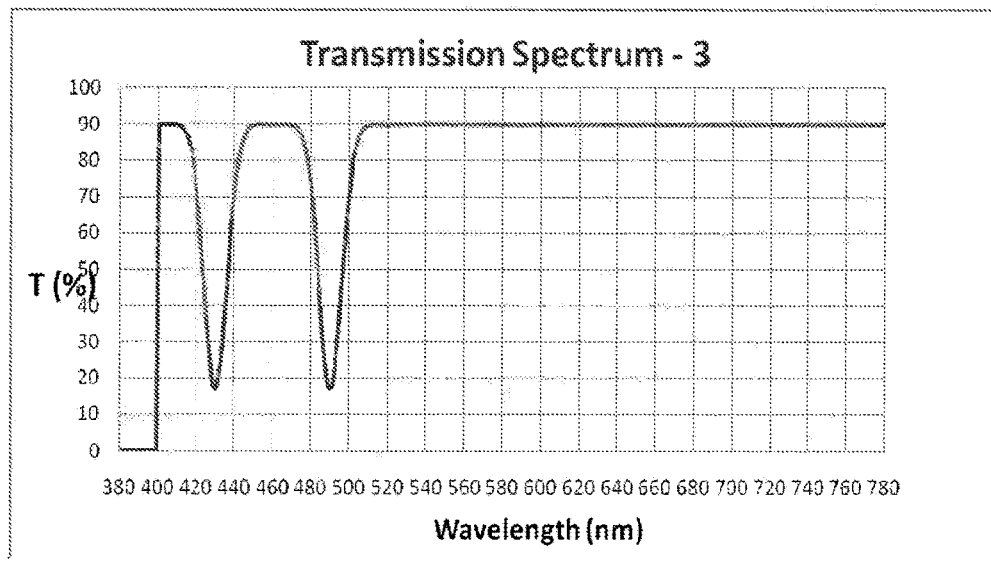
FIG. 49C shows a double selective filter with two peaks within the visible light spectrum along with some or all UV protection.
Figure 49D:
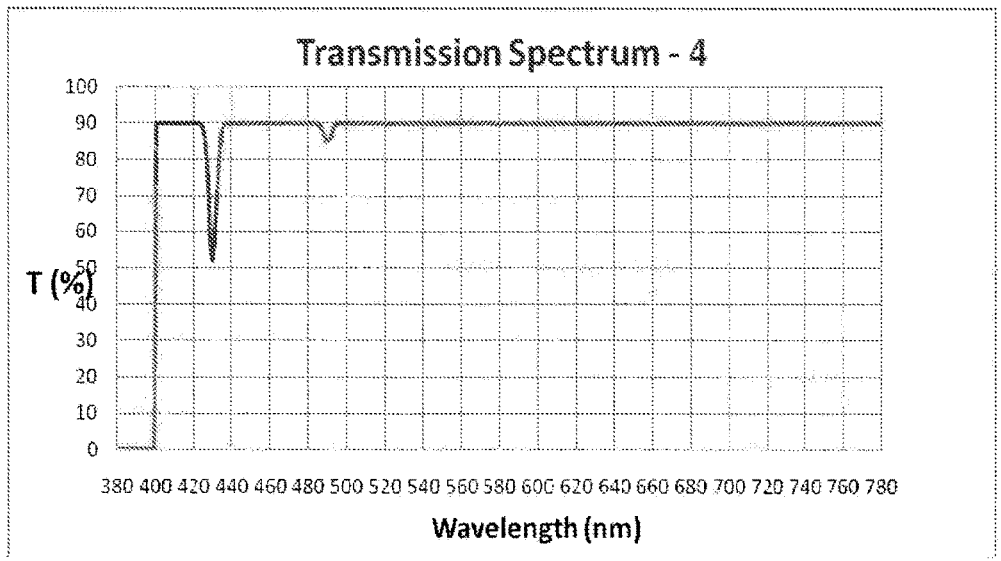
FIG. 49D shows a double selective filter with two peaks within the visible light spectrum along with some or all UV protection.
Figure 49E:
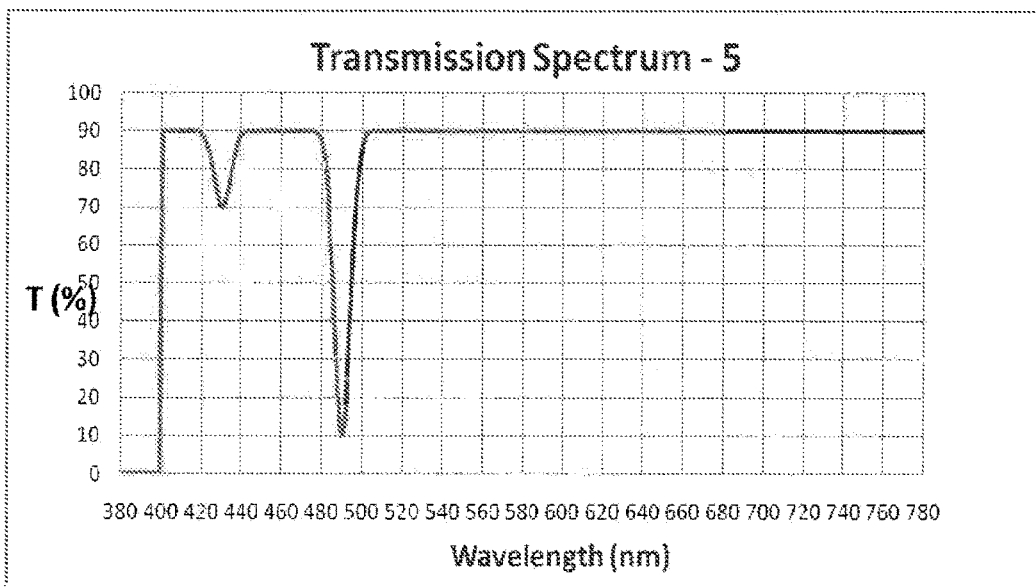
FIG. 49E shows a double selective filter with two peaks within the visible light spectrum along with some or all UV protection.
Figure 49F:
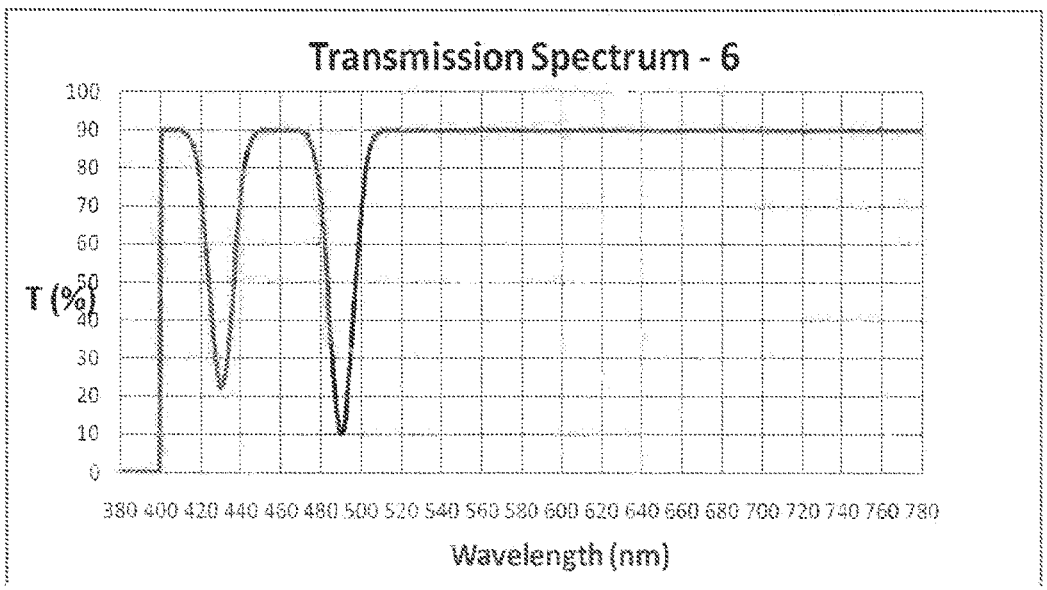
FIG. 49F shows a double selective filter with two peaks within the visible light spectrum along with some or all UV protection.
Figure 49G:
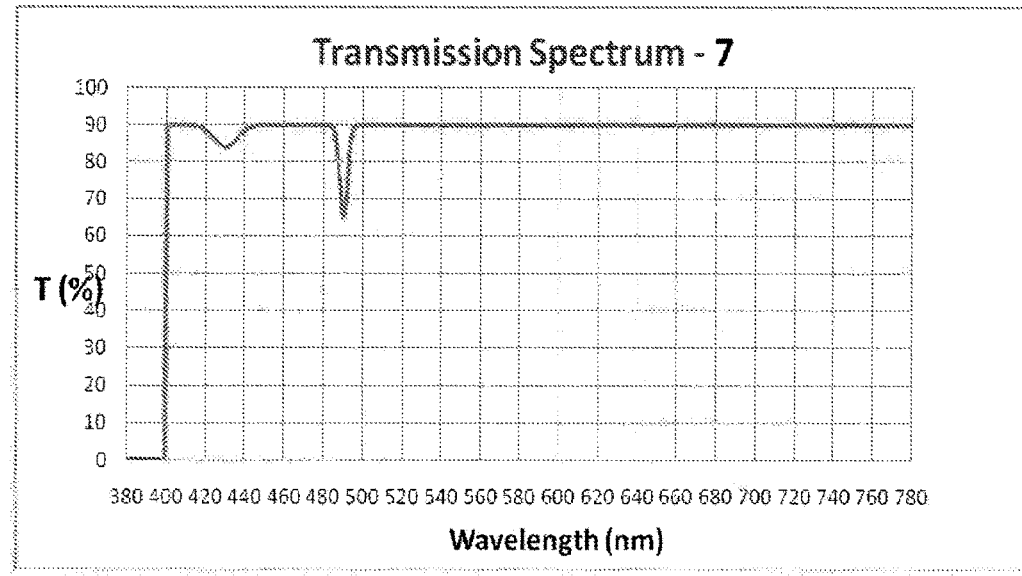
FIG. 49G shows a double selective filter with two peaks within the visible light spectrum along with some or all UV protection.
Figure 49H:
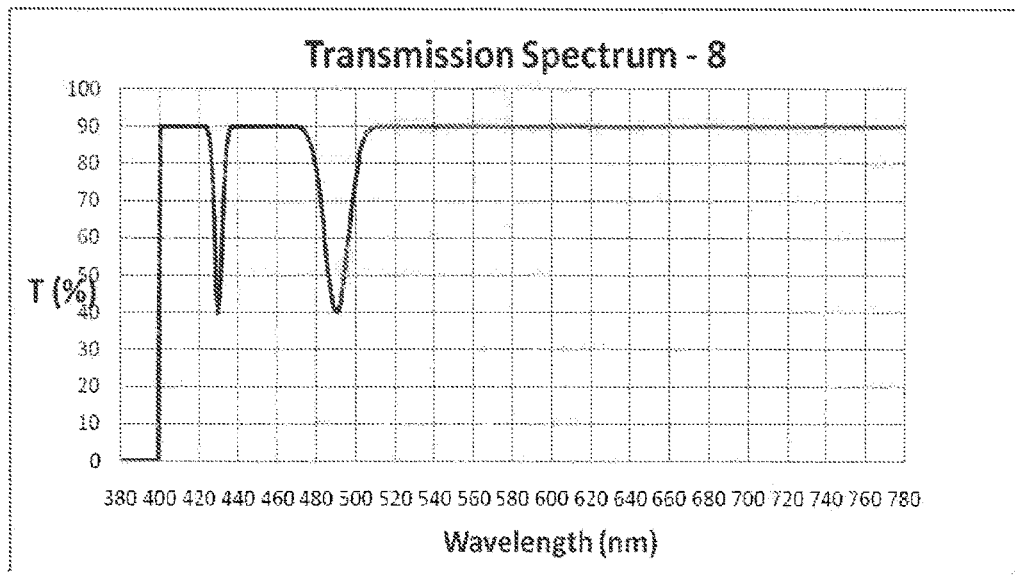
FIG. 49H shows a double selective filter with two peaks within the visible light spectrum along with some or all UV protection.
Figure 49I:
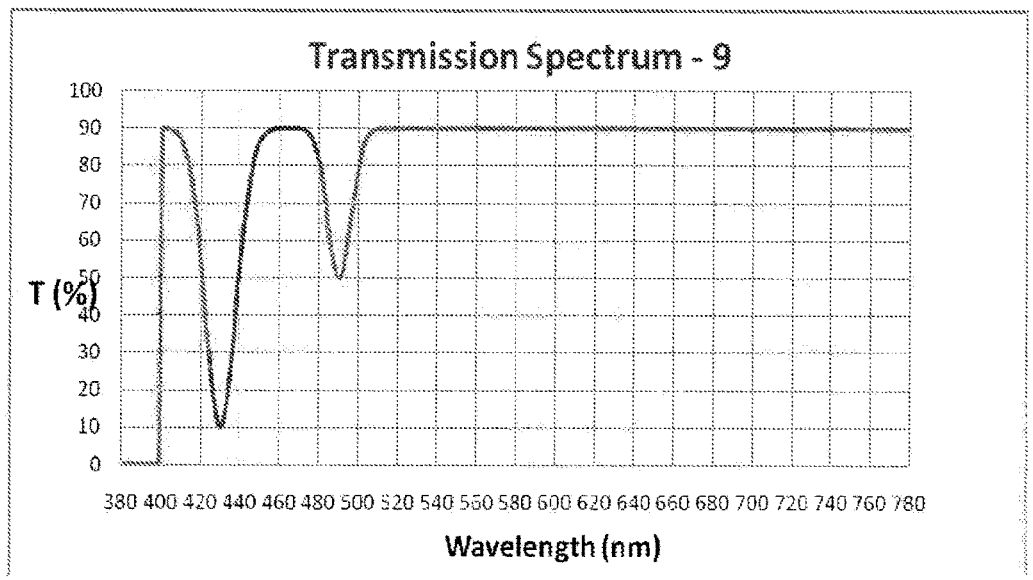
FIG. 49I shows a double selective filter with two peaks within the visible light spectrum along with some or all UV protection.
Figure 49J:
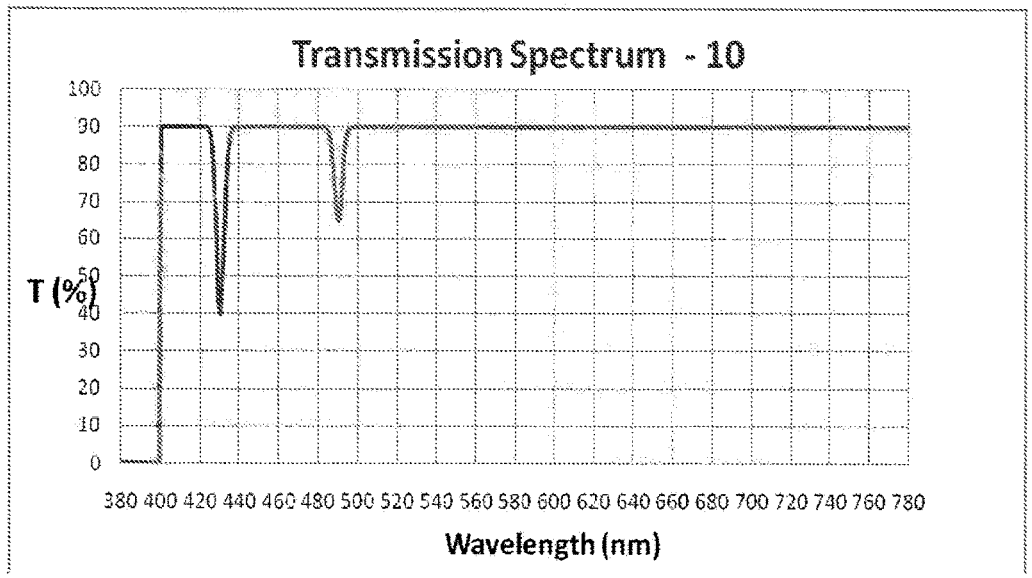
FIG. 49J shows a double selective filter with two peaks within the visible light spectrum along with some or all UV protection.
Figure 49K:
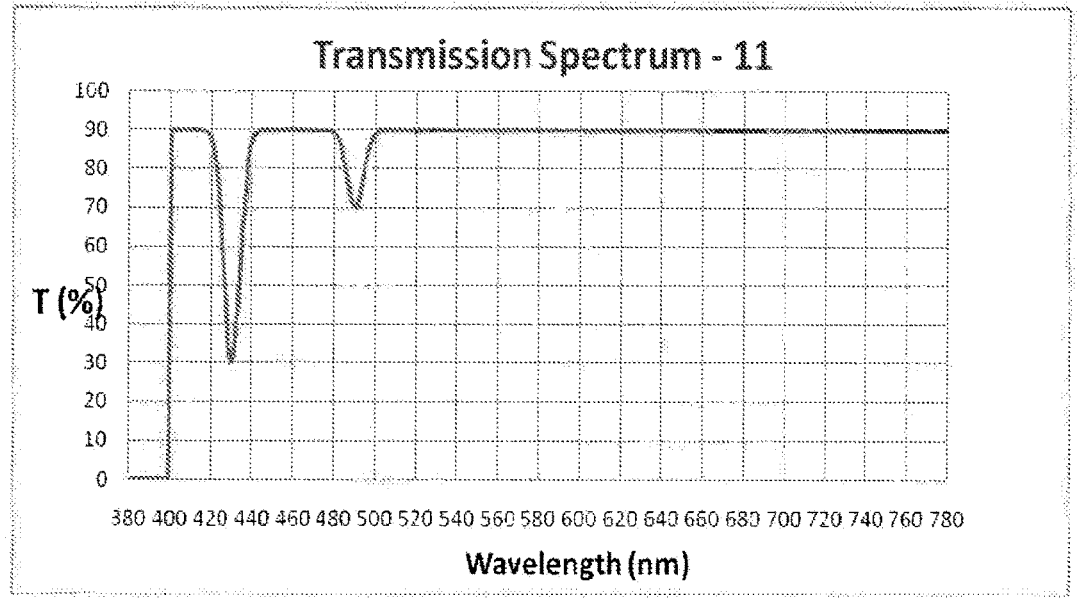
FIG. 49K shows a double selective filter with two peaks within the visible light spectrum along with some or all UV protection.
Figure 49L:
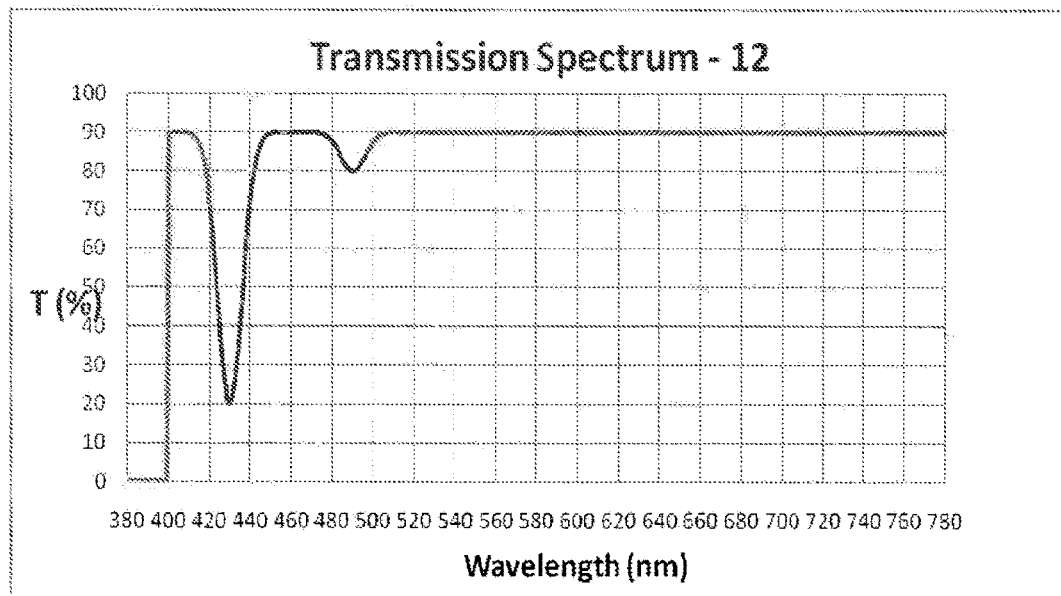
FIG. 49L shows a double selective filter with two peaks within the visible light spectrum along with some or all UV protection.
Figure 49M:
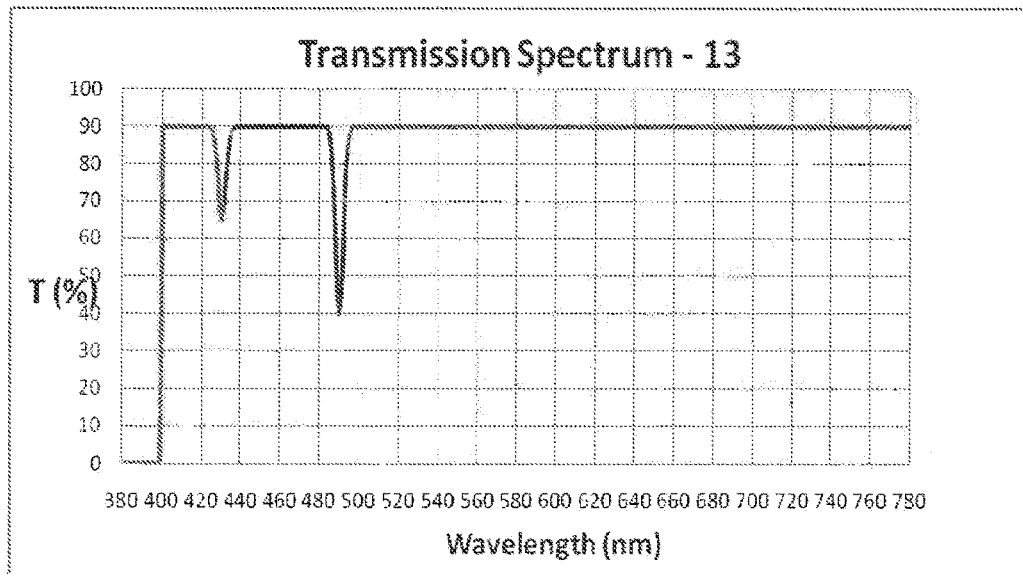
FIG. 49M shows a double selective filter with two peaks within the visible light spectrum along with some or all UV protection.
Figure 49N:
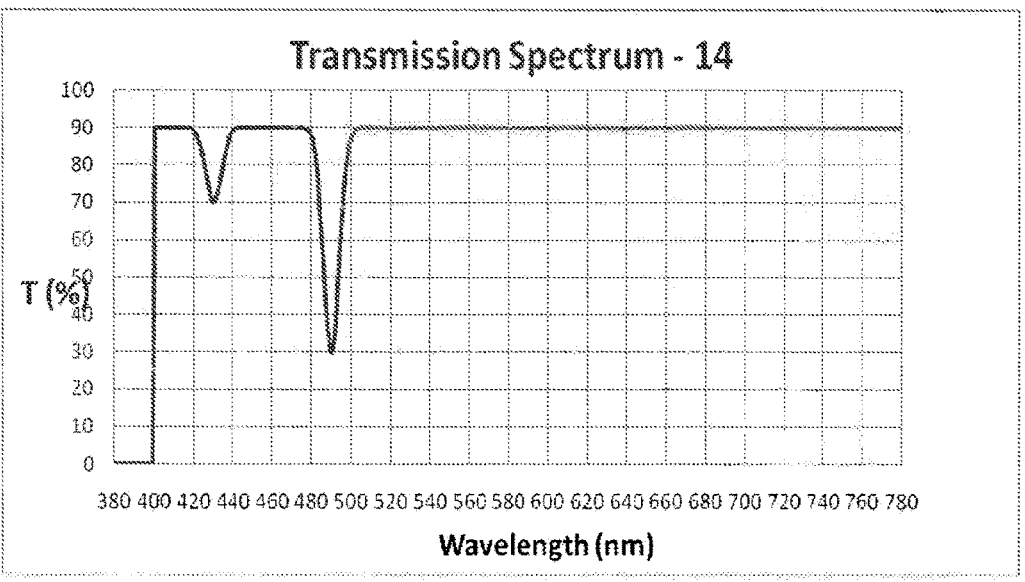
FIG. 49N shows a double selective filter with two peaks within the visible light spectrum along with some or all UV protection.
Figure 49O:
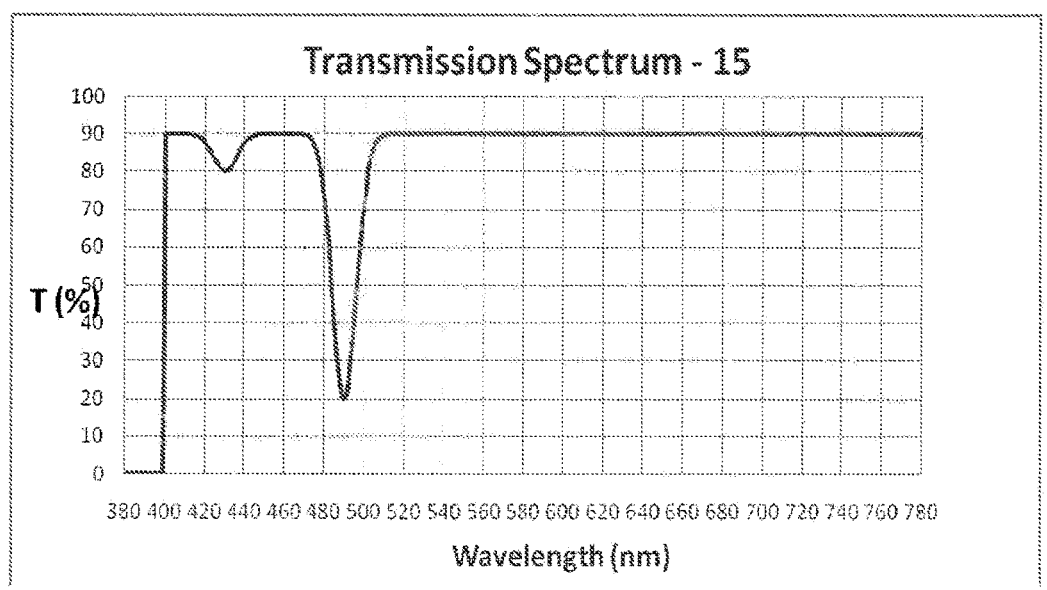
FIG. 49O shows a double selective filter with two peaks within the visible light spectrum along with some or all UV protection.

It is a further embodiment of the current invention to incorporate a unique double selective filter with two peaks within the visible light spectrum along with some or all UV protection. •The amount of selective filtering within the visible light spectrum can vary along with the slope of the spectral curve depending on the intended application of the system. This is illustrated in FIGS. 49A-O. Transmission values, as percentages, are shown for wavelengths 380-513 nm in Tables VII and VIII.

TABLE VII

Two Peak Transmission Spectra
Peaks are modeled as gaussian curves
Transmission averages are simple averages which do NOT take into account the sensitivity of the eye to weighting (luminous transmission)

| Scenario | Same peak depth and width | | | Vary peak depth | | | Vary peak width | | |
|---|---|---|---|---|---|---|---|---|---|
| | 1 | 2 | 3 | 4 | 5 | 6 | 7 | 8 | 9 |
| Average | 85.0 | 83.0 | 80.0 | 85.0 | 83.0 | 80.0 | 85.0 | 83.0 | 80.0 |
| Peak1 Scale | 22 | 50 | 73 | 38 | 20 | 68 | 6 | 50 | 80 |
| Peak2 Scale | 22 | 50 | 73 | 5 | 80 | 80 | 25 | 50 | 40 |
| St. Deviation1 | 2 | 4 | 6 | 2 | 4 | 6 | 6 | 2 | 8 |
| St. Devation2 | 2 | 4 | 6 | 2 | 4 | 6 | 2 | 6 | 6 |
| Wavelength | T (%) | T (%) | T (%) | T (%) | T (%) | T (%) | T (%) | T (%) | T (%) |
| 380 | 0 | 0 | 0 | 0 | 0 | 0 | 0 | 0 | 0 |
| 381 | 0 | 0 | 0 | 0 | 0 | 0 | 0 | 0 | 0 |
| 382 | 0 | 0 | 0 | 0 | 0 | 0 | 0 | 0 | 0 |
| 383 | 0 | 0 | 0 | 0 | 0 | 0 | 0 | 0 | 0 |
| 384 | 0 | 0 | 0 | 0 | 0 | 0 | 0 | 0 | 0 |
| 385 | 0 | 0 | 0 | 0 | 0 | 0 | 0 | 0 | 0 |
| 386 | 0 | 0 | 0 | 0 | 0 | 0 | 0 | 0 | 0 |
| 387 | 0 | 0 | 0 | 0 | 0 | 0 | 0 | 0 | 0 |
| 388 | 0 | 0 | 0 | 0 | 0 | 0 | 0 | 0 | 0 |
| 389 | 0 | 0 | 0 | 0 | 0 | 0 | 0 | 0 | 0 |
| 390 | 0 | 0 | 0 | 0 | 0 | 0 | 0 | 0 | 0 |
| 391 | 0 | 0 | 0 | 0 | 0 | 0 | 0 | 0 | 0 |
| 392 | 0 | 0 | 0 | 0 | 0 | 0 | 0 | 0 | 0 |
| 393 | 0 | 0 | 0 | 0 | 0 | 0 | 0 | 0 | 0 |
| 394 | 0 | 0 | 0 | 0 | 0 | 0 | 0 | 0 | 0 |
| 395 | 0 | 0 | 0 | 0 | 0 | 0 | 0 | 0 | 0 |
| 396 | 0 | 0 | 0 | 0 | 0 | 0 | 0 | 0 | 0 |
| 397 | 0 | 0 | 0 | 0 | 0 | 0 | 0 | 0 | 0 |
| 398 | 0 | 0 | 0 | 0 | 0 | 0 | 0 | 0 | 0 |
| 399 | 0 | 0 | 0 | 0 | 0 | 0 | 0 | 0 | 0 |
| 400 | 90.0 | 90.0 | 90.0 | 90.0 | 90.0 | 90.0 | 90.0 | 90.0 | 89.9 |
| 401 | 90.0 | 90.0 | 90.0 | 90.0 | 90.0 | 90.0 | 90.0 | 90.0 | 89.9 |
| 402 | 90.0 | 90.0 | 90.0 | 90.0 | 90.0 | 90.0 | 90.0 | 90.0 | 89.8 |
| 403 | 90.0 | 90.0 | 90.0 | 90.0 | 90.0 | 90.0 | 90.0 | 90.0 | 89.7 |
| 404 | 90.0 | 90.0 | 90.0 | 90.0 | 90.0 | 90.0 | 90.0 | 90.0 | 89.6 |
| 405 | 90.0 | 90.0 | 90.0 | 90.0 | 90.0 | 90.0 | 90.0 | 90.0 | 89.4 |
| 406 | 90.0 | 90.0 | 90.0 | 90.0 | 90.0 | 90.0 | 90.0 | 90.0 | 89.1 |
| 407 | 90.0 | 90.0 | 90.0 | 90.0 | 90.0 | 90.0 | 90.0 | 90.0 | 88.7 |
| 408 | 90.0 | 90.0 | 89.9 | 90.0 | 90.0 | 89.9 | 90.0 | 90.0 | 88.2 |
| 409 | 90.0 | 90.0 | 89.8 | 90.0 | 90.0 | 89.9 | 90.0 | 90.0 | 87.4 |
| 410 | 90.0 | 90.0 | 89.7 | 90.0 | 90.0 | 89.7 | 90.0 | 90.0 | 86.5 |
| 411 | 90.0 | 90.0 | 89.5 | 90.0 | 90.0 | 89.5 | 90.0 | 90.0 | 85.2 |
| 412 | 90.0 | 90.0 | 89.2 | 90.0 | 90.0 | 89.2 | 89.9 | 90.0 | 83.6 |

TABLE VII-continued

Two Peak Transmission Spectra
Peaks are modeled as gaussian curves
Transmission averages are simple averages which do NOT take into account the
sensitivity of the eye to weighting (luminous transmission)

| | | | | | | | | | |
|---|---|---|---|---|---|---|---|---|---|
| 413 | 90.0 | 90.0 | 88.7 | 90.0 | 90.0 | 88.8 | 89.9 | 90.0 | 81.6 |
| 414 | 90.0 | 90.0 | 87.9 | 90.0 | 90.0 | 88.1 | 89.8 | 90.0 | 79.2 |
| 415 | 90.0 | 90.0 | 86.8 | 90.0 | 90.0 | 87.0 | 89.7 | 90.0 | 76.2 |
| 416 | 90.0 | 89.9 | 85.2 | 90.0 | 90.0 | 85.5 | 89.6 | 90.0 | 72.7 |
| 417 | 90.0 | 89.7 | 83.0 | 90.0 | 89.9 | 83.5 | 89.4 | 90.0 | 68.6 |
| 418 | 90.0 | 89.4 | 80.1 | 90.0 | 89.8 | 80.8 | 89.2 | 90.0 | 64.0 |
| 419 | 90.0 | 88.9 | 76.4 | 90.0 | 89.5 | 77.3 | 88.9 | 90.0 | 58.9 |
| 420 | 90.0 | 87.8 | 71.8 | 90.0 | 89.1 | 73.0 | 88.5 | 90.0 | 53.4 |
| 421 | 90.0 | 86.0 | 66.3 | 90.0 | 88.4 | 67.9 | 88.1 | 90.0 | 47.5 |
| 422 | 90.0 | 83.2 | 60.0 | 90.0 | 87.3 | 62.0 | 87.5 | 90.0 | 41.5 |
| 423 | 90.0 | 79.2 | 53.0 | 89.9 | 85.7 | 55.6 | 87.0 | 89.9 | 35.4 |
| 424 | 89.8 | 73.8 | 45.7 | 89.6 | 83.5 | 48.8 | 86.4 | 89.4 | 29.6 |
| 425 | 89.0 | 67.1. | 38.4 | 88.3 | 80.8 | 41.9 | 85.8 | 87.8 | 24.2 |
| 426 | 87.0 | 59.7 | 31.5 | 84.9 | 77.9 | 35.5 | 85.2 | 83.2 | 19.4 |
| 427 | 82.9 | 52.3 | 25.6 | 77.7 | 74.9 | 30.0 | 84.7 | 73.8 | 15.4 |
| 428 | 76.7 | 45.9 | 20.9 | 67.0 | 72.4 | 25.7 | 84.3 | 59.7 | 12.5 |
| 429 | 70.6 | 41.5 | 18.0 | 56.5 | 70.6 | 22.9 | 84.1 | 45.9 | 10.6 |
| 430 | 68.0 | 40.0 | 17.0 | 52.0 | 70.0 | 22.0 | 84.0 | 40.0 | 10.0 |
| 431 | 70.6 | 41.5 | 18.0 | 56.5 | 70.6 | 22.9 | 84.1 | 45.9 | 10.6 |
| 432 | 76.7 | 45.9 | 20.9 | 67.0 | 72.4 | 25.7 | 84.3 | 59.7 | 12.5 |
| 433 | 82.9 | 52.3 | 25.6 | 77.7 | 74.9 | 30.0 | 84.7 | 73.8 | 15.4 |
| 434 | 87.0 | 59.7 | 31.5 | 84.9 | 77.9 | 35.5 | 85.2 | 83.2 | 19.4 |
| 435 | 89.0 | 67.1 | 38.4 | 88.3 | 80.8 | 41.9 | 85.8 | 87.8 | 24.2 |
| 436 | 89.8 | 73.8 | 45.7 | 89.6 | 83.5 | 48.8 | 86.4 | 89.4 | 29.6 |
| 437 | 90.0 | 79.2 | 53.0 | 89.9 | 85.7 | 55.6 | 87.0 | 89.9 | 35.4 |
| 438 | 90.0 | 83.2 | 60.0 | 90.0 | 87.3 | 62.0 | 87.5 | 90.0 | 41.5 |
| 439 | 90.0 | 86.0 | 66.3 | 90.0 | 88.4 | 67.9 | 88.1 | 90.0 | 47.5 |
| 440 | 90.0 | 87.8 | 71.8 | 90.0 | 89.1 | 73.0 | 88.5 | 90.0 | 53.4 |
| 441 | 90.0 | 88.9 | 76.4 | 90.0 | 89.5 | 77.3 | 88.9 | 90.0 | 58.9 |
| 442 | 90.0 | 89.4 | 80.1 | 90.0 | 89.8 | 80.8 | 89.2 | 90.0 | 64.0 |
| 443 | 90.0 | 89.7 | 83.0 | 90.0 | 89.9 | 83.5 | 89.4 | 90.0 | 68.6 |
| 444 | 90.0 | 89.9 | 85.2 | 90.0 | 90.0 | 85.5 | 89.6 | 90.0 | 72.7 |
| 445 | 90.0 | 90.0 | 86.8 | 90.0 | 90.0 | 87.0 | 89.7 | 90.0 | 76.2 |
| 446 | 90.0 | 90.0 | 87.9 | 90.0 | 90.0 | 88.1 | 89.8 | 90.0 | 79.2 |
| 447 | 90.0 | 90.0 | 88.7 | 90.0 | 90.0 | 88.8 | 89.9 | 90.0 | 81.6 |
| 448 | 90.0 | 90.0 | 89.2 | 90.0 | 90.0 | 89.2 | 89.9 | 90.0 | 83.6 |
| 449 | 90.0 | 90.0 | 89.5 | 90.0 | 90.0 | 89.5 | 90.0 | 90.0 | 85.2 |
| 450 | 90.0 | 90.0 | 89.7 | 90.0 | 90.0 | 89.7 | 90.0 | 90.0 | 86.5 |
| 451 | 90.0 | 90.0 | 89.8 | 90.0 | 90.0 | 89.9 | 90.0 | 90.0 | 87.4 |
| 452 | 90.0 | 90.0 | 89.9 | 90.0 | 90.0 | 89.9 | 90.0 | 90.0 | 88.2 |
| 453 | 90.0 | 90.0 | 90.0 | 90.0 | 90.0 | 90.0 | 90.0 | 90.0 | 88.7 |
| 454 | 90.0 | 90.0 | 90.0 | 90.0 | 90.0 | 90.0 | 90.0 | 90.0 | 89.1 |
| 455 | 90.0 | 90.0 | 90.0 | 90.0 | 90.0 | 90.0 | 90.0 | 90.0 | 89.4 |
| 456 | 90.0 | 90.0 | 90.0 | 90.0 | 90.0 | 90.0 | 90.0 | 90.0 | 89.6 |
| 457 | 90.0 | 90.0 | 90.0 | 90.0 | 90.0 | 90.0 | 90.0 | 90.0 | 89.7 |
| 458 | 90.0 | 90.0 | 90.0 | 90.0 | 90.0 | 90.0 | 90.0 | 90.0 | 89.8 |
| 459 | 90.0 | 90.0 | 90.0 | 90.0 | 90.0 | 90.0 | 90.0 | 90.0 | 89.9 |
| 460 | 90.0 | 90.0 | 90.0 | 90.0 | 90.0 | 90.0 | 90.0 | 90.0 | 89.9 |
| 461 | 90.0 | 90.0 | 90.0 | 90.0 | 90.0 | 90.0 | 90.0 | 90.0 | 90.0 |
| 462 | 90.0 | 90.0 | 90.0 | 90.0 | 90.0 | 90.0 | 90.0 | 90.0 | 90.0 |
| 463 | 90.0 | 90.0 | 90.0 | 90.0 | 90.0 | 90.0 | 90.0 | 90.0 | 90.0 |
| 464 | 90.0 | 90.0 | 90.0 | 90.0 | 90.0 | 90.0 | 90.0 | 90.0 | 90.0 |
| 465 | 90.0 | 90.0 | 90.0 | 90.0 | 90.0 | 90.0 | 90.0 | 90.0 | 90.0 |
| 466 | 90.0 | 90.0 | 90.0 | 90.0 | 90.0 | 90.0 | 90.0 | 90.0 | 90.0 |
| 467 | 90.0 | 90.0 | 90.0 | 90.0 | 90.0 | 90.0 | 90.0 | 90.0 | 90.0 |
| 468 | 90.0 | 90.0 | 90.0 | 90.0 | 90.0 | 90.0 | 90.0 | 90.0 | 90.0 |
| 469 | 90.0 | 90.0 | 90.0 | 90.0 | 90.0 | 90.0 | 90.0 | 90.0 | 90.0 |
| 470 | 90.0 | 90.0 | 89.7 | 90.0 | 90.0 | 89.7 | 90.0 | 89.8 | 89.8 |
| 471 | 90.0 | 90.0 | 89.5 | 90.0 | 90.0 | 89.5 | 90.0 | 89.7 | 89.7 |
| 472 | 90.0 | 90.0 | 89.2 | 90.0 | 90.0 | 89.1 | 90.0 | 89.4 | 89.6 |
| 473 | 90.0 | 90.0 | 88.7 | 90.0 | 90.0 | 88.6 | 90.0 | 89.1 | 89.3 |
| 474 | 90.0 | 90.0 | 87.9 | 90.0 | 90.0 | 87.7 | 90.0 | 88.6 | 88.9 |
| 475 | 90.0 | 90.0 | 86.8 | 90.0 | 89.9 | 86.5 | 90.0 | 87.8 | 88.2 |
| 476 | 90.0 | 89.9 | 85.2 | 90.0 | 89.8 | 84.7 | 90.0 | 86.7 | 87.4 |
| 477 | 90.0 | 89.7 | 83.0 | 90.0 | 89.6 | 82.3 | 90.0 | 85.2 | 86.2 |
| 478 | 90.0 | 89.4 | 80.1 | 90.0 | 89.1 | 79.2 | 90.0 | 83.2 | 84.6 |
| 479 | 90.0 | 88.9 | 76.4 | 90.0 | 88.2 | 75.1 | 90.0 | 80.7 | 82.5 |
| 480 | 90.0 | 87.8 | 71.8 | 90.0 | 86.5 | 70.1 | 90.0 | 77.5 | 80.0 |
| 481 | 90.0 | 86.0 | 66.3 | 90.0 | 83.6 | 64.0 | 90.0 | 73.8 | 77.0 |
| 482 | 90.0 | 83.2 | 60.0 | 90.0 | 79.2 | 57.1 | 90.0 | 69.4 | 73.6 |
| 483 | 90.0 | 79.2 | 53.0 | 90.0 | 72.7 | 49.5 | 89.9 | 64.7 | 69.7 |
| 484 | 89.8 | 73.8 | 45.7 | 89.9 | 64.0 | 41.5 | 89.7 | 59.7 | 65.7 |
| 485 | 89.0 | 67.1 | 38.4 | 89.8 | 53.4 | 33.5 | 88.9 | 54.7 | 61.7 |
| 486 | 87.0 | 59.7 | 31.5 | 89.3 | 41.5 | 25.9 | 86.6 | 50.0 | 58.0 |
| 487 | 82.9 | 52.3 | 25.6 | 88.4 | 29.6 | 19.4 | 81.9 | 45.9 | 54.7 |

TABLE VII-continued

Two Peak Transmission Spectra
Peaks are modeled as gaussian curves
Transmission averages are simple averages which do NOT take into account the sensitivity of the eye to weighting (luminous transmission)

| | | | | | | | | | |
|---|---|---|---|---|---|---|---|---|---|
| 488 | 76.7 | 45.9 | 20.9 | 87.0 | 19.4 | 14.3 | 74.8 | 42.7 | 52.2 |
| 489 | 70.6 | 41.5 | 18.0 | 85.6 | 12.5 | 11.1 | 67.9 | 40.7 | 50.6 |
| 490 | 68.0 | 40.0 | 17.0 | 85.0 | 10.0 | 10.0 | 65.0 | 40.0 | 50.0 |
| 491 | 70.6 | 41.5 | 18.0 | 85.6 | 12.5 | 11.1 | 67.9 | 40.7 | 50.6 |
| 492 | 76.7 | 45.9 | 20.9 | 87.0 | 19.4 | 14.3 | 74.8 | 42.7 | 52.2 |
| 493 | 82.9 | 52.3 | 25.6 | 88.4 | 29.6 | 19.4 | 81.9 | 45.9 | 54.7 |
| 494 | 87.0 | 59.7 | 31.5 | 89.3 | 41.5 | 25.9 | 86.6 | 50.0 | 58.0 |
| 495 | 89.0 | 67.1 | 38.4 | 89.8 | 53.4 | 33.5 | 88.9 | 54.7 | 61.7 |
| 496 | 89.8 | 73.8 | 45.7 | 89.9 | 64.0 | 41.5 | 89.7 | 59.7 | 65.7 |
| 497 | 90.0 | 79.2 | 53.0 | 90.0 | 72.7 | 49.5 | 89.9 | 64.7 | 69.7 |
| 498 | 90.0 | 83.2 | 60.0 | 90.0 | 79.2 | 57.1 | 90.0 | 69.4 | 73.6 |
| 499 | 90.0 | 86.0 | 66.3 | 90.0 | 83.6 | 64.0 | 90.0 | 73.8 | 77.0 |
| 500 | 90.0 | 87.8 | 71.8 | 90.0 | 86.5 | 70.1 | 90.0 | 77.5 | 80.0 |
| 501 | 90.0 | 88.9 | 76.4 | 90.0 | 88.2 | 75.1 | 90.0 | 80.7 | 82.5 |
| 502 | 90.0 | 89.4 | 80.1 | 90.0 | 89.1 | 79.2 | 90.0 | 83.2 | 84.6 |
| 503 | 90.0 | 89.7 | 83.0 | 90.0 | 89.6 | 82.3 | 90.0 | 85.2 | 86.2 |
| 504 | 90.0 | 89.9 | 85.2 | 90.0 | 89.8 | 84.7 | 90.0 | 86.7 | 87.4 |
| 505 | 90.0 | 90.0 | 86.8 | 90.0 | 89.9 | 86.5 | 90.0 | 87.8 | 88.2 |
| 506 | 90.0 | 90.0 | 87.9 | 90.0 | 90.0 | 87.7 | 90.0 | 88.6 | 88.9 |
| 507 | 90.0 | 90.0 | 88.7 | 90.0 | 90.0 | 88.6 | 90.0 | 89.1 | 89.3 |
| 508 | 90.0 | 90.0 | 89.2 | 90.0 | 90.0 | 89.1 | 90.0 | 89.4 | 89.6 |
| 509 | 90.0 | 90.0 | 89.5 | 90.0 | 90.0 | 89.5 | 90.0 | 89.7 | 89.7 |
| 510 | 90.0 | 90.0 | 89.7 | 90.0 | 90.0 | 89.7 | 90.0 | 89.8 | 89.8 |
| 511 | 90.0 | 90.0 | 89.8 | 90.0 | 90.0 | 89.8 | 90.0 | 89.9 | 89.9 |
| 512 | 90.0 | 90.0 | 89.9 | 90.0 | 90.0 | 89.9 | 90.0 | 89.9 | 90.0 |
| 513 | 90.0 | 90.0 | 90.0 | 90.0 | 90.0 | 89.9 | 90.0 | 90.0 | 90.0 |
| Average | 85.0 | 83.0 | 80.0 | 85.0 | 83.0 | 80.0 | 85.0 | 83.0 | 80.0 |

TABLE VIII

Two Peak Transmission Spectra
Peaks are modeled as gaussian curves
Transmission averages are simple averages which do NOT take into account the sensitivity of the eye to weighting (luminous transmission)

| | More blockage at 430 nm | | | More blockage at 490 nm | | |
|---|---|---|---|---|---|---|
| Scenario | 10 | 11 | 12 | 13 | 14 | 15 |
| Average | 84.6 | 83.5 | 82.5 | 84.6 | 83.5 | 82.5 |
| Peak1 Scale | 50 | 60 | 70 | 25 | 20 | 10 |
| Peak2 Scale | 25 | 20 | 10 | 50 | 60 | 70 |
| St. Deviation1 | 2 | 4 | 6 | 2 | 4 | 6 |
| St. Devation2 | 2 | 4 | 6 | 2 | 4 | 6 |
| Wavelength | T (%) | T (%) | T (%) | T (%) | T (%) | T (%) |
| 380 | 0 | 0 | 0 | 0 | 0 | 0 |
| 381 | 0 | 0 | 0 | 0 | 0 | 0 |
| 382 | 0 | 0 | 0 | 0 | 0 | 0 |
| 383 | 0 | 0 | 0 | .0 | 0 | 0 |
| 384 | 0 | 0 | 0 | 0 | 0 | 0 |
| 385 | 0 | 0 | 0 | 0 | 0 | 0 |
| 386 | 0 | 0 | 0 | 0 | 0 | 0 |
| 387 | 0 | 0 | 0 | 0 | 0 | 0 |
| 388 | 0 | 0 | 0 | 0 | 0 | 0 |
| 389 | 0 | 0 | 0 | 0 | 0 | 0 |
| 390 | 0 | 0 | 0 | 0 | 0 | 0 |
| 391 | 0 | 0 | 0 | 0 | 0 | 0 |
| 392 | 0 | 0 | 0 | 0 | 0 | 0 |
| 393 | 0 | 0 | 0 | 0 | 0 | 0 |
| 394 | 0 | 0 | 0 | 0 | 0 | 0 |
| 395 | 0 | 0 | 0 | 0 | 0 | 0 |
| 396 | 0 | 0 | 0 | 0 | 0 | 0 |
| 397 | 0 | 0 | 0 | 0 | 0 | 0 |
| 398 | 0 | 0 | 0 | 0 | 0 | 0 |
| 399 | 0 | 0 | 0 | 0 | 0 | 0 |
| 400 | 90.0 | 90.0 | 90.0 | 90.0 | 90.0 | 90.0 |
| 401 | 90.0 | 90.0 | 90.0 | 90.0 | 90.0 | 90.0 |
| 402 | 90.0 | 90.0 | 90.0 | 90.0 | 90.0 | 90.0 |
| 403 | 90.0 | 90.0 | 90.0 | 90.0 | 90.0 | 90.0 |
| 404 | 90.0 | 90.0 | 90.0 | 90.0 | 90.0 | 90.0 |
| 405 | 90.0 | 90.0 | 90.0 | 90.0 | 90.0 | 90.0 |
| 406 | 90.0 | 90.0 | 90.0 | 90.0 | 90.0 | 90.0 |
| 407 | 90.0 | 90.0 | 90.0 | 90.0 | 90.0 | 90.0 |
| 408 | 90.0 | 90.0 | 89.9 | 90.0 | 90.0 | 90.0 |
| 409 | 90.0 | 90.0 | 89.8 | 90.0 | 90.0 | 90.0 |
| 410 | 90.0 | 90.0 | 89.7 | 90.0 | 90.0 | 90.0 |
| 411 | 90.0 | 90.0 | 89.5 | 90.0 | 90.0 | 89.9 |
| 412 | 90.0 | 90.0 | 89.2 | 90.0 | 90.0 | 89.9 |
| 413 | 90.0 | 90.0 | 88.7 | 90.0 | 90.0 | 89.8 |
| 414 | 90.0 | 90.0 | 88.0 | 90.0 | 90.0 | 89.7 |
| 415 | 90.0 | 89.9 | 86.9 | 90.0 | 90.0 | 89.6 |
| 416 | 90.0 | 89.9 | 85.4 | 90.0 | 90.0 | 89.3 |
| 417 | 90.0 | 89.7 | 83.3 | 90.0 | 89.9 | 89.0 |
| 418 | 90.0 | 89.3 | 80.5 | 90.0 | 89.8 | 88.6 |
| 419 | 90.0 | 88.6 | 77.0 | 90.0 | 89.5 | 88.1 |
| 420 | 90.0 | 87.4 | 72.5 | 90.0 | 89.1 | 87.5 |
| 421 | 90.0 | 85.2 | 67.3 | 90.0 | 88.4 | 86.8 |
| 422 | 90.0 | 81.9 | 61.2 | 90.0 | 87.3 | 85.9 |
| 423 | 89.9 | 77.0 | 54.6 | 89.9 | 85.7 | 84.9 |
| 424 | 89.4 | 70.5 | 47.5 | 89.7 | 83.5 | 83.9 |
| 425 | 87.8 | 62.5 | 40.5 | 88.9 | 80.8 | 82.9 |
| 426 | 83.2 | 53.6 | 33.9 | 86.6 | 77.9 | 82.0 |
| 427 | 73.8 | 44.7 | 28.2 | 81.9 | 74.9 | 81.2 |
| 428 | 59.7 | 37.1 | 23.8 | 74.8 | 72.4 | 80.5 |
| 429 | 45.9 | 31.8 | 21.0 | 67.9 | 70.6 | 80.1 |
| 430 | 40.0 | 30.0 | 20.0 | 65.0 | 70.0 | 80.0 |
| 431 | 45.9 | 31.8 | 21.0 | 67.9 | 70.6 | 80.1 |
| 432 | 59.7 | 37.1 | 23.8 | 74.8 | 72.4 | 80.5 |
| 433 | 73.8 | 44.7 | 28.2 | 81.9 | 74.9 | 81.2 |
| 434 | 83.2 | 53.6 | 33.9 | 86.6 | 77.9 | 82.0 |
| 435 | 87.8 | 62.5 | 40.5 | 88.9 | 80.8 | 82.9 |
| 436 | 89.4 | 70.5 | 47.5 | 89.7 | 83.5 | 83.9 |
| 437 | 89.9 | 77.0 | 54.6 | 89.9 | 85.7 | 84.9 |
| 438 | 90.0 | 81.9 | 61.2 | 90.0 | 87.3 | 85.9 |
| 439 | 90.0 | 85.2 | 67.3 | 90.0 | 88.4 | 86.8 |
| 440 | 90.0 | 87.4 | 72.5 | 90.0 | 89.1 | 87.5 |

TABLE VIII-continued

Two Peak Transmission Spectra
Peaks are modeled as gaussian curves
Transmission averages are simple averages which do NOT take into
account the sensitivity of the eye to weighting (luminous transmission)

| | | | | | | |
|---|---|---|---|---|---|---|
| 441 | 90.0 | 88.6 | 77.0 | 90.0 | 89.5 | 88.1 |
| 442 | 90.0 | 89.3 | 80.5 | 90.0 | 89.8 | 88.6 |
| 443 | 90.0 | 89.7 | 83.3 | 90.0 | 89.9 | 89.0 |
| 444 | 90.0 | 89.9 | 85.4 | 90.0 | 90.0 | 89.3 |
| 445 | 90.0 | 89.9 | 86.9 | 90.0 | 90.0 | 89.6 |
| 446 | 90.0 | 90.0 | 88.0 | 90.0 | 90.0 | 89.7 |
| 447 | 90.0 | 90.0 | 88.7 | 90.0 | 90.0 | 89.8 |
| 448 | 90.0 | 90.0 | 89.2 | 90.0 | 90.0 | 89.9 |
| 449 | 90.0 | 90.0 | 89.5 | 90.0 | 90.0 | 89.9 |
| 450 | 90.0 | 90.0 | 89.7 | 90.0 | 90.0 | 90.0 |
| 451 | 90.0 | 90.0 | 89.8 | 90.0 | 90.0 | 90.0 |
| 452 | 90.0 | 90.0 | 89.9 | 90.0 | 90.0 | 90.0 |
| 453 | 90.0 | 90.0 | 90.0 | 90.0 | 90.0 | 90.0 |
| 454 | 90.0 | 90.0 | 90.0 | 90.0 | 90.0 | 90.0 |
| 455 | 90.0 | 90.0 | 90.0 | 90.0 | 90.0 | 90.0 |
| 456 | 90.0 | 90.0 | 90.0 | 90.0 | 90.0 | 90.0 |
| 457 | 90.0 | 90.0 | 90.0 | 90.0 | 90.0 | 90.0 |
| 458 | 90.0 | 90.0 | 90.0 | 90.0 | 90.0 | 90.0 |
| 459 | 90.0 | 90.0 | 90.0 | 90.0 | 90.0 | 90.0 |
| 460 | 90.0 | 90.0 | 90.0 | 90.0 | 90.0 | 90.0 |
| 461 | 90.0 | 90.0 | 90.0 | 90.0 | 90.0 | 90.0 |
| 462 | 90.0 | 90.0 | 90.0 | 90.0 | 90.0 | 90.0 |
| 463 | 90.0 | 90.0 | 90.0 | 90.0 | 90.0 | 90.0 |
| 464 | 90.0 | 90.0 | 90.0 | 90.0 | 90.0 | 90.0 |
| 465 | 90.0 | 90.0 | 90.0 | 90.0 | 90.0 | 90.0 |
| 466 | 90.0 | 90.0 | 90.0 | 90.0 | 90.0 | 90.0 |
| 467 | 90.0 | 90.0 | 90.0 | 90.0 | 90.0 | 90.0 |
| 468 | 90.0 | 90.0 | 90.0 | 90.0 | 90.0 | 90.0 |
| 469 | 90.0 | 90.0 | 90.0 | 90.0 | 90.0 | 90.0 |
| 470 | 90.0 | 90.0 | 90.0 | 90.0 | 90.0 | 89.7 |
| 471 | 90.0 | 90.0 | 89.9 | 90.0 | 90.0 | 89.5 |
| 472 | 90.0 | 90.0 | 89.9 | 90.0 | 90.0 | 89.2 |
| 473 | 90.0 | 90.0 | 89.8 | 90.0 | 90.0 | 88.7 |
| 474 | 90.0 | 90.0 | 89.7 | 90.0 | 90.0 | 88.0 |
| 475 | 90.0 | 90.0 | 89.6 | 90.0 | 89.9 | 86.9 |
| 476 | 90.0 | 90.0 | 89.3 | 90.0 | 89.9 | 85.4 |
| 477 | 90.0 | 89.9 | 89.0 | 90.0 | 89.7 | 83.3 |
| 478 | 90.0 | 89.8 | 88.6 | 90.0 | 89.3 | 80.5 |
| 479 | 90.0 | 89.5 | 88.1 | 90.0 | 88.6 | 77.0 |
| 480 | 90.0 | 89.1 | 87.5 | 90.0 | 87.4 | 72.5 |
| 481 | 90.0 | 88.4 | 86.8 | 90.0 | 85.2 | 67.3 |
| 482 | 90.0 | 87.3 | 85.9 | 90.0 | 81.9 | 61.2 |
| 483 | 89.9 | 85.7 | 84.9 | 89.9 | 77.0 | 54.6 |
| 484 | 89.7 | 83.5 | 83.9 | 89.4 | 70.5 | 47.5 |
| 485 | 88.9 | 80.8 | 82.9 | 87.8 | 62.5 | 40.5 |
| 486 | 86.6 | 77.9 | 82.0 | 83.2 | 53.6 | 33.9 |
| 487 | 81.9 | 74.9 | 81.2 | 73.8 | 44.7 | 28.2 |
| 488 | 74.8 | 72.4 | 80.5 | 59.7 | 37.1 | 23.8 |
| 489 | 67.9 | 70.6 | 80.1 | 45.9 | 31.8 | 21.0 |
| 490 | 65.0 | 70.0 | 80.0 | 40.0 | 30.0 | 20.0 |
| 491 | 67.9 | 70.6 | 80.1 | 45.9 | 31.8 | 21.0 |
| 492 | 74.8 | 72.4 | 80.5 | 59.7 | 37.1 | 23.8 |
| 493 | 81.9 | 74.9 | 81.2 | 73.8 | 44.7 | 28.2 |
| 494 | 86.6 | 77.9 | 82.0 | 83.2 | 53.6 | 33.9 |
| 495 | 88.9 | 80.8 | 82.9 | 87.8 | 62.5 | 40.5 |
| 496 | 89.7 | 83.5 | 83.9 | 89.4 | 70.5 | 47.5 |
| 497 | 89.9 | 85.7 | 84.9 | 89.9 | 77.0 | 54.6 |
| 498 | 90.0 | 87.3 | 85.9 | 90.0 | 81.9 | 61.2 |
| 499 | 90.0 | 88.4 | 86.8 | 90.0 | 85.2 | 67.3 |
| 500 | 90.0 | 89.1 | 87.5 | 90.0 | 87.4 | 72.5 |
| 501 | 90.0 | 89.5 | 88.1 | 90.0 | 88.6 | 77.0 |
| 502 | 90.0 | 89.8 | 88.6 | 90.0 | 89.3 | 80.5 |
| 503 | 90.0 | 89.9 | 89.0 | 90.0 | 89.7 | 83.3 |
| 504 | 90.0 | 90.0 | 89.3 | 90.0 | 89.9 | 85.4 |
| 505 | 90.0 | 90.0 | 89.6 | 90.0 | 89.9 | 86.9 |
| 506 | 90.0 | 90.0 | 89.7 | 90.0 | 90.0 | 88.0 |
| 507 | 90.0 | 90.0 | 89.8 | 90.0 | 90.0 | 88.7 |
| 508 | 90.0 | 90.0 | 89.9 | 90.0 | 90.0 | 89.2 |
| 509 | 90.0 | 90.0 | 89.9 | 90.0 | 90.0 | 89.5 |
| 510 | 90.0 | 90.0 | 90.0 | 90.0 | 90.0 | 89.7 |
| 511 | 90.0 | 90.0 | 90.0 | 90.0 | 90.0 | 89.8 |
| 512 | 90.0 | 90.0 | 90.0 | 90.0 | 90.0 | 89.9 |
| 513 | 90.0 | 90.0 | 90.0 | 90.0 | 90.0 | 90.0 |
| Average | 84.6 | 83.5 | 82.5 | 84.6 | 83.5 | 82.5 |

Thus, in a further embodiment of the invention, an ophthalmic lens may include a dye that causes the lens to selectively inhibit transmission of visible light in at least two different ranges of wavelengths selected from the range of 450±50 nm. The transmission spectrum would demonstrate two distinct valleys with a region of higher transmission between the two valleys. For example see FIG. 48A-O. More preferably, the dye would selectively inhibit transmission of visible light having a wavelength of X1±15 nm and light having a wavelength of X2±15 nm, where X1 is a wavelength in the range of 415-485 nm and X2 is a wavelength different from X1 and in the range of 415-485 nm. More preferably, the dye would cause the lens to block at least 5% or preferably 10%, or more preferably 20%, or more preferably 30%, or most preferably 40% of light within the specified wavelengths.

It is a further embodiment of the invention to use a film or more than one film in an ophthalmic or non-ophthalmic system may selectively inhibit at least 5%, at least 10%, at least 20%, at least 25%, at least 30%, at least 40%, at least 50%, and/or at least 60% of light between about 400 nm to about 500 nm or less than 500 nm.

The invention can be enabled by various means. By way of example only the film or films could be: one or more AR coatings, more than one primer coat, more than one hard coat or scratch resistant coating, one or more hydrophobic coating(s), a cosmetic or visibility tinted contact lens (one or more colors) with either solid color or colors across the entire lens or less than the entire lens, zones of color or colors in a contact lens, or a ring or rings of color in a contact lens.

Other components of the film or films could include carotenoids, either in a natural or synthetic or derivative state. By way of example only, lutein and zeaxanthin are carotenoids and are organic pigments that occur naturally in plants. They are exclusively derived from nutritional origin and are not synthesized in the body. Lutein and zeaxanthin selectively accumulate in ocular tissues, including the lens and the macula. The macular pigment provides a protective role in inhibiting damaging wavelengths within the blue light visible spectrum. The macular pigment contains higher concentrations of lutein and zeaxanthin than any other structure in the human body.

Furthermore, synthetic or non-synthetic antioxidants or derivatives can also enable the invention. By way of example only: trans-resveratrol, epigallocatechin gallate (EGCG), coenzyme Q10 (CoQ10), vitamins A, C, D, and E, and omega-3 fatty acids could be incorporated into the film or films. Zinc could also be incorporated into the film.

Another embodiment could include dyes, as described in U.S. Pat. No. 7,556,376 assigned to High Performance Optics in more than one film.

Applications for the film or films are wide reaching. Virtually any device or system that transmits light or light passes through filtered or unfiltered before reaching the eye or retina can be enabled with the invention. By way of example only: all ophthalmic devices in all materials are included such as ophthalmic prescription and non-prescription eyeglasses and sunglasses, contact lenses, IOL's, corneal implants, corneal inlays, corneal onlays, electro-active devices, photochromic glasses, all types of contact lenses, and composites.

Other applications could include by way of example only: any type of windows, automotive windshields, aircraft windows, camera flash bulbs and lenses, any type of artificial lighting fixture (either the fixture or the filament or both), fluorescent lighting or any type of diffuser, medical instruments, surgical instruments, rifle scopes, binoculars, computer monitors, televisions screens, lighted signs or any other item or system whereby light is emitted or is transmitted or passes through filtered or unfiltered.

The film or films can be made of any material or materials known in the art. U.S. Pat. No. 7,556,376 (assigned to High Performance Optics) describes various film types. Photopic luminous transmission and phototoxicity measurements are described in U.S. Pat. No. 7,556,376 assigned to High Performance Optics.

It is now well known that both UV and blue light are implicated in eye and skin disease. Blue light is implicated in retina disease, primarily macular degeneration. In the eye varying the concentration of blue light blocking dye in about the 400-460 nm range has a direct correlation with the level of retina protection. A sunglass would provide the greatest protection. For example, the Waterman's sunglass lens, U.S. Pat. No. 7,029,118 by Ishak exhibits 0.34% average blue light transmission. In designing a mostly clear ophthalmic (non-sunglass lens) lens with 80% or greater light transmission across the visible spectrum, select blue light wavelengths are targeted to maximize retinal protection and provide acceptable lens cosmetics.

Laboratory evidence by Sparrow at Columbia University has shown that that if about 50% of the blue light within the wavelength range of 430±30 nm range is blocked, RPE cell death caused by the blue light exposure may be reduced by up to 80%. This level of blocking would require a level of dye concentration that would not be acceptable in an ophthalmic eyeglass lens, especially with regard to night driving, color vision, lens cosmetics, and possibly circadian rhythms.

Figure 50:
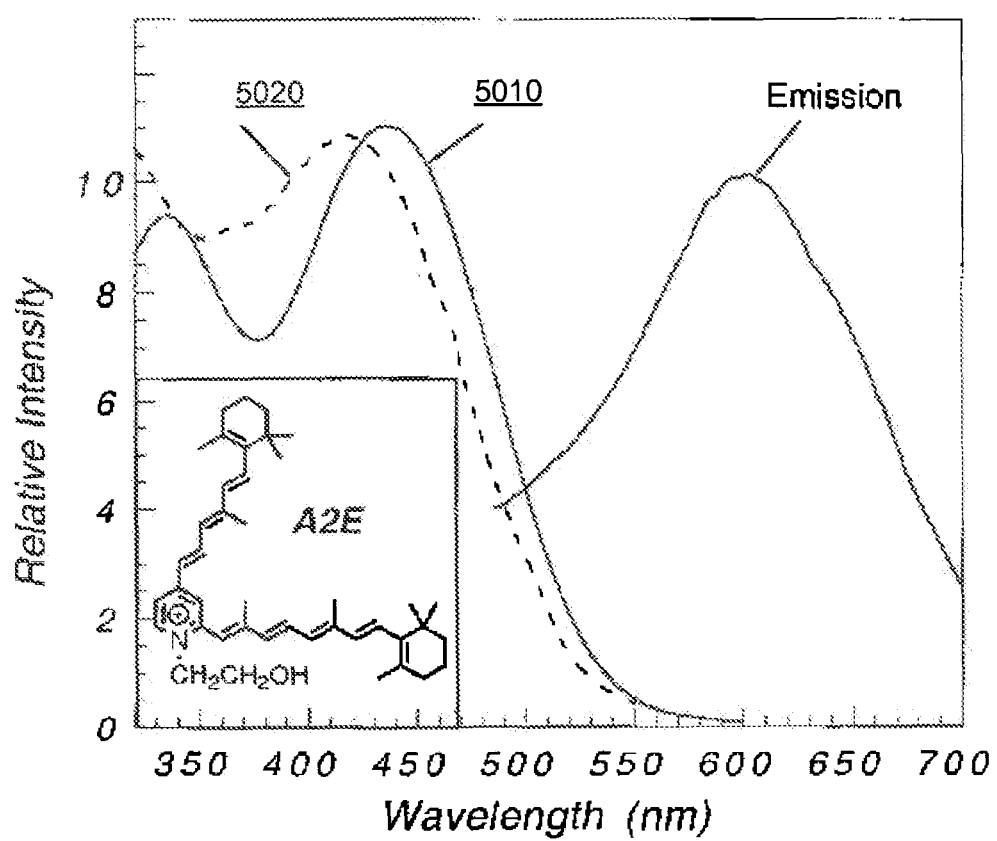
FIG. 50 shows the UV/visible light, excitation, and emission spectra of A2E in methanol.

The UV/visible light, excitation, and emission spectra of A2E in methanol are shown in FIG. 50. The absorbance spectrum 5010 has a major peak at 435 nm and the excitation spectrum, monitored at 600 nm emission, had a maximum at 418 nm 5020.

Figure 51:
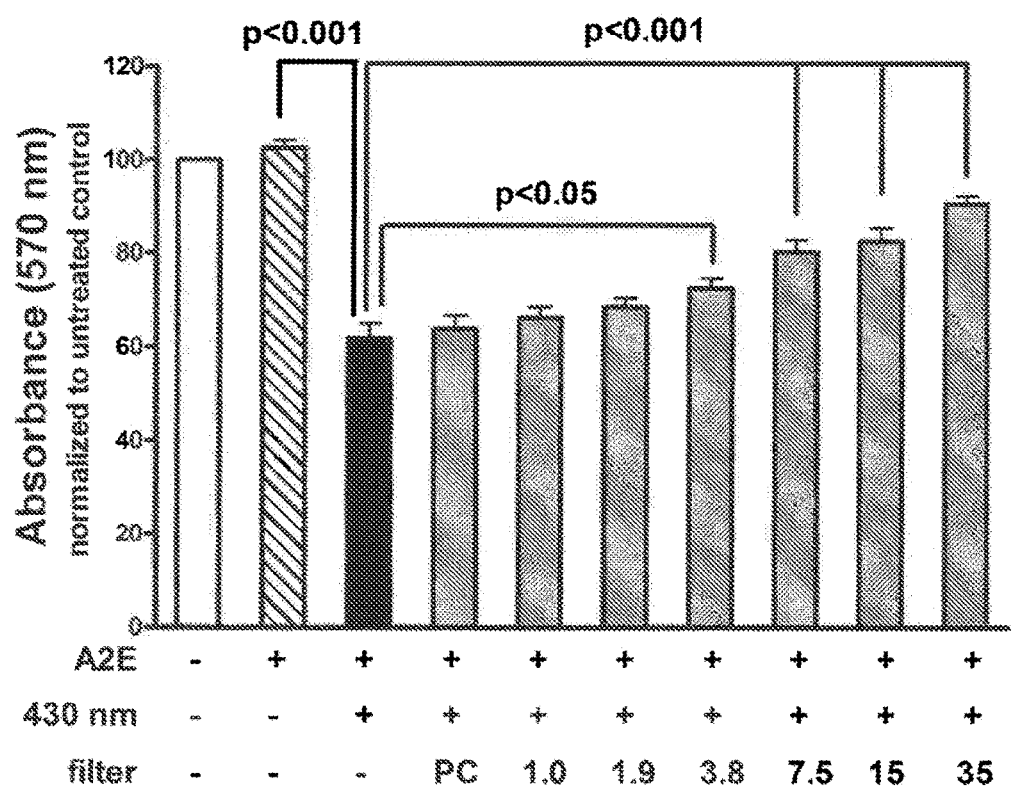
FIG. 51 shows cell viability in irradiated (430 nm) cultures of ARPE-19 cells.
Figure 52:
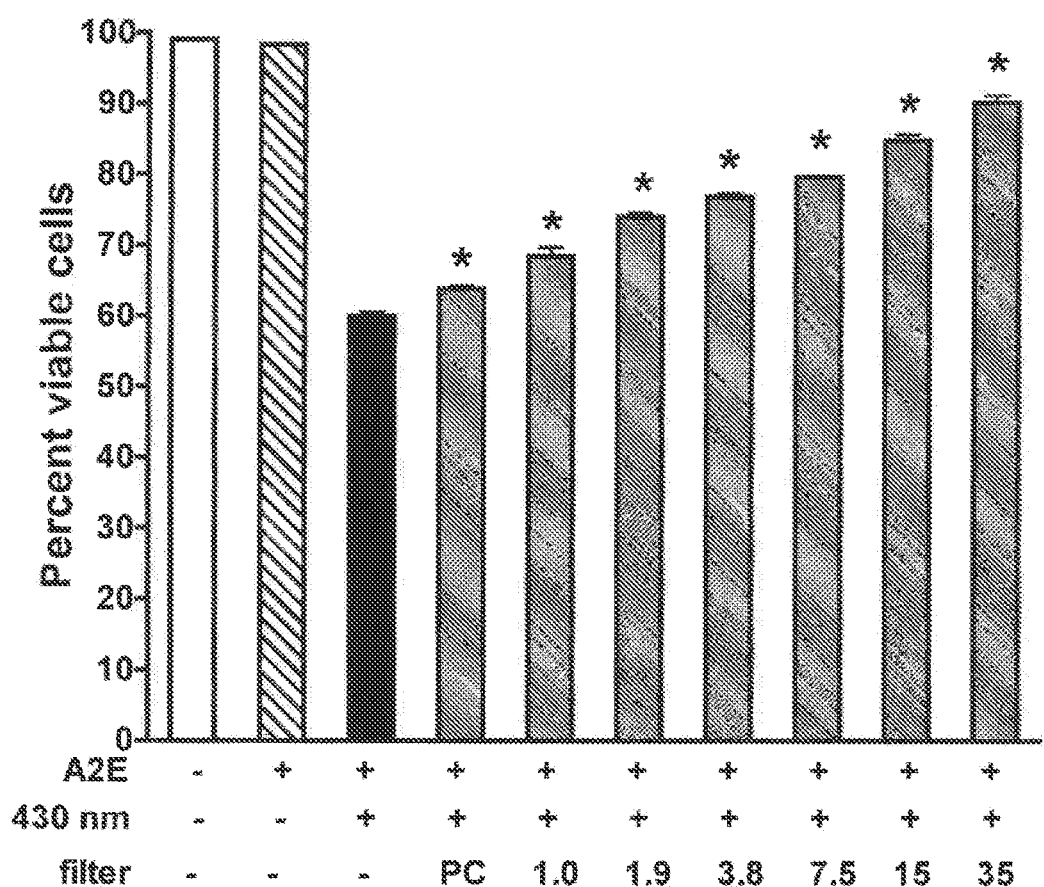
FIG. 52 shows quantification of viable RPE cells after A2E accumulation and blue light illumination (430 nm).

Further laboratory evidence by Sparrow at Columbia University for High Performance Optics has shown that concentrations of blue light filtering dyes with levels as low as 1.0 ppm and 1.9 ppm can provide retinal benefit in a mostly colorless system, "Light Filtering in Retinal Pigment Epithelial Cell Culture Model" Optometry and Vision Science 88; 6 (2011): 1-7, is referenced in its entirety. As shown in FIGS. 51 and 52 in this report it is possible to vary the concentration of the filter system to a level of 1.0 ppm or greater to a level of about 35 ppm as exampled with perylene dye. Any concentration level between about 1.0 ppm or greater to about 35 ppm can enable the invention. Other dyes that exhibit similar blue light blocking function could also be used with similar variable dye concentration levels.

FIG. 51 shows cell viability in irradiated (430 nm) cultures of ARPE-19 cells that had accumulated A2E. Filters containing variable levels of dye (approximately 1.0 ppm, 1.9 ppm, 3.8 ppm, 7.5 ppm, 15 ppm, and 35 ppm) or no dye (PC) were placed in the light path. Viability was quantified by MTT assay and the bar height is indicate of MTT absorbance and reflects viability. The mean is ±SEM of 5 experiments.

FIG. 52 shows quantification of viable RPE cells after A2E accumulation and blue light illumination (430 nm), with and without a blue-light absorbing filter placed in the light path. Filter contained variable levels of dye (approximately 1.0 ppm, 1.9 ppm, 3.8 ppm, 7.5 ppm, 15 ppm, and 35 ppm) or no dye (PC). The percent of viable cells was determined by labeling all nuclei with DAPI and the nuclei of nonviable cells with a membrane-impermeable dye. The data were normalized to values determined in the absence of a filter and are presented as percent viable cells. In FIG. 52 $p<0.001$ as compared to A2E, 430 nm and the mean is ±SEM of 3 experiments.

In some cases it may be particularly desirable reduce the action spectrum of A3E, which has been shown by Sparrow, "The Lipofuscin Fluorophore A2E Mediates Blue Light-Induced Damage to Retinal Pigmented Epithelial Cells," Optometry and Vision Science 41; 7 (2000): 1981-89, to have a major peak in the absorbance spectrum at 435 nm, FIG. 50.

It is another embodiment of this invention to inhibit visible light between 435±20 nm in an ophthalmic lens such as a contact, intraocular lens or spectacle lens. Other ophthalmic lenses, for example those discussed previously, may also be utilized. It is another embodiment of this invention to inhibit visible light between 435±20 nm in a non-ophthalmic system.

Many dyes, synthetic or non-synthetic and/or any derivative(s) or combination of such can enable the embodiments of the invention whereby the absorption curve design yields on or more peaks within about the 400-460 nm range with 80% or greater visible light transmission. In other embodiments the wavelength range is about 400-500 nm. In other embodiments the wavelength range is about 400-475 nm. By way of example, the following filters, dyes, or antioxidants could be used to enable the invention: perylene; magnesium tetraphenyl porphyrin, coumarin 6, coumarin 30, yellow orange, acridyne acridyne, lutein, zeaxanthin, and melanin. Many filter(s), dye(s), or any anti-oxidant(s) can be included in one or more combinations to enable the invention. One of skill in the art, with the guidance provided herein, can select appropriate materials and incorporate them into an ophthalmic or non-ophthalmic structure in an appropriate amount.

Figure 53:
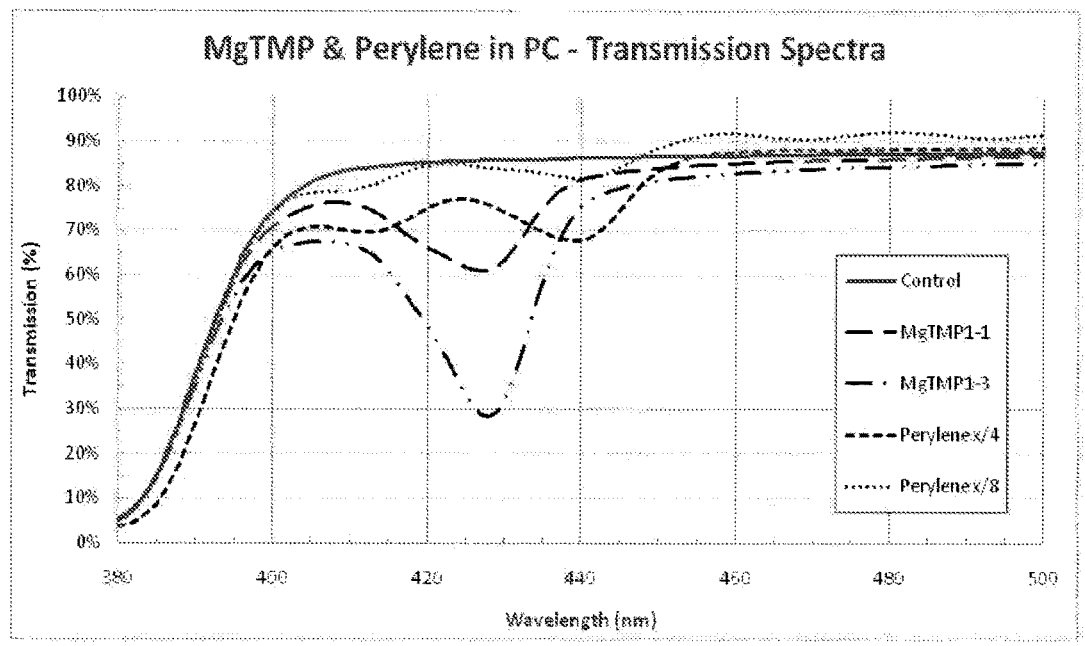
FIG. 53 shows the transmission spectra of MgTPP and Perylene in polycarbonate.

For example, in FIG. 53 perylene and magnesium tetraphenyl porphyrin (MgTPP) are shown with varying concentration levels. Any modification of the concentration level is possible as long as light transmission of 80% or greater across the visible light transmission is achieved. In a photochromic system this would be in an unactivated (indoor) state.

In other embodiments of the invention, targeted wavelengths could be chosen to promote the integrity of the RPE and/or the macular pigment. With regard to the RPE, one or more than one lipofuscin chromophores can be targeted.

An ophthalmic system by way of example can include: a sunglass lens, eyeglass lens, photochromic lens, any type of a contact lens with and without visibility tinting and/or cosmetic tinting, intra-ocular lens, corneal onlay, corneal inlay, and electroactive lenses.

Any type of chemical hook or hooks or other method or methods or combination of methods to reduce or eliminate dye leaching in any system can be added to embodiments of the invention.

Other embodiments of the invention could include yellowness index levels such as ASTM E313-05. Preferably the selective filter has a yellowness index level that is no more than 50, 40, 35, 30, 25, 23, 20, 15, 10, 9, 7, or 5.

The invention can be enabled by any means known in the ophthalmic industry. By way of example only one or more AR coats, one or more films, one or more hard coats, one or more primer coats, one or more hydrophobic coats or any combination of coatings, films, or dyes can enable the invention.

Other embodiments of the invention include dermatologic application. By way of example only, the selective blue light filter can be included in: any skin or hair product, suntan and sunscreen products, lip stick, lip balm, anti-ageing products, oils, or acne products.

In other embodiments, non-ophthalmic systems can be enabled by the invention. Any non-ophthalmic system whereby, light transmits through or from the non-ophthalmic system can be enabled by the invention. By way of example only, a non-ophthalmic system could include: automobile windows and windshields, aircraft windows and windshields, any type of window, computer monitors, televisions, medical instruments, diagnostic instruments, lighting products, fluorescent lighting, or any type of lighting product or light diffuser.

Any amount of light that reaches the retina can be filtered by embodiments of the invention and can be included in any type of system: ophthalmic, non-ophthalmic, dermatological, or industrial.

Other embodiments of the invention include a wide variation in how the selective filter can be added to any system in varying concentrations and/or zones and/or rings. For example, in an eyeglass lens the select filter does not necessarily need to be uniform throughout the entire system or in any fixed concentration. An ophthalmic lens could have one or more zones and/or rings of varying filter concentration or any combination of such.

In other embodiments the filter can be uniform or mostly uniform throughout the system.

In other embodiments, one or more layers of the filter can be used to enable the invention.

One concern for dyes which selectively filter light in the blue region of the visible light spectrum is that this absorption may affect the color of the light in transmission. Anytime that some wavelengths are filtered relative to others, there will be a difference in the spectrum of light which enters the eye after passing through the lens (filter). Depending on the magnitude of the changes at specific wavelengths, this filtering may cause imperceptible or perceptible changes in color. While each individual's eyes are unique, the effects to an average observer can be estimated by using mathematical models which account the color perception for typical human observers.

Spectral transmission data measured using the Ocean Optics USB 200 spectrometer from 380-780 nm at 1 nm increments for perylene- and MgTMP•dyed lenses. The spectrometer software automatically calculated the average transmission, $T_{avg}$, the luminous transmission, $T_v$, and the color parameters L*, a*, b*, hue angle, and chroma. The transmission at 430 nm ($T_{430}$), the average transmission over the range 415-430 nm ($T_{415\text{-}430}$), and the yellowness index (YI) were calculated using an excel spreadsheet.

The lenses measured were demo lenses created in Fall 2010 with the following characteristics:

Perylene-dyed ODC Lens Material Semi-Finished Blanks Surfaced to 2.1 mm and backcoated (2 ppm, 3 ppm, and 4 ppm dye)

MgTMP-dyed polycarbonate molded/coated samples from NoIR at dye levels of 1.8 and 3.7 ppm.

The yellowness index was calculated using the transmission data, equation 1, and the coefficients in ASTM E313-05 see Table IX below. Yellowness index was calculated assuming a CIE-$D_{65}$ light source with 1931 (2° viewing angle) standard illuminant factors.

$$YI = 100(C_x X - C_z Z)/Y \quad (1)$$

where X, Y, and Z are the CIE Tristimulus values and the coefficients depend on the illuminant and observer as indicated in Table IX below from the ASTM E313-05 standard. The 1964 $D_{65}$ standard illuminant factors are for a 10° viewing angle. Table IX shows the coefficients of the equations for the yellowness index.

TABLE IX

| | CIE Standard Illuminant and Standard Observer | | | |
|---|---|---|---|---|
| Quantity | C, 1931 | $D_{65}$, 1931 | C, 1964 | $D_{65}$, 1964 |
| $X_n$ | 98.074 | 95.047 | 97.285 | 94.811 |
| $Y_n$ | 100.000 | 100.000 | 100.000 | 100.000 |
| $Z_n$ | 118.232 | 108.883 | 116.145 | 107.304 |
| $F_A$ | 0.7987 | 0.8105 | 0.7987 | 0.8103 |
| $F_B$ | 0.2013 | 0.1895 | 0.2013 | 0.1897 |
| $C_x$ | 1.2769 | 1.2985 | 1.2871 | 1.3013 |
| $C_z$ | 1.0592 | 1.1335 | 1.0781 | 1.1498 |
| Residual error | −0.0006 | −0.0004 | −0.0004 | −0.0006 |

Figure 54:
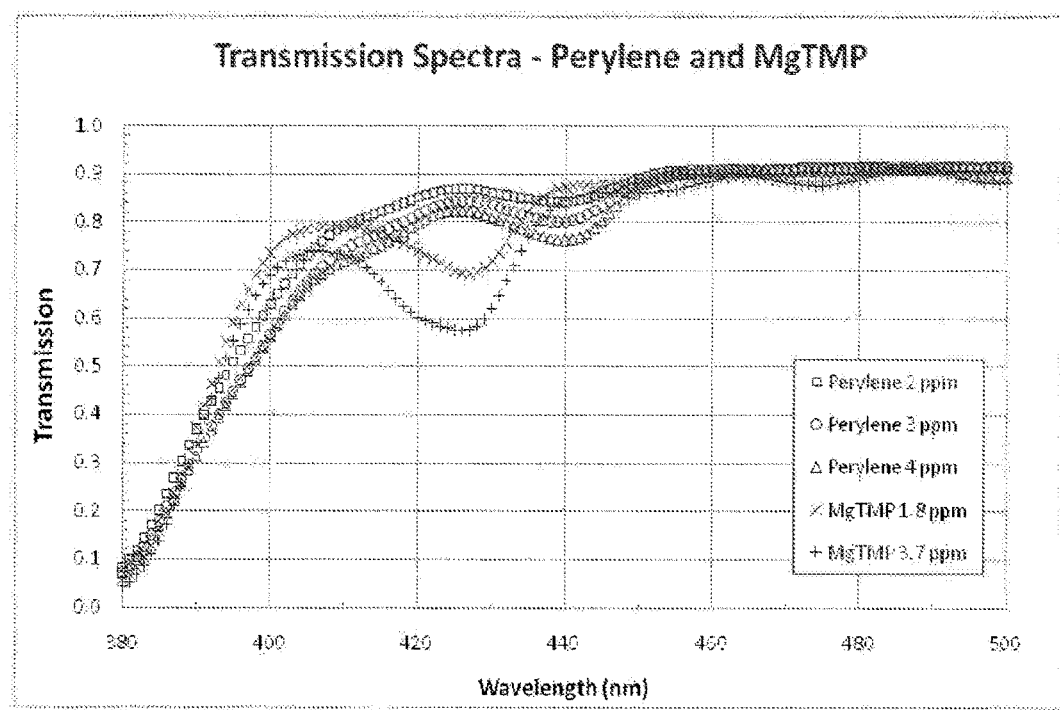
FIG. 54 shows transmission spectra of MgTPP and Perylene for example lenses.

The summary of the measured and calculated data is shown in Tables X and XI below. The yellowness index was only calculated for a few of the samples. FIG. 54 shows the transmission spectra for representative lenses at each dye level.

TABLE X

| Description | Tavg | Tv | T430 | T415-430 | L | a* | b* | Hue (•) | Chroma | YI (E313-05) |
|---|---|---|---|---|---|---|---|---|---|---|
| Air | 100.0% | 100.0% | 100.0% | 100.0% | 100.01 | 0.01 | 0.01 | 68.4 | 0.0 | |
| c-1 | 87.5% | 91.0% | 89.6% | 89.0% | 96.42 | −0.41 | 0.70 | 120.6 | 0.8 | 0.8 |
| c-2 | 87.8% | 91.1% | 90.1% | 89.8% | 96.45 | −0.29 | 0.48 | 121.0 | 0.6 | |
| 2ppm1 | 87.7% | 91.1% | 86.2% | 85.4% | 96.44 | −1.01 | 2.06 | 116.1 | 2.3 | 2.8 |
| 2ppm2 | 87.1% | 91.0% | 85.4% | 84.3% | 96.40 | −1.20 | 2.40 | 116.6 | 2.7 | 3.2 |
| 2ppm3 | 87.7% | 91.2% | 86.2% | 85.2% | 96.47 | −1.08 | 2.14 | 116.9 | 2.4 | |
| 2ppm4 | 87.6% | 91.1% | 86.1% | 84.9% | 96.43 | −1.10 | 2.18 | 116.8 | 2.4 | |
| 2ppm5 | 87.2% | 91.2% | 85.4% | 84.5% | 96.45 | −1.20 | 2.33 | 117.1 | 2.6 | |
| 2ppm6 | 87.4% | 91.2% | 86.1% | 84.9% | 96.44 | −1.10 | 2.21 | 116.5 | 2.5 | |
| 2ppm7 | 87.6% | 91.3% | 86.1% | 85.1% | 96.49 | −1.08 | 2.22 | 115.9 | 2.5 | |
| 2ppm8 | 87.4% | 91.1% | 85.8% | 84.8% | 96.43 | −1.14 | 2.27 | 116.7 | 2.5 | |
| 3ppm1 | 86.7% | 91.1% | 82.9% | 81.5% | 96.39 | −1.65 | 3.39 | 116.0 | 3.8 | 4.5 |
| 3ppm2 | 86.8% | 91.0% | 83.2% | 81.7% | 96.36 | −1.60 | 3.32 | 115.7 | 3.7 | 4.5 |
| 3ppm3 | 87.0% | 91.1% | 83.6% | 81.9% | 96.42 | −1.64 | 3.29 | 116.4 | 3.7 | |
| 3ppm4 | 86.9% | 91.1% | 83.4% | 82.0% | 96.39 | −1.60 | 3.24 | 116.3 | 3.6 | |
| 3ppm5 | 86.6% | 91.0% | 82.6% | 80.9% | 96.36 | −1.78 | 3.57 | 116.5 | 4.0 | |
| 3ppm6 | 86.5% | 91.1% | 82.5% | 80.8% | 96.37 | −1.81 | 3.62 | 116.6 | 4.1 | |
| 3ppm7 | 86.5% | 91.0% | 82.5% | 80.9% | 96.35 | −1.77 | 3.58 | 116.3 | 4.0 | |
| 3ppm8 | 87.1% | 91.1% | 84.0% | 82.5% | 96.39 | −1.51 | 3.10 | 116.0 | 3.4 | |
| 4ppm1 | 85.8% | 90.9% | 78.9% | 76.7% | 96.28 | −2.47 | 5.04 | 116.1 | 5.6 | 6.7 |

TABLE X-continued

| Description | Tavg | Tv | T430 | T415-430 | L | a* | b* | Hue (•) | Chroma | YI (E313-05) |
|---|---|---|---|---|---|---|---|---|---|---|
| 4ppm2 | 86.7% | 91.1% | 81.4% | 79.5% | 96.35 | −2.00 | 4.17 | 115.7 | 4.6 | 5.7 |
| 4ppm3 | 86.6% | 91.1% | 80.9% | 79.1% | 96.38 | −2.07 | 4.24 | 116.0 | 4.7 | |
| 4ppm4 | 86.5% | 91.0% | 81.0% | 79.0% | 96.35 | −2.09 | 4.30 | 115.9 | 4.8 | |
| 4ppm5 | 86.7% | 91.2% | 81.6% | 79.8% | 96.44 | −1.97 | 4.03 | 116.0 | 4.5 | |
| 4ppm6 | 86.7% | 91.1% | 81.6% | 79.7% | 96.38 | −1.96 | 4.07 | 115.7 | 4.5 | |
| 4ppm7 | 86.6% | 91.1% | 81.5% | 79.6% | 96.38 | −1.99 | 4.08 | 116.0 | 4.5 | |
| 4ppm8 | 86.4% | 91.0% | 80.8% | 78.9% | 96.33 | −2.08 | 4.30 | 115.8 | 4.8 | |

TABLE XI

| Description | Tavg | Tv | T430 | T415-430 | L | a* | b* | Hue | Chroma | YI (E313-05) |
|---|---|---|---|---|---|---|---|---|---|---|
| air | 100.0% | 100.1% | 100.0% | 100.0% | 100.03 | −0.01 | 0.01 | 145.9 | 0 | |
| Poly Control 1 | 88.8% | 91.6% | 89.9% | 89.9% | 96.63 | −0.18 | 0.68 | 105.3 | 0.7 | 0.9 |
| Poly Control 2 | 88.9% | 91.6% | 89.9% | 90.2% | 96.67 | −0.18 | 0.59 | 107.5 | 0.6 | |
| Mg2-1 (1.8 ppm) | 87.3% | 90.8% | 71.9% | 78.2% | 96.27 | −1.4 | 3.53 | 111.6 | 3.8 | 5.1 |
| Mg2-2 | 86.9% | 90.5% | 70.6% | 77.4% | 96.16 | −1.45 | 3.69 | 111.5 | 4.0 | 5.3 |
| Mg2-3 | 87.1% | 90.7% | 73.6% | 77.9% | 96.23 | −1.4 | 3.47 | 112 | 3.7 | |
| Mg2-4 | 87.0% | 90.7% | 72.3% | 77.9% | 96.2 | −1.41 | 3.52 | 111.8 | 3.8 | |
| Mg2-5 | 87.1% | 90.8% | 72.9% | 77.3% | 96.25 | −1.47 | 3.62 | 112.1 | 3.9 | |
| Mg2-6 | 87.1% | 90.7% | 72.4% | 77.6% | 96.24 | −1.39 | 3.55 | 111.4 | 3.8 | |
| Mg2-7 | 87.0% | 90.7% | 74.5% | 77.6% | 96.23 | −1.38 | 3.52 | 111.5 | 3.8 | |
| Mg2-8 | 87.1% | 90.7% | 73.6% | 77.7% | 96.24 | −1.43 | 3.54 | 111.9 | 3.8 | |
| Mg1-1 (3.7 ppm) | 85.6% | 89.9% | 62.1% | 69.9% | 95.85 | −2.16 | 5.52 | 111.4 | 5.9 | 7.8 |
| Mg1-2 | 85.8% | 90.0% | 61.9% | 70.8% | 95.9 | −2.06 | 5.32 | 111.2 | 5.7 | 7.5 |
| Mg1-3 | 85.4% | 89.8% | 60.6% | 68.3% | 95.81 | −2.29 | 5.87 | 111.3 | 6.3 | |
| Mg1-4 | 85.5% | 89.9% | 60.5% | 69.1% | 95.85 | −2.24 | 5.66 | 111.6 | 6.1 | |
| Mg1-5 | 85.2% | 89.7% | 59.2% | 67.9% | 95.79 | −2.35 | 5.95 | 111.5 | 6.4 | |
| Mg1-6 | 85.5% | 89.9% | 60.6% | 68.8% | 95.87 | −2.25 | 5.74 | 111.4 | 6.2 | |
| Mg1-7 | 85.2% | 89.7% | 60.9% | 67.6% | 95.78 | −2.34 | 5.96 | 111.4 | 6.4 | |
| Mg1-8 | 85.8% | 90.0% | 62.0% | 69.1% | 95.9 | −2.24 | 5.58 | 111.9 | 6.0 | |

The MgTMP shows a single absorption peak at slightly lower wavelength than the perylene. The average and luminous transmission changes only slightly with different dyes and dye levels since the absorption occurs over a narrow region of blue wavelengths where the eye is not particularly sensitive. More significant differences are observed for the transmission at 430 nm and from 415-430 nm due to the absorption characteristics of the dyes. The hue angle, which corresponds to the color perceived in transmission, is similar for all cases. The chroma, which is the intensity of this color, increases with higher dye levels as does the yellowness index. This tradeoff of color intensity and yellowness versus transmission is expected.

What is claimed is:

1. A dermatological product that contains a filter that inhibits transmission of light having a wavelength in the 430+/−20 nm range; wherein the filter comprises a porphyrin dye, or a porphyrin derivative, having a Soret band, and UVA and UVB inhibitors.

2. The product of claim 1, wherein the product is incorporated in a skin product, hair product, suntan product, sunscreen product, lip stick, lip balm, anti-ageing dermatology product, oil product, acne product, skin cream, skin lotion, or skin disease product.

3. The product of claim 1, wherein the filter inhibits 5-60% of light having a wavelength of 430+/−20 nm.

4. The product of claim 1, wherein the filter inhibits 5-90% of light having a wavelength of 430+/−20 nm.

5. The product of claim 1, wherein the porphyrin dye or porphyrin derivative is selected from the group consisting of: diprotonated-tetraphenylporphyrin; magnesium octaethylporphyrin; magnesium octaethylporphyrin (MgOEP); magnesium tetramesitylporphyrin (MgTMP); magnesium tetraphenylporphyrin (MgTPP); octaethylporphyrin; phthalocyanine (Pc); porphin; tetra-t-butylazaporphine; tetrakis(2,6-dichlorphenyl)porphyrin; tetrakis(o-aminophenyl)porphyrin; tetramesitylporphyrin (TMP); tetraphenylporphyrin (TPP); zinc octaethylporphyrin (ZnOEP); zinc tetramesitylporphyrin (ZnTMP); zinc tetramesitylporphyrin radical cation; and zinc tetraphenylporphyrin (ZnTPP).

6. The product of claim 1, wherein the filter further comprises a synthetic or non-synthetic antioxidant.

7. The product of claim 1, wherein the filter further comprises a natural or synthetic or derivative of a carotenoid.

8. The product of claim 1, wherein the filter is a synthetic or non-synthetic pigment.

9. The product of claim 2, further comprising infra-red radiation inhibitors.

10. The product of claim 1, wherein the filter inhibits 5-90% of light having a wavelength of 430+/−10 nm.

11. The product of claim 1, wherein the filter is incorporated into PVA or PVB.

12. The product of claim 1, wherein the filter inhibits light by absorption, reflection, interference or any combination thereof.

13. The product of claim 1, wherein the filter is an organic or inorganic compound.

14. The product of claim 1, wherein the filter further comprises lutein, zeaxanthin, melanin or any combination thereof.

* * * * *